US009109048B2

(12) United States Patent
Eliassen et al.

(10) Patent No.: US 9,109,048 B2
(45) Date of Patent: *Aug. 18, 2015

(54) INHIBITION OF TUMOR GROWTH

(75) Inventors: Liv Tone Eliassen, Kvaloysletta (NO); Gerd Berge, Tromso (NO); Baldur Sveinbjørnsson, Tromso (NO); John Sigurd Svendsen, Kvaloysletta (NO); Øystein Rekdal, Hvalstad (NO)

(73) Assignee: LYTIX BIOPHARMA AS, TromsØ (NO)

( * ) Notice: Subject to any disclaimer, the term of this patent is extended or adjusted under 35 U.S.C. 154(b) by 0 days.

This patent is subject to a terminal disclaimer.

(21) Appl. No.: 13/585,232

(22) Filed: Aug. 14, 2012

(65) Prior Publication Data

US 2014/0037657 A1    Feb. 6, 2014

Related U.S. Application Data

(63) Continuation of application No. 11/726,172, filed on Mar. 21, 2007, now Pat. No. 8,283,315, which is a continuation-in-part of application No. 09/798,026, filed on Feb. 27, 2001, now Pat. No. 7,439,228, which is a continuation of application No. PCT/GB99/02850, filed on Aug. 31, 1999.

(30) Foreign Application Priority Data

Aug. 21, 1998 (GB) .................................. 9818938.4
Mar. 21, 2006 (GB) .................................. 0605685.7

(51) Int. Cl.
*C07K 14/79* (2006.01)
*A61K 39/00* (2006.01)

(52) U.S. Cl.
CPC ............. *C07K 14/79* (2013.01); *A61K 39/0011* (2013.01); *A61K 2039/57* (2013.01)

(58) Field of Classification Search
None
See application file for complete search history.

(56) References Cited

U.S. PATENT DOCUMENTS

| | | | |
|---|---|---|---|
| 4,476,116 A | 10/1984 | Anik | |
| 5,073,542 A | 12/1991 | Zasloff | |
| 5,141,581 A | 8/1992 | Markham | |
| 5,141,851 A * | 8/1992 | Brown et al. | 435/15 |
| 5,304,633 A | 4/1994 | Tomita et al. | |
| 5,411,942 A * | 5/1995 | Widmer et al. | 514/15.7 |
| 5,428,016 A | 6/1995 | Tomita et al. | |
| 5,565,425 A | 10/1996 | Yamamoto et al. | |
| 5,593,866 A | 1/1997 | Hancock et al. | |
| 5,773,413 A | 6/1998 | Jaynes et al. | |
| 5,789,542 A | 8/1998 | McLaughlin et al. | |
| 5,962,410 A | 10/1999 | Jaynes et al. | |
| 6,255,282 B1 | 7/2001 | Jaynes | |
| 6,635,740 B1 | 10/2003 | Enright et al. | |
| 6,890,902 B2 * | 5/2005 | Svendsen et al. | 514/2.5 |
| 7,439,228 B2 * | 10/2008 | Svendsen et al. | 514/1.1 |
| 8,143,211 B2 * | 3/2012 | Svendsen et al. | 514/19.9 |
| 8,283,315 B2 * | 10/2012 | Eliassen et al. | 424/184.1 |
| 2002/0045736 A1 | 4/2002 | Yu et al. | |
| 2003/0022821 A1 | 1/2003 | Svenden et al. | |

FOREIGN PATENT DOCUMENTS

| | | |
|---|---|---|
| EP | 0299828 A1 | 1/1989 |
| EP | 0510912 A1 | 10/1992 |
| EP | 0629347 A1 | 12/1994 |
| WO | 8900194 A1 | 1/1989 |
| WO | 92/22317 A1 | 12/1992 |
| WO | 93/24138 A1 | 12/1993 |
| WO | 94/01451 A2 | 1/1994 |
| WO | 94/12206 A1 | 6/1994 |
| WO | 9527497 A1 | 10/1995 |
| WO | 96/40768 A2 | 12/1996 |
| WO | 96/40770 A2 | 12/1996 |
| WO | 98/06425 A1 | 2/1998 |
| WO | 98/06860 A1 | 2/1998 |
| WO | 98/40091 A1 | 9/1998 |
| WO | 98/40401 A2 | 9/1998 |
| WO | 00/12542 A2 | 3/2000 |
| WO | 0012541 A2 | 3/2000 |
| WO | 0119852 A2 | 3/2001 |
| WO | 0166147 A2 | 9/2001 |

OTHER PUBLICATIONS

Yoo et al., Japanese J. of Cancer Research, 1997, vol. 88, pp. 184-190.*
Risso et al., (1998), Cytotoxity and apoptosis mediated by two peptides of innate immunity. Cell Immunol. 189: 107-115.
Papo et al., (2003), A novel lytic peptide composed of DL-amino acids selectively kills cancer cells in culture and in mice. J. Biol. Chem. 278: 21018-21023.
Papo et al., (2004), Suppression of human prostate tumor growth in mice by a cytolytic D-,L-amino acid peptide: membrane lysis, increased necrosis, and inhibition of prostate-specific antigen secretion. Cancer Res. 64: 5779-5786.
Leuschner et al., (2004), Membrane disrupting lytic peptides for cancer treatments. Curr. Pharm. Des. 10: 2299-2310.
Johnstone et al., (2000), In vitro characterisation of the anticancer activity of membrane-active cationic peptides. I. Peptide-mediated cytotoxicity and peptide-enhanced cytotoxic activity of doxorubicin against wild-type and p-glycoprotein overexpressing tumor cell lines. Anticancer Drug Des. 15:151-160.

(Continued)

*Primary Examiner* — Karlheinz R Skowronek
*Assistant Examiner* — Roy Teller
(74) *Attorney, Agent, or Firm* — Fox Rothschild LLP

(57) ABSTRACT

The present invention provides a cytotoxic 7 to 25 mer peptide with three or more cationic residues which has one or more non-genetic bulky and lipophilic amino acids, as well as esters, amides, salts and cyclic derivatives thereof as well as methods of preparing the peptides, pharmaceutical compositions containing them and their use as medicaments, particularly as antibacterions or antitumoral agents. In a preferred aspect, the invention provides the use of said peptides in a method of inducing adaptive immunity against tumor growth or establishment in a subject, as well as the use of other lytic agents in a method of inducing adaptive immunity in a subject.

18 Claims, 10 Drawing Sheets

(56) References Cited

OTHER PUBLICATIONS

Risso et al., (2002), BMAP-28, an Antibiotic Peptide of Innate Immunity, Induces Cell Death through Opening of the Mitochondrial Permeability Transition Pore. Mol. Cell. Biol. 22: 1926-1935.
Powell et al., (2005), Transition of late-stage effector T cells to CD27+ CD28+ tumor-reactive effector memory T cells in humans after adoptive cell transfer therapy. Blood 105: 241-250.
Daniels et al., (2004), A simple method to cure established tumors by inflammatory killing of normal cells. Nature Biotech. 22: 1125-1132.
Parish, C. R., (2003), Cancer Immunotherapy: The past, the present and the future. Immun. Cell Biol. 81:106-113.
Dudley et al., (2003), Adoptive-cell-transfer therapy for the treatment of patients with cancer. Nature Rev. 3: 666-675.
Old, LJ. The immunotherapy of cancer. Scientific American, Sep. 1, 1996.
Saberwal, et al., Biochemica et Biophysica Acta, 1994, 1197: 109-131.
Yoo, et al., Japanese Journal of Cancer Research, 1997, 88: 184-190.
Andreu et al. (1985) Biochemistry 24:1683-1688.
Bellamy et al. (1992) Journal of Applied Bacteriology 73:472-479.
Bellamy et al. (1992) Biochimica et Biophysica Acta 1121:130-136.
Bessalle et al. (1993) J. Med. Chern. 36:1203-1209.
Blondelle et al. (1992) Biochemistry 31:12688-12694.
Boman (1995) Ann. Rev. Immunol. 13:61-92.
Chapple et al. (1998) Infection and Immunity 66:2434-2440.
Chen et al. (1988) FEB 236:462-466.
Cruciani et al. (1991) Proc. Natl Acad. Sci. USA 88:3792-3796.
Hancock et al. (1995) Advances in Microbial Physiol. 37:135-175.
Juretic et al. (1989) FEB249:219-223.
Kang et al. (1996) Int. J. Peptide Protein Res. 48:357-363.
Ludtke et al. (1996) Biochemistry 35:13723-13728.
Ranjalahy-Rasoloarijao et al. (1989) Int. J. Peptide Protein Res. 33:273-280.
Selsted et al. (1992) J. Biol. Chern. 267:4292-4295.
Stierandova et al. (1994) Int. J. Peptide Protein Res. 43:31-38.
Tomita et al. (1991) J. Dairy Sci. 74:4137-4142.
Vorland et al. (1999) ArMIS. 107:971-981.
Wieprecht et al. (1997) FEBSLetters 417:135-140.
Zasloff et al. (1988) Proc. Natl. Acad. Sci. USA 85:910-913.

\* cited by examiner

Table 1: Amino acid sequence and charge at pH 7 for synthetic lactoferricins from different species.

| Species | Sequence | Name | Charge at pH 7 |
|---|---|---|---|
| Human | T K C F Q W Q R N M R K V R G P P V S C I K R D S | LFH(18-42) | 5.85 |
| Bovine | F K C R R W Q W R M K K L G A P S I T C V R R A F | LFB(17-41) | 7.84 |
| Murine | E K C L R W Q N E M R K V G G P P L S C V K K S S | LFM(17-41) | 3.85 |
| Caprine | S K C Y Q W Q R R M R K L G A P S I T C V R R T S | LFC(17-41) | 6.85 |
| Bovine | P E W F K C R R W Q W R M K K L G A | LFB (14-31) | 6.85 |
| Bovine | F K C R R W Q W R M K K L G A | LFB (17-31) | 5.88 |
| Bovine | K C R R W Q W R M K K L G A | LFB (18-31) | 5.88 |
| Bovine | C R R W Q W R M K K L G A | LFB (19-31) | 4.88 |
| Bovine | R R W Q W R M K K L G A | LFB (20-31) | 4.91 |
| Bovine | K K C R R W Q W R M K K L G A | LFB (17-31)K17 | 6.87 |
| Bovine | F K C F R W Q W R M K K L G A | LFB (17-31)F20 | 5.87 |
| Bovine | K K C F R W Q W R M K K L G A | LFB (17-31)K17,F20 | 4.88 |
| Secondary structure | <—— Helix ——><Turn><—— Sheet ——> | | |

Figure 1

INHIBITION OF TUMOR GROWTH

CROSS-REFERENCE TO RELATED APPLICATIONS

This application is a continuation of U.S. patent application Ser. No. 11/726,172, filed Mar. 21, 2007, which is a continuation-in-part of U.S. patent application Ser. No. 09/798,026, filed Feb. 27, 2001, which is a continuation of International Patent Application Serial No. PCT/GB99/02850, filed Aug. 31, 1999, which claims the benefit UK Patent Application Serial No. GB 9818938.4, filed Aug. 21, 1998. U.S. patent application Ser. No. 11/726,172 also claims priority to UK Patent Application Serial No. GB0605685.7, filed Mar. 21, 2006. The disclosures of each of these applications are incorporated herein by reference.

FIELD OF THE INVENTION

The present invention relates to bioactive peptides, more particularly to peptides which have been modified to enhance their cytotoxic activity and the use of said peptides or other lytic agents to induce adaptive immunity in a subject.

BACKGROUND OF THE INVENTION

A wide variety of organisms use peptides as part of their host defense mechanism, in vertebrates this supplements the highly specific cell-mediated immune system [Mor, A., Hani, K. and Nicolas, P. (1994) J. Biol. Chem. 269, 31635-31641. Boman, H. G. (1996) Scand. J. Immunol. 43, 475-482]. Antimicrobial peptides have been isolated from species as diverse as bacteria and mammals [Lehrer, R. I., Lichtenstein, A. K. and Ganz, T. (1993) Ann. Rev. Immunol. 11, 105-128]. Generally, these antibiotic peptides have a net positive charge and a propensity to form amphiphilic α-helix or β-sheet structures upon interaction with the outer phospholipid bilayer in bacterial cell membranes [Besalle, R., Gorea, A., Shalit, J., Metger, J. W., Dass, C. Desiderio, D. M. and Fridkin, M. (1993) J. Med. Chem. 36 1203-1209]. In most cases the detailed molecular mechanisms of the antibiotic action are unknown, although some peptides categorized as class L (lytic) peptides are believed to interact with bacterial cell membranes, probably forming ion-channels or pores [Ludtke, S. J., He, K., Heller, W. T., Harroun, T. A., Yang, L. and Huang, H. W. (1996) Biochemistry 35 13723-13728] leading to permeability changes and consequent cell lysis.

Magainins are antibacterial peptides from the skin of the frog *Xenopus laeris* and are classified as class L antibiotics because they specifically lyse bacteria; other peptides such as mastroparans, a bee venom, lack this specificity as they lyse eukaryotic as well as prokaryotic cells and are called Class L Venoms [Tytler, E. M., Anantharamaiah, G. M., Walker, D. E., Mishra, V. K., Palgunachari, M. N. and Segrest, J. P. (1995) Biochemistry 34 4393-4401]. Anti-biotic resistance exhibited by certain infectious microorganisms is an increasing problem and there is always a need for new antibiotics. Anti-bacterial peptides such as the class L peptides are known and more are being discovered, with the aim of finding a peptide which is highly cytotoxic and preferably specific for prokaryotic cells. There are differences in the structure and composition of lipid bi-layers between eukaryotes and prokaryotes and amongst prokaryotes themselves which mean that different peptides will have widely differing specificities.

As well as magainins and mastroparans, host defense peptides have been isolated from moths and flies (cecropins) and from Horseshoe crab. The direct action of these host defense peptides to repel predators, for example as venoms, is clear. The search for peptides which exhibit antibiotic effects has lead to the identification of other proteins/peptides which would not be expected to have cytotoxic properties. One of these is lactoferrin, an iron transporter which also shows a weak antibacterial effect.

As well as searching for new antimicrobial peptides, more recently it has been sought to enhance the activity of proteins or peptides with known antimicrobial properties. This has been done in the case of bovine lactoferrin by digesting the native protein with gastric pepsin to produce a peptide, lactoferricin B (LFB), which is much more active than the native bovine lactoferrin. LFB is a 25 residue peptide which corresponds to residues 17-41 of bovine lactoferrin. [Bellamy et al. (1992) Biochem. Biophys. Acta. 1121 pp 130 et seq.]. Structure-activity studies have been carried out on magainins and it has been shown, for example, that enhancement of helicity and of the cationic charge leads to higher antibacterial activity [Chen, Y. H., Brown, J. H., Morell, J. L. and Huang, C. M. (1988) FEES Letters 236, 462-466]. However, such sequence modifications often result in higher hemolytic activity. It is thus an object of the present invention to prepare peptides and/or peptide derivatives which have significant antibacterial activity but preferably have low toxicity, i.e. little effect on normal eukaryotic cells, e.g. low hemolytic activity. While red blood cells may not be typical eukaryotic cells, they provide a convenient way of assaying for toxicity and in any event are a type of cell which should not be lysed to a significant extent by therapeutic bioactive peptides.

SUMMARY OF THE INVENTION

It has been found that by increasing the bulk or lipophilic nature of a peptide, its bioactivity can be increased, in particular its cytotoxicity. Preferably, the bulk and lipophilicity of one or more amino acid residues is increased. It has also been found that adaptive immunity against tumor growth or establishment can be induced in a subject through administration of an effective amount of a lytic compound to said subject.

Therefore, the invention provides a method of inducing adaptive immunity against tumor growth or establishment (i.e., tumor formation) in a subject, comprising administering an effective amount of a lytic compound to the subject.

Also provided is a method of vaccinating a subject against tumor cell growth or establishment by administering an effective amount of a lytic compound to the subject.

Further provided is a method of treating cancer in a subject in need of such treatment wherein the method comprises administering to the subject an effective amount of a lytic compound wherein the lytic compound, through lysis of cells in a first tumor, generates an immune response which inhibits tumor cell formation or growth of a second tumor.

DETAILED DESCRIPTION OF THE INVENTION

Thus, according to the present invention is provided a cytotoxic 7 to 25 mer peptide with three or more cationic residues which is optionally capable of forming an amphiphatic α-helix and which either has one or more non-genetic bulky and/or lipophilic amino acids or has at least a 40% sequence homology with a known or natural cytotoxic peptide and one or more extra bulky and/or lipophilic amino acids, as well as esters, amides, salts and cyclic derivatives thereof.

The % homology is preferably 50 or 60% or more, particularly 70 or 80% or more. For the purposes of the present invention, the term "sequence homology" is not used to refer to sequence identity but to the presence of either the same amino acid or one from the same functional group. The standard genetically coded amino acids can be grouped according to their characteristics, particularly of polarity and charge. Convenient groupings are, glycine and alanine, serine, threonine, asparagine, glutamine and cysteine, lysine, arginine and histidine, aspartic acid and glutamic acid and valine, leucine, isoleucine, methionine, phenylalanine, tryptophan and tyrosine. Of the 20 standard (genetic) amino acids, valine, leucine, isoleucine, methionine, tyrosine, tryptophan and phenylalanine are intended to be covered by the term "bulky and/or lipophilic" amino acid, isoleucine, tryptophan and phenylalanine being preferred. Throughout this specification, the widely used and understood three letter and one letter code for the 20 standard amino acids has been used. Replacement of an amino acid from one group with another amino acid in the same group is conveniently referred to as a "conservative substitution". Such substitutions do not generally materially effect the properties of the peptides of the invention and where any peptide differs from another only by such substitutions, if one peptide is a peptide according to the present invention then typically the other peptide will also be a peptide according to the invention.

According to a preferred aspect of the present invention is provided a cytotoxic 7 to 25 mer peptide with three or more cationic residues which is optionally capable of forming an amphipathic α-helix and which has one or more non-genetic bulky and lipophilic amino acids, as well as esters, amides, salts and cyclic derivatives thereof.

Peptides incorporating a non-genetic bulky and lipophilic amino acid will preferably exhibit an enhanced cytotoxic effect against bacterial or tumor cells while the toxicity of the peptides, e.g. their hemolytic activity is reduced or only moderately increased as compared to the native or original peptide.

It has surprisingly been found that amino acids or their derivatives of a certain size can be used to provide modified peptides which are particularly suitable for use as cytotoxic peptides. Thus, according to the invention, by "non-genetic bulky and lipophilic amino acid" is meant any amino acid or amino acid derivative, which may be naturally occurring, but not one of the 20 standard genetically coded amino acids, whose R group (α-side chain) is preferably uncharged and has at least 7, preferably 8, more preferably 9 non-hydrogen atoms. Particularly preferred non-genetic bulky and lipophilic amino acids will have at least 12, preferably at least 18 non-hydrogen atoms in the R group. By way of example, the R group of the amino acid phenylalanine has 7 non-hydrogen atoms but as it is one of the genetically coded or 'standard' amino acids, it does not fall within our definition of "non-genetic bulky and lipophilic amino acids". The term 'non-hydrogen' is used to indicate that hydrogen atoms are not included when counting the number of atoms present in a group or molecule.

Preferably, the R group in the non-genetic bulky and lipophilic amino acid will have at least 8 or 9 non-hydrogen e.g. carbon atoms, ideally including a closed ring system, more preferably it should have at least 2 closed rings of 5 or 6 atoms and conveniently these two rings are fused or bridged. The group may comprise only one ring which is substituted by heavily branched alkyl groups which include more than one branch site or one branch site which has 4 attachments to non-hydrogen atoms. The rings are formed of carbon atoms, optionally also including nitrogen, oxygen or sulphur atoms. Particularly preferred amino acids comprise a substituted or unsubstituted indole. The group should preferably be three-dimensional.

Preferred non-genetic bulky and lipophilic amino acids include adamantylalanine, 3-benzothienylalanine, 4,4'-biphenylalanine, 3,3-diphenylalanine, homophenylalanine, 2,6-dichlorobenzyltyrosine, cyclohexyltyrosine, 7-benzyloxytryptophan, tri-tert-butyltryptophan, homotryptophan, 3-(-anthracenyl)-L-alanine, L-p-iso-propylphenylalanine, L-thyroxine, 3,3',5-triiodo-L-thyronine.

A lipophilic molecule is one which associates with its own kind in an aqueous solution, not necessarily because the interactions between the lipophilic molecules are stronger than between the lipophilic molecule and water but because interactions between a lipophilic molecule and water would destroy the much stronger interactions between the water molecules themselves. It is therefore preferable that the R group of the non-genetic bulky and lipophilic amino acid should not contain many polar functional groups e.g. no more than 4, preferably 2 or less. Such groups would increase the binding interaction with the aqueous surroundings and hence lower the lipophilicity of the molecule. Highly lipophilic groups are thus preferred. For example, a phenyl group as a component of a bulky and lipophilic group would be preferred to a pyridyl group, even though they have the same number of non-hydrogen atoms and are of a similar overall size.

Suitable bulky and lipophilic amino acid residues will therefore include naturally occurring and non-naturally occurring amino acids which have an R group as previously defined, e.g. adamantylalanine or any amino acid, including genetically coded amino acids, whose R groups have been modified to provide a non-genetic bulky and lipophilic amino acid as previously defined.

Non-genetic bulky and lipophilic amino acids in this second category include modified tryptophan and phenylalanine residues, in particular tryptophan residues which have been substituted at the 1-, 2-, 5- and/or 7-position of the indole ring, positions 1- or 2-being preferred. A variety of other amino acid derivatives having a bulky and lipophilic character are known to the skilled man and are intended to be included within the term "non-genetic bulky and lipophilic amino acid".

Suitable Amino Acids Include Thyroxine and the Following Commercially Available Amino Acids and their Derivatives:

L-3-benzothienylalanine, CAS=72120-71-9 (Synthetech), D-3-benzothienylalanine, CAS=111139-55-0 (Synthetech), L-4,4'-biphenylalanine (Synthetech), D-4,4'-biphenylalanine (Synthetech), L-4-bromophenylalanine, CAS=24250-84-8 (Synthetech), D-4-bromophenylalanine, CAS=62561-74-4 (Synthetech), L-2-chlorophenylalanine, CAS=103616-89-3 (Synthetech), D-2-chlorophenylalanine, CAS=80126-50-7 (Synthetech), L-3-chlorophenylalanine, CAS=80126-51-8 (Synthetech), D-3-chlorophenylalanine, CAS=80126-52-9 (Synthetech), L-4-chlorophenylalanie, CAS=14173-39-8 (Synthetech), D-4-chlorophenylalanine, CAS=14091-08-8 (Synthetech), L-3-cyanophenylalanine, CAS=57213-48-6 (Synthetech), D-3-cyanophenylalanine (Synthetech), L-4-cyanophenylalanine (Synthetech), D-4-cyanophenylalanine (Synthetech), L-3,4-dichlorophenylalanine, CAS=52794-99-7 (Synthetech), D-3,4-dichlorophenylalanine, CAS=52794-98-6 (Synthetech), L-3,3-diphenylalanine (Synthetech), D-3,3-diphenylalanine (Synthetech), L-homophenylalanine, CAS=943-73-7 (Synthetech), D-homophenylalanine, CAS=82795-51-5 (Synthetech), L-2-indanylglycine (Synthetech), D-2-indanylglycine (Synthetech), L-4-iodophenylalanine, CAS=24250-85-9 (Synthetech), D-4-iodophenylalanine, CAS=62561-75-5 (Synthetech), L-1-naphthylalanine, CAS=55516-54-6 (Synthetech), D-1-naphthylalanine, CAS=78306-92-0 (Synthetech), L-2-Naphthylalanine, CAS=58438-03-2 (Synthetech), D-2-naphthylalanine, CAS=76985-09-6 (Synthetech), L-3-trifluoromethylphenylalanine, CAS=14464-68-7 (Synthetech), D-3-trifluoromethylphenyl-alanine (Synthetech), L-4-trifluoromethylphenylalanine, CAS=114926-38-4 (Synthetech), D-4-trifluoromethyl-phenylalanine, CAS=114872-99-0 (Synthetech), Boc-D-homophenylalanine (Neosystem Laboratoire), Boc-L-homophenylalanine (Neosystem Laboratoire), Fmoc-4-methyl-D-phenylalanine (Neosystem Laboratoire), Fmoc-4-methyl-L-phenylalanine (Neosystem Laboratoire), 2,6-dichlorobenzyltyrosine, CAS=40298-71-3 (Senn Chemicals), Benzyltyrosine Fmoc (Senn Chemicals), Cyclohexyltyrosine Fmoc (Senn Chemicals), L-3,5-diiodotyrosine, CAS=300-39-0 (Senn Chemicals), D-3,5-diiodotyrosine (Senn Chemicals), L-3,5-dibromotyrosine (Senn Chemicals), D-3,5-dibromotyrosine (Senn Chemicals), L-t-butyltyrosine (Senn Chemicals), L-t-butyltyrosine (Senn Chemicals), N-Acetylhomotryptophan (Toronto Research), 7-Benzyloxytryptophan (Toronto Research), Homotryptophan (Toronto Research), 3-(-Anthracenyl)-L-alanine Boc (or Fmoc) (Peninsula Laboratories), 3-(3,5-Dibromo-4-chlorophenyl)-L-alanine (Peninsula Laboratories), 3-(3,5-Dibromo-4-chlorophenyl)-D-alanine (Peninsula Laboratories), 3-(2-Quinoyl)-L-alanine Boc (or Fmoc) (Peninsula Laboratories), 3-(2-Quinoyl)-D-alanine Boc (or Fmoc) (Peninsula Laboratories), 2-Indanyl-L-glycine Boc (Peninsula Laboratories), 2-Indanyl-D-glycine Boc (Peninsula Laboratories), L-p-t-butoxyphenylglycine Fmoc (RSP), L-2-t-butoxyphenylalanine Fmoc (RSP), L-3-t-butoxyphenylalanine Fmoc (RSP), L-homotyrosine, O-t-butyl ether Fmoc (RSP), L-p-t-butoxymethylphenylalanine Fmoc (RSP), L-p-methylphenylalanine Fmoc (RSP), L-p-ethylphenylalanine Fmoc (RSP), L-p-iso-propylphenylalanine Fmoc (RSP), L-p-methoxyphenylalanine Fmoc (RSP), L-p(tButhio)phenylalanine Fmoc (RSP), L-p-(Trt-thiomethyl)phenylalanine Fmoc (RSP), L-p-hydroxymethyl-phenylalanine, O-t-butyl (RSP), L-p-benzoylphenylalanine (Advanced ChemTech), D-p-benzoyl-phenylalanine (Advanced ChemTech), O-benzyl-L-homoserine Boc (Advanced ChemTech), O-benzyl-D-homoserine Boc (Advanced ChemTech), L-β-1-Naphthyl-alanine (Advanced ChemTech), D-β-1-Naphthyl-alanine (Advanced ChemTech), L-penta-fluorophenylalanine Boc (Advanced ChemTech), D-penta-fluorophenylalanine Boc (Advanced ChemTech), D-penta-fluorophenylalanine Fmoc (Advanced ChemTech), 3,5-Diiodo-L-tyrosine Fmoc (Boc) (Advanced ChemTech), L-Thyroxine Na, CAS=6106-07-6 (Novabiochem), 3,3',5-Triiodo-L-thyronine Na, CAS=55-06-1 (Novabiochem).

Surprisingly, it has been found that standard chemical protecting groups when attached to an R group and thus increasing the bulk and lipophilicity of the residue can increase the bioactivity of peptides. Such protecting groups are well known in the art. Suitable protecting groups which can significantly enhance anti-bacterial activity include Pmc (2,2,5,7,8-pentamethylchroman-6-sulphonyl), Mtr (4-methoxy-2,3,6-trimethylbenzenesulfonyl) and Pbf (2,2,4,6,7-pentamethyldihydrobenzofuransulfonyl), which may conveniently increase the bulk and lipophilicity of aromatic amino acids, e.g. Phe, Trp and Tyr. Also, the tert-butyl group is a common protecting group for a wide range of amino acids and is capable of providing non-genetic bulky and lipophilic amino acids as described herein, particularly when modifying aromatic residues. The Z-group (carboxybenzyl) is a further protecting group which can be used to increase the bulk and lipophilicity of an amino acid to provide a peptide in accordance with the invention.

Although the initial observation of increased bioactivity was as a result of a serendipitous transfer of the protecting group Pmc within the peptide from the guanidino group of arginine to tryptophan, amino acids such as Trp which carry the protecting group can be synthesised directly and incorporated into the peptide.

This observation of the transfer of Pmc from Arg to Trp has been observed by Stierandova et al. in Int. J. of Peptide Science (1994) 43, 31-38. Peptides in accordance with the invention can be made by utilising this transfer of the protecting group from Arg to Trp. When these two amino acids are separated by 1-3 amino acids the transfer of Pmc is most efficient. Peptides according to the invention may thus conveniently comprise an amino acid carrying a protecting group, e.g. Trp with Pmc attached in the 2 position of the indole ring. The Pmc group may be attached to a Trp which has been added or to a Trp residue present in the original peptide. In a preferred embodiment of the invention, peptides will incorporate one or more additional tryptophan residues which can then be modified to further increase its bulky and lipophilic character and thus provide a peptide according to the invention.

In the context of the present invention, "cyclic derivatives" refers to peptides which are cyclic as a result of one or more di-sulphide bridges. For some peptides incorporating two or cysteine residues, this will be the naturally occurring form and production of a linear peptide will require the modification of the cysteine residues.

The non-genetic bulky and lipophilic amino acid may be present in addition to the amino acids of the original sequence, which may itself be a naturally occurring peptide or fragment thereof or incorporate other modifications to a naturally occurring peptide or fragment or be entirely synthetic. Alternatively and preferably, the non-genetic bulky and lipophilic amino acid may be in place of one of the amino acids in the original sequence. When the amino acid is 'added', then all original amino acids in the peptide remain. When the extra amino acid is "substituted", it replaces one of the original amino acids, although a replacement may include modification of the existing residue to provide a non-genetic bulky and lipophilic amino acid as previously defined.

The non-genetic bulky and lipophilic amino acid is preferably present in place of another, naturally occurring, non-essential amino acid. By "non-essential" is meant an amino acid whose presence is not required for the peptide as a whole to demonstrate cytotoxic activity. Typically, the peptide prior to incorporation of a non-genetic bulky and lipophilic amino acid will exhibit some cytotoxic activity, this activity being enhanced by the incorporation of a non-genetic bulky and lipophilic amino acid.

In a preferred embodiment of the invention, the non-genetic bulky and lipophilic amino acid will be present adjacent to or preferably in place of a genetic bulky and lipophilic amino acid present in the original peptide. In other words, an already bulky and lipophilic amino acid is made more bulky and lipophilic. This can be achieved by modification of the R group of the original amino acid or by replacing that amino acid with a non-genetic amino acid. The genetically coded amino acids which can be considered bulky and/or lipophilic are defined previously. Thus, in a preferred embodiment of the present invention, the peptides will incorporate a non-genetic bulky and lipophilic amino acid in the form of e.g. a modified tryptophan residue (e.g. Trp-Pmc) or e.g. tributyl-tryptophan residue in place of e.g. tryptophan or phenylalanine.

Preferably, the peptides of the invention will incorporate between 1 and 5, e.g. 2 or 3 non-genetic bulky and lipophilic amino acids as herein defined.

For any given cytotoxic peptide, suitable positions for incorporation of non-genetic bulky and lipophilic amino acids in order to increase cytotoxicity can be identified in a number of ways. As discussed above, "incorporation" may include modification of an existing residue. An alanine scan (involving sequential substitution of the amino acids with alanine) can be used to identify non-essential amino acids which could be substituted by a bulky and lipophilic amino acid or modified to increase its bulk and lipophilicity. Alternatively, a candidate peptide which forms an amphiphatic α-helix can be represented as a 'helical wheel' of residues and the cationic residues identified. These cationic residues will form positively charged domains or regions within the three-dimensional helical peptide structure and suitable positions for incorporation of or modification to provide non-genetic bulky and lipophilic amino acids are generally adjacent to or between such cationic domains when viewed along the axis of the helical wheel.

It has even been found that peptides having enhanced antibacterial and/or antitumoral activity and preferably reduced toxicity can be prepared by moving a bulky and lipophilic amino acid from its position in the original/native sequence to a region adjacent to the cationic sector, thus the overall amino acid composition of the peptide remains unchanged. Such 7-25 mer peptides which have 3 or more cationic residues and are capable of forming an amphipathic α-helix and which have an extra bulky and lipophilic amino acid adjacent to the cationic sector, said extra bulky and lipophilic amino acid being taken from another, non-preferred, position in the sequence constitute a further aspect of the present invention. In place of the bulky and lipophilic amino acid can be put the residue from adjacent to the cationic sector which the bulky and lipophilic amino acid replaces or any other less bulky and lipophilic amino acid. Suitable bulky and lipophilic amino acids in non-preferred positions which can be moved into the region adjacent to the cationic sector (preferred position) can be identified by e.g. an alanine scan which identifies non-essential amino acids or by studying a helical wheel arrangement, non-preferred positions typically being opposite a cationic domain.

It has also been found that peptides having reduced toxicity but still having reasonable antibacterial or anti-tumoral activity (i.e. having enhanced selectivity) may be prepared by replacing a non-essential highly bulky and lipophilic amino acid such as tryptophan or phenylalanine with a less bulky and lipophilic amino acid e.g. isoleucine or leucine or even alanine or lysine. Generally, a "non-essential" bulky and lipophilic amino acid will be positioned on the opposite side of the helix from the cationic sector, such non-essential bulky and lipophilic amino acids can be identified using a helical wheel diagram or by an alanine scan. These peptides should nevertheless retain at least 3 bulky and lipophilic amino acids as herein defined. Thus, modified cytotoxic peptides having 7 to 25 amino acids, at least three cationic residues and at least three bulky and lipophilic amino acids and being capable of forming an amphipathic α-helix, wherein one non-essential tryptophan or phenylalanine residue in the original/native sequence is replaced by a less bulky and lipophilic residue e.g. isoleucine or alanine constitute a further aspect of the present invention. Indolicin is a naturally occurring tryptophan rich peptide which may conveniently be modified in this way to reduce its toxicity.

Other suitable sites for incorporation of a bulky and lipophilic amino acid are positions at or near, preferably adjacent, to an existing lipophilic amino acid. Proximity is judged in terms of the secondary rather than primary structure of the peptide. The techniques involved in performing an alanine scan and in constructing helical wheel diagrams are well known in the art.

In the case of LFB(17-31) (a 15 amino acid fragment of LFB which lacks the ten C-terminal residues), non-essential amino acids determined using an alanine scan were Cys(3), Gln(7) and Gly(14), here the numbering is in absolute terms relating to the peptide itself. Analogs of LFB(17-31) wherein these amino acids are replaced by non-genetic bulky and lipophilic amino acids may be particularly effective. For modifications to magainin peptides such as magainin 2, incorporation of non-genetic bulky and lipophilic amino acids at positions Phe(16) and Glu(19) may be particularly effective.

In addition to the presence of one or more non-genetic bulky and lipophilic amino acid, the peptides according to the invention may advantageously incorporate further modifications. In particular, increasing the overall positive change of the peptide, for example by replacing one or more naturally occurring amino acids, particularly non-essential amino acids, with one or more positively charged residues such as lysine or arginine may further enhance the activity of the peptide. "Positively charged" refers to the side chain (R group) of the amino acid residue which has a net positive charge at pH 7.0. In the case of peptides for use as anti-tumor agents, where the peptide may advantageously be capable of forming α-helix, substitutions within the peptide sequence which serve to lower the angle subtended by the cationic sector, i.e. the angle of the positively charged face of the helix may further enhance activity. In fact, lowering the angle subtended may have a greater impact on activity than the net positive charge per se. Other residues may advantageously be replaced by alanine. Additional 'genetic' bulky and/or lipophilic amino acids as defined herein, e.g. Trp or Phe may also advantageously be incorporated.

Suitable peptides which can be modified to provide peptides in accordance with the invention include all peptides such as the magainins, PGLa analogues, cecropins, defensins, melittin and lactoferrin, and class (L) lytic peptides generally etc. which are known in their unmodified form to exhibit cytotoxic, particularly anti-microbial activity. Further suitable peptides include those which are not naturally occurring but have been synthesised and exhibit cytotoxic activity, such peptides include the modelines. In this context, "unmodified" includes fragments obtained by digestion of naturally occurring proteins or peptides. New anti-bacterial proteins and peptides are still being discovered and it is believed that the techniques of the present invention have general applicability and could be applied simply, and with a reasonable chance of success, to peptides which are as yet unidentified but are subsequently characterised as cytotoxic, particularly as anti-microbial.

Particularly preferred peptides according to the present invention are those which are based on fragments of lactoferrin, particularly those based on bovine lactoferrin (LFB) or fragments (e.g. LFB 17-31) thereof or the equivalent fragment of lactoferrin from other animals.

A particular advantage of the peptides of the present invention is their small size, peptides having 15 or fewer amino acids being preferred, conveniently of 9 or 10 amino acids or less. One such effective small peptide is LFB(17-27) wherein the Lys28, Leu29, Gly30 and Ala31 from the C-terminal end of LFB(17-31) have been omitted. The peptides may be produced by any known method, conveniently by enzymatic digestion or chemical cleavage of native peptides and subsequent modification or by direct synthesis from the amino acid building blocks. The shorter the desired peptide the better as far as manufacture is concerned, particularly for direct synthesis which is the preferred method of manufacture, as this limits the problems associated with chirality of the amino acids. In addition, short peptides are good for biodelivery. There is a growing demand for anti-biotics which can be administered without the need for an injection, such as by inhalation and absorption across the blood capillaries of the nasal passages. A 10 mer peptide could easily be administered in this way but peptides in excess of 25 amino acids in length could not be delivered by inhalation.

It would also be desirable to increase the circulating half-life of the peptide and this could be achieved by further modifying the peptides of the invention to include artificial amino acids as they are resistant to enzymatic breakdown. Long peptides are susceptible to breakdown by endopeptidases which cleave internally of the peptide, shorter peptides would be less vulnerable to cleavage by endopeptidases and breakdown by exopeptidases, which attack the ends of a peptide, could be reduced by acetylating the N terminus and otherwise blocking the C terminus.

It has also been observed that the incorporation of enantio amino acids can significantly increase the bioactivity of the peptides of the invention and such peptides constitute a further preferred embodiment of the present invention. Excellent antimicrobial activity has been shown for Enantio peptides which are the exact mirror image of the native peptide and Retro-Enantio peptides which adopt the same α-helical confirmation as the native peptide except the amide bonds point in opposite directions. Preferably, in accordance with the invention, such peptides will also incorporate a non-genetic bulky and lipophilic amino acid as previously defined.

Enantio amino acids are also resistant to enzymatic breakdown and the resultant increase in half-life of the peptides may go some way to explaining the enhanced anti-bacterial activity. Enantio amino acids are expensive and this is a further reason why the relatively short peptides of the present invention are particularly advantageous.

Further preferred peptides according to the invention therefore incorporate a non-genetic bulky and lipophilic amino acid as previously defined and also comprise one or more D-amino acids, e.g. _ or ½ or _ of the amino acids are in the D form and these may be arranged in any way throughout the sequence e.g. alternately with L amino acids.

By the term "capable" of forming an amphipathic α-helix is meant that the peptide may, in certain circumstances, form an α-helix. Peptides may not necessarily have the α-helix as their natural configuration in aqueous media but are able, for example in the presence of helix providing substances such as sodium dodecylsulphate (SDS), 2,2,2-trifluoroethanol (TFE), 1,1,1,3,3,3-hexafluoroisopropanol (HFIP) or micelles other than SDS and cell membranes (artificial and natural) to form an α-helix or substantially α-helical structure. Circular dichroism may conveniently be used to test for the presence of an α-helix.

Of more importance than the formation of an α-helix is the fact that the peptides are amphipathic, i.e. that the 2° structure of the peptide, whether it is α-helical or not, is amphipathic. This is evidenced by the good activity of enantio peptides which do not form an α-helix in any environment and peptides incorporating one or more D-amino acids, the requirement for an amphipathic α-helical conformation is thus not an essential requirement of the present invention.

In addition, the present invention relates to non-peptide compounds showing the same cytotoxic activity as their proteinaceous counterparts. Such peptidomimetics or "small molecules" capable of mimicking the activity of a protein or peptide are likely to be better suited for e.g. oral delivery due to their increased chemical stability. Such compounds will include a part which corresponds to the "non-genetic bulky and lipophilic amino acid" as previously defined. More particularly, they will include a group which corresponds to the R group of said non-genetic bulky and lipophilic amino acid, i.e. it has at least 7, preferably at least 9, non hydrogen atoms in the equivalent of the R group, that group being uncharged and preferably comprising few polar groups.

It is now commonplace in the art to replace peptide or protein-based active agents e.g. therapeutic peptides with such peptidomimetics having functionally-equivalent activity. Various molecular libraries and combinatorial chemistry techniques exist and are available to facilitate the identification, selection and/or synthesis of such compounds using standard techniques (Kieber-Emons, T. et al. Current Opinion in Biotechnology 1997 8: 435-441). Such standard techniques may be used to obtain the peptidomimetic compounds according to the present invention, namely peptidomimetic organic compounds which show substantially similar or the same cytotoxic activity as the peptides of the invention, e.g. as described herein in the Examples.

A further aspect of the invention thus provides a biomimetic organic compound based on the peptides of the invention, characterised in that said compound exhibits cytotoxic, e.g. antibacterial or antitumoral activity, at at least the level exhibited by the peptides of the invention as hereinbefore defined.

The term "cytotoxic" is intended to refer not only to an activity against prokaryotic cells but also against eukaryotic cells. Although in certain circumstances it is desirous to have a peptide which has a good anti-bacterial activity but does not lyse or otherwise destroy the cells of the patient, peptides within the scope of the present invention have been shown to have an anti-tumoral activity. The anti-tumoral activity of these peptides and medicaments containing them constitute further aspects of the present invention. Anti-tumoral activity includes the destruction or reduction in size or number of benign or malignant tumors and the prevention or reduction of metastasis.

In general, lactoferrin derived peptides according to the invention which have no non-genetic amino acids and have a good activity against tumor cells will have 25-10, preferably 12-20 e.g. 18 amino acids. Peptides according to a non genetic bulky and lipophilic group and having good anti-tumoral activity will generally be shorter, with 7-20, preferably 10-20, more preferably 10-15 amino acids. By way of example, LFB 17-27 A7, M3, R2, 11W4, 10, Y1-NH$_2$ PMC and LFB 18-24 R1, 7 W2, 3, 6-NH$_2$ PMC require only 50 and 38 μg/ml respectively to kill 50% of Meth A cells.

In general, peptides having good activity against tumors will be longer than those exhibiting good anti-bacterial activity. Anti-bacterial peptides will typically have 7 to 20, preferably 7 to 14, e.g. 8 or 9 amino acids.

The anti-tumoral activity of the modified peptides is much better than could be predicted merely from the fact that the peptides appear to have a lytic effect on bacterial cells. The observed lytic effect on tumor cells in vitro is powerful and tumor regression in mice is very rapid, occurring within 3-6 days. It appears that there is induction of an immunological memory, as inoculation of tumor cells in mice after the treatment and regression of the original tumor did not give rise to any secondary tumor growth.

Importantly, we have demonstrated regression of established tumors, even with unmodified LFB. In this context, "unmodified" refers also to fragments of LFB which exhibit this antitumoral activity, e.g. LFB(17-31). The peptide may be cyclic or linear, preferably cyclic. The ability to treat solid tumors is particularly useful when a tumor is unresectable. A further advantage is that the observed cytolytic effect in tumors is not species specific and thus the peptides have utility in treating human tumors.

Suitable doses for treatment of tumors with bioactive peptides will be known to the skilled man and doses used in the animal experiments described herein can be used to estimate an appropriate dose for other animal and human patients. Administration of a peptide may be daily, more usually on alternate days or on every 3rd or 4th day. 1 to 10, typically 2 to 5 administrations may result in successful treatment. Similar treatment protocols will be used for treatment of bacterial or viral infections.

Peptides according to the invention will preferably be at least as cytotoxic as LFB (17-31). Some peptides according to the invention will be more active in some respects (e.g. antitumoral) than LFB (17-31) but less active in other respects e.g. against E. coli. Some peptides may be less active but other properties e.g. a low hemolytic activity will render them useful in certain applications.

The antibacterial activity of the peptides of the invention may manifest itself in a number of different ways. Certain modifications may result in peptides which are bacteriostatic and others in peptides which are bacteriocidal. Advantageously, the majority of the peptides according to the invention are bacteriocidal. Thus, inter alia, the invention also provides a method of inhibiting the growth of bacteria comprising contacting the bacteria with an inhibiting effective amount of a cytotoxic peptide according to the invention.

The term "contacting" refers to exposing the bacteria to a peptide so that it can effectively inhibit, kill or lyse bacteria, bind endotoxin (LPS), or, permeabilize gram-negative bacterial outer membranes. Contacting may be in vitro, for example by adding the peptide to a bacterial culture to test for susceptibility of the bacteria to the peptide. Contacting may be in vivo, for example administering the peptide to a subject with a bacterial disorder, such as septic shock. "Inhibiting" or "inhibiting effective amount" refers to the amount of peptide which is required to cause a bacteriastatic or bacteriacidal effect. Examples of bacteria which may be inhibited include E. coli, P. aeruginosa, E. cloacae, S. typhimurium and S. aureus. The method of inhibiting the growth of bacteria may further include the addition of antibiotics for combination or synergistic therapy. The appropriate antibiotic administered will typically depend on the susceptibility of the bacteria such as whether the bacteria is gram negative or gram positive, and will be easily discernable by one of skill in the art.

In addition, different modifications may enhance the antibacterial activity against certain types of bacteria more than against other types. For example S. aureus is particularly susceptible to very large bulky and lipophilic groups, typically those having at least 12 or 18 non-hydrogen atoms in the R group e.g. those peptides which incorporate a Pmc modified tryptophan residue. In addition, R groups which are substantially planar have good activity against E. coli while a more 3-dimensional group of comparable lipophilicity is preferred for producing good activity against S. aureus.

Although, as discussed above, the technique of enhancing activity by introducing a non-genetic bulky and lipophilic amino acid is of general applicability to a wide variety of cytotoxic peptides, particularly to class L (lytic) peptides, of particular interest are mammalian derived peptides, particularly peptides derived from lactoferrin, especially lactoferricin. It has been found that the sequence of bovine lactoferricin (LFB 17-41) can be reduced by up to about 10 residues at the C-terminal end, e.g. to LFB(17-31) without significant loss of antibacterial activity. LFB 17-31=FKCR-RWQWRMKKLGA (SEQ ID NO: 1). As well as bovine lactoferricins, we have identified the regions corresponding to LFB 17-31 in man, LFH=TKCFQWQRNMRKVRG (SEQ ID NO: 2), goat, LFC=SKCYQWQRRMRKLGA (SEQ ID NO: 3), mice, LFM=EKCLRWQNEMRKVGG (SEQ ID NO: 4) and pigs, LFP=SKCRQWQSKIRRTNP (SEQ ID NO: 5) and such regions are also suitable for manipulation according to the invention.

A variant of the effects of an increase in lipophilicity of certain peptides discussed above has been observed and a further aspect of the present invention comprises a cytotoxic peptide of 15 amino acids or less characterised in that it has an additional bulky/lipophilic group at one end. In respect of this aspect of the invention, the bulky/lipophilic group includes organic groups such as protecting groups, especially Fmoc, Boc or other standard N terminal protecting groups or branched, linear or cyclic alkyl groups of formula $CH_3(CH_2)_n$ wherein n is between 5 and 20, preferably between 8 and 14 and most preferably 10 to 12 or branched, linear or cyclic acyl groups having between 6 and 21, preferably 9 and 15 and most preferably 11 to 13 carbon atoms. For example, an LFB(17-31) peptide having a $CH_3(CH_2)_n$ alkyl group at the N-terminal end had an up to 10 fold increase in antibacterial activity. The groups are attached to N- or C-terminal or close, preferably adjacent, to N- or C-terminal residues. These groups may be attached to native amino acid residues, or non-native amino acids carrying the bulky/lipophilic group may be incorporated into the peptide. The appropriate definition of "cytotoxic peptide" is as discussed above.

The bulky/lipophilic nature of an amino acid and thus of a peptide can be enhanced by N- or C-terminal modification and such modifications result in further peptides according to the present invention.

Thus peptides may, in addition to or instead of incorporating a non-genetic bulky and lipophilic amino acid as previously defined, therefore be modified at the N- and/or C-terminus. More specifically, it has been found that peptides having antibacterial and/or antitumoral activity but a low toxicity can be made by incorporating N-terminal modifications which include a cyclic group, preferably a 5- or 6-membered ring which may be alkyl or aryl. More preferably the group which comprises the N-terminal modification encompasses 2 or more fused rings one or more of which may be a 5-membered ring e.g. adamantyl or Fmoc. It has surprisingly been found that groups which are three dimensional in character, such as those which incorporate a fused ring system which does not lie in a single plane have particularly advantageous properties.

Suitable molecules which could be used to modify the N-terminus include:

cis-Bicyclo[3.3.0]octan-2-carboxylic acid, [18209-43-3] (Aldrich); Abietic acid, [514-10-3] (Aldrich); Ursolic acid, [77-52-1] (Aldrich); (1,2-Methanofullerene $C_{60}$)-61-carboxylic acid, [155116-19-1] (Fluka); Dimethyl cubane-1,4-dicarboxylate, [29412-62-2] (Fluka); 2-Norbornaneacetic acid, [1007-01-8] (Aldrich); 4-Pentylbicyclo[2.2.2]octane-1-carboxylic acid, [73152-70-2] (Aldrich); 3-Noradamantanecarboxylic acid, [16200-53-6] (Aldrich); 9-Fluoreneacetic acid, [6284-80-6] (Aldrich); cis-Decahydro-1-naphthol,

[36159-47-4] (Aldrich); 9-Ethyl-bicyclo[3.3.1]nonane-9-ol, [21915-33-3] (Aldrich); 3-Quinuclidinol, [1619-34-7] (Aldrich); [[(1S)-endo]-(−)-Borneol, [464-45-9] (Aldrich); (1R, 2R,3R,5S)-(−)-Isopinocampheol, [25465-65-0] (Aldrich); Dehydroabietylamine [1446-61-3] (Aldrich); (±)-3-Aminoquinuclidine [6530-09-2] (Aldrich); (R)-(+)-Bornylamine, [32511-34-5] (Aldrich); 1,3,3-Trimethyl-6-aza-bicylo[3.2.1] octane [53460-46-1] (Aldrich); 1-Adamantylamine, [768-94-5] (Aldrich); 9-Aminofluorene, [5978-75-6] (Aldrich); (1R)-(−)-10-Camphorsulfonic acid, [35963-20-3] (Aldrich); 5-Isoquinolinesulfonic acid, [27655-40-9] (Aldrich); 2-Quinolinethiol, [2637-37-8] (Aldrich); 8-Mercaptomenthone, [38462-22-5] (Aldrich).

N-terminal modifications to provide peptides in accordance with the invention will therefore typically comprise a bulky and lipophilic group R which may be attached directly to the N-terminal amine to form a mono-, di- and possibly cationic trialkylated N-terminal amine. Alternatively, the R group may be attached via a linking moiety e.g. a carbonyl group (RCO) e.g. adamantyl or benzyl, carbamate (ROCO) e.g. Fmoc, or a linker which forms urea (RNHCO) or (R₂NCO) or by a linker which forms a sulfonamide, boronamide or phosphonamide. Sulfonamide forming linkers may be particularly useful when a more stable peptide is required. The bulky and lipophilic group R comprises a preferably saturated cyclic group, more preferably a polycyclic group wherein the cyclic groups are fused or bridged.

Peptides incorporating such N-terminal modifications are particularly effective as anti-tumor peptides and surprisingly, the presence of a cyclic, preferably multi-cyclic, N-terminal group provides peptides with an ability to kill tumor cells e.g. Meth A cells (from a fibrosarcoma) but have little cytotoxic activity against normal cells e.g. red blood cells or normal fibroblast cells. This selectivity is, of course, highly desirable in the in vivo treatment of established tumors. For example, cyclohexyl-LFB 17-31 at a concentration of 46 µg/ml killed 50% of Meth A cells (murine sarcoma cell line) but did not kill 50% of red blood cells of fibroblasts even at a concentration of 1000 µg/ml.

Thus, according to a further aspect of the invention is provided a cytotoxic 7 to 25 mer peptide with three or more cationic residues, which is optionally capable of forming an amphipathic α-helix and whose N-terminus is modified by a cyclic group comprising 5 preferably 6 or more non-hydrogen atoms, as well as esters, amides, salts and cyclic derivatives thereof. Pharmaceutical compositions containing such modified peptides together with a pharmaceutically acceptable diluent or carrier and such peptides for use in methods of treatment, particularly in the treatment or prevention of bacterial infections or as an anti-tumor agent (both in the destruction or reduction in size or number of benign or malignant tumors which may be ascites and in the prevention of metastasis) constitute further aspects of the present invention.

Particularly effective C-terminal modifications according to the present invention have also been investigated. Amidation of the C-terminus in order to manipulate the overall charge of a peptide is known but it has now been found that larger C-terminal modifications, including the formation of esters, including thioesters or substituted primary and secondary amides result in peptides with enhanced cytotoxic activity. The C-terminal modifying groups will advantageously contain more than 4, preferably 6, more preferably 8 or 10 or more non-hydrogen atoms and form e.g. a benzyl ester or amide. Other C-terminal groups include naphthylamine, substituted aromatic amines such as phenyl-ethylamine, mono, di- or tri-amino alkyl groups etc., groups incorporating a cyclic group being preferred. Standard C-terminal protecting groups are also suitable as activity enhancing modifications.

C-terminal modifications to provide peptides in accordance with the invention will therefore typically comprise a bulky and lipophilic group R which may be attached directly to the C-terminal carboxy group to form a ketone. Alternatively, the R group may be attached via a linking moiety, e.g. (OR) which forms an ester at the C-terminus, (NH—R) or (NR₂, wherein the two R groups needs not be the same) which form primary and secondary amide groups respectively at the C-terminus or groups (B—(OR)₂) which form boronic esters or phosphorous analogs. The bulky and lipophilic group R preferably comprises at least 4 non-hydrogen atoms.

Thus, according to a further aspect of the invention is provided a cytotoxic 7 to 25 mer peptide with three or more cationic residues, which is optionally capable of forming an amphipathic α-helix and whose C-terminus is modified by an organic group comprising at least 4 non-hydrogen atoms, as well as salts and cyclic derivatives thereof. Pharmaceutical compositions containing such modified peptides together with a pharmaceutically acceptable diluent or carrier and such peptides for use in methods of treatment, particularly in the treatment or prevention of bacterial infections or as an anti-tumor agent (both in the destruction or reduction in size or number of benign or malignant tumors which may be ascites and in the prevention of metastasis) constitute further aspects of the present invention.

Typically, the peptides of this aspect of the invention can be represented by the following formula:

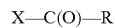

X—C(O)—R wherein X=a peptide of 7-25 amino acids in length incorporating 3 cationic residues;

R=OR¹, SR¹ or R¹; and

R¹=alkyl, cycloalkyl, aminoalkyl or aryl optionally substituted by hydroxy, alkoxy, acyloxy, alkoxycarbonyloxy, amino, oxo or fluoro groups and optionally interrupted by oxygen, nitrogen, sulphur or phosphorous atoms.

The substituted R¹ groups may be mono or polysubstituted. The term "acyl" as used herein includes both carboxylate and carbonate groups.

As used herein, the term "alkyl" includes a long or short chain straight-chained or branched aliphatic saturated or unsaturated hydrocarbon group. R¹ may contain up to 40 non-hydrogen atoms, preferably between 4 and 12, more preferably 6 to 10 such atoms.

Peptides according to the invention may comprise a non-genetic bulky and lipophilic amino acid as well as an N- and/or C-terminal modifying group as defined herein. Peptides may include all three types of bulky and lipophilic groups but will preferably comprise two such groups.

A still further aspect of the present invention is a method of preparing a peptide having enhanced cytotoxic activity and/or improved selectivity for target cell types which comprises incorporating a non-genetic bulky and lipophilic amino acid into a 7 to 25 mer peptide with three or more cationic residues which is optionally capable of forming an amphipathic α-helix.

Thus, the invention also provides a method of enhancing the cytotoxicity or selectivity of a 7 to 25 mer peptide with three or more cationic residues by incorporating therein a non-genetic bulky and lipophilic amino acid.

A definition of non-genetic bulky and lipophilic amino acid is provided hereinbefore. As previously discussed "incorporating" may include modification of an existing residue or introduction of such a residue into the peptide by addition or substitution, preferably substitution. A synthetic method may be used whereby the non-genetic bulky and lipophilic amino acid is included in sequence in the growing peptide so no post peptide formation processing is required.

When, herein, we refer to a peptide having "enhanced" cytotoxic activity, it is meant that the peptide which has been modified in accordance with the invention has enhanced cytotoxicity against one or more strains of bacteria or types of cancerous cells as compared to the peptide without said modification. By "improved selectivity for target cell types" is meant that the ratio of cytotoxic activity against target cells as compared to non target cell types is increased. In other words, selectivity can be improved if, for example, the antibacterial activity of a peptide is the same before and after modification but the hemolytic activity is decreased after modification. Similarly, useful peptides according to the invention may be made even when hemolytic activity increases, if the antibacterial or antitumoral activity increases by a greater amount. Selectivity may also refer to one type of bacteria over another.

As described above, particularly active and useful peptides have been prepared by incorporation of a non-genetic bulky and lipophilic amino acid. It has also been found that increasing the bulk and lipophilicity of a peptide by incorporation of one or more additional "genetic" bulky and lipophilic amino acids as previously defined may enhance activity. In particular, tryptophan rich analogs of peptides known to exhibit some cytotoxic activity have been shown to be effective as antimicrobial agents. Such analogs preferably have one or two tryptophan residues replacing other, non-essential residues.

Thus, in a further aspect of the present invention is provided a cytotoxic 7 to 25 mer peptide, with three or more cationic residues which is optionally capable of forming an amphipathic α-helix and which has at least a 40% sequence homology with a known or natural cytotoxic peptide and one or more extra genetic bulky and lipophilic amino acids (e.g. tryptophan), as well as esters, amides, salts and cyclic derivatives thereof.

The % homology is preferably 50 or 60% or more, particularly 70 or 80% or more. For the purposes of the present invention, the term "sequence homology" is not used to refer to sequence identity but to the presence of either the same amino acid or one from the same functional group. Suitable groupings for the standard amino acids are discussed above.

Sequence homology for such short peptides of the invention can most simply be calculated by comparing the two sequences, residue for residue, to determine whether the two amino acids at positions 1, 2, 3 etc. are the same or in the same group as previously defined. Thus, LFB (17-31)W3 has a 93.3% homology with LFB (17-31). Computer programs for calculating sequence homology are also known in the art and these may allow for additions (insertions) or deletions (gaps) in the sequence. Amino acid sequence homology may be determined using the BestFit program of the Genetics Computer Group (CGC) Version 10 Software package from the University of Wisconsin. The program uses the local homology algorithm of Smith and Waterman with the default values: Gap creation penalty=8, Gap extension penalty=2, Average match=2.912, Average mismatch=−2.003. Such a program could therefore be used to assess homology of the peptides of the invention with the native sequence, particularly if the modified peptide also incorporates gaps or insertions. Such a program is most suited to establishing the alignment between two sequences, again particularly when the modified sequence incorporates gaps or insertions.

For such peptides which comprise only genetically coded amino acids, similarity of the modified peptides with a known or natural cytotoxic peptide can be expressed by stringency of hybridisation of nucleic acid molecules encoding the two sequences rather than % homology. In this case, the ssDNA molecule encoding the modified peptide should hybridise with the ssDNA molecule complementary to the ssDNa molecule which encodes the known or natural cytotoxic peptide. Nucleic acid molecules encoding the peptides of the invention constitute further aspects of the present invention.

Sequences which "hybridise" are those sequences binding (hybridising) under non-stringent conditions (e.g. 6×SSC, 50% formamide at room temperature) and washed under conditions of low stringency (e.g. 2×SSC, room temperature, more preferably 2×SSC, 42° C.) or conditions of higher stringency (e.g. 2×SSC, 65° C.) (where SSC=0.15M NaCl, 0.015M sodium citrate, pH 7.2).

Preferably, the sequences will hybridise under conditions of higher stringency as defined above, or but for the degeneracy of the code, the sequences would hybridise under high stringency conditions.

Preferably, the peptides will include 1 or 2 additional genetic bulky and lipophilic amino acids and may otherwise be identical to the known cytotoxic peptide or incorporate only conservative substitutions.

In a further aspect, the invention provides a method of enhancing the cytotoxic activity of a peptide of 7 to 25 amino acids in length, which has three or more cationic residues and is optionally capable of forming an amphipathic α-helix which comprises introducing by addition or substitution, preferably substitution, a genetic bulky and lipophilic amino acid (e.g. tryptophan). By way of example, magainin derived peptides incorporating additional tryptophan residues and exhibiting enhanced activity are disclosed herein. Polynucleotides which encode these peptides of the invention constitute further aspects of the invention.

When the peptides of the invention incorporating a non-genetic bulky and lipophilic amino acid are derived from known or naturally occurring cytotoxic peptides or fragments thereof, they will preferably have the same degree of homology with the known or naturally occurring peptide as is discussed above.

Peptides, particularly those wherein the bulky and lipophilic R group as defined herein is a modified side chain of a 'genetic' amino acid, may be expressed in prokaryotic and eukaryotic hosts by expression systems well known to the man skilled in the art. Methods for the isolation and purification of e.g. microbially expressed peptides are also well known.

If a bacterial host is chosen for expression of a peptide, it may be necessary to take steps to protect the host from the expressed anti-bacterial peptide. Such techniques are known in the art and include the use of a bacterial strain which is resistant to the particular peptide being expressed or the expression of a fusion peptide with section at one or both ends which disable the antibiotic activity of the peptide; the fusion peptide can then be cleaved. In any event, the activity of the expressed peptide may be low, only enhanced to really cytotoxic levels by the post-synthetic modification to provide a peptide according to the invention e.g. addition of Pmc.

The peptides of the invention may be directly synthesised in any convenient way. Generally the reactive groups present (for example amino, thiol and/or carboxyl) will be protected during overall synthesis. The final step in the synthesis will thus be the deprotection of a protected derivative of the invention. As discussed above, certain peptides of the invention will carry a 'protecting group' as this is responsible for enhanced cytotoxicity.

In building up the peptide, one can in principle start either at the C-terminal or the N-terminal although the C-terminal starting procedure is preferred. The non-genetic amino acid can be incorporated at this stage as the sequence is extended or as a result of a post-synthetic modification.

Methods of peptide synthesis are well known in the art but for the present invention it may be particularly convenient to carry out the synthesis on a solid phase support, such supports being well known in the art.

A wide choice of protecting groups for amino acids are known and suitable amine protecting groups may include carbobenzoxy (also designated Z) t-butoxycarbonyl (also designated Boc), 4-methoxy-2,3,6-trimethylbenzene sulphonyl (Mtr) and 9-fluorenylmethoxy-carbonyl (also designated Fmoc). It will be appreciated that when the peptide is built up from the C-terminal end, an amine-protecting group will be present on the α-amino group of each new residue added and will need to be removed selectively prior to the next coupling step.

Carboxyl protecting groups which may, for example be employed include readily cleaved ester groups such as benzyl (Bzl), p-nitrobenzyl (ONb), pentachlorophenyl (OPC1P), pentafluorophenyl (OPfp) or t-butyl (OtBu) groups as well as the coupling groups on solid supports, for example methyl groups linked to polystyrene.

Thiol protecting groups include p-methoxybenzyl (Mob), trityl (Trt) and acetamidomethyl (Acm).

A wide range of procedures exists for removing amine- and carboxyl-protecting groups. These must, however, be consistent with the synthetic strategy employed. The side chain protecting groups must be stable to the conditions used to remove the temporary α-amino protecting group prior to the next coupling step.

Amine protecting groups such as Boc and carboxyl protecting groups such as tBu may be removed simultaneously by acid treatment, for example with trifluoroacetic acid. Thiol protecting groups such as Trt may be removed selectively using an oxidation agent such as iodine.

Peptides according to the invention may be prepared by incomplete deprotection to leave groups which enhance the cytotoxic activity of the peptides. Alternatively, modified R and N- and C-terminal groups may be prepared after synthesis of the peptide and associated deprotection.

A particularly preferred method involves synthesis using amino acid derivatives of the following formula: Fmoc-amino acid-Opfp.

The present invention also provides pharmaceutical compositions containing the peptides of the invention as defined above together with a physiologically acceptable diluent, carrier or excipient. Suitable diluents, excipients and carriers are known to the skilled man. The peptides of the invention for use in methods of treatment particularly in the treatment or prevention of bacterial infections or as an anti-tumor agent, both in the destruction or reduction in size or number of benign or malignant tumors which may be ascites and in the prevention of metastasis) constitute further aspects of the present invention.

The compositions according to the invention may be presented, for example, in a form suitable for oral, nasal, parenteral, intravenal, intratumoral or rectal administration.

As used herein, the term "pharmaceutical" includes veterinary applications of the invention.

By the term "effective amount", or "therapeutically effective amount," as used herein, is meant an amount that when administered to a mammal, preferably a human, mediates a detectable therapeutic response compared to the response detected in the absence of the compound. A therapeutic response, such as, but not limited to, increased overall survival, inhibition of and/or decreased tumor growth (including tumor size stasis), tumor size, metastasis, and the like, can be readily assessed by a plethora of art-recognized methods, including, e.g., such methods as disclosed herein.

The skilled artisan would understand that the effective amount of the lytic compound or vaccine composition administered herein varies and can be readily determined based on a number of factors such as the disease or condition being treated, the stage of the disease, the age and health and physical condition of the mammal being treated, the severity of the disease, the particular compound, composition or vaccine composition being administered, and the like.

The compounds according to the invention may be presented in the conventional pharmacological forms of administration, such as tablets, coated tablets, nasal sprays, solutions, emulsions, liposomes, powders, capsules or sustained release forms. The peptides of the invention are particularly suitable for topical administration, e.g. in the treatment of diabetic ulcers. Conventional pharmaceutical excipients as well as the usual methods of production may be employed for the preparation of these forms. Tablets may be produced, for example, by mixing the active ingredient or ingredients with known excipients, such as for example with diluents, such as calcium carbonate, calcium phosphate or lactose, disintegrants such as corn starch or alginic acid, binders such as starch or gelatin, lubricants such as magnesium stearate or talcum, and/or agents for obtaining sustained release, such as carboxypolymethylene, carboxymethyl cellulose, cellulose acetate phthalate, or polyvinylacetate.

The tablets may if desired consist of several layers. Coated tablets may be produced by coating cores, obtained in a similar manner to the tablets, with agents commonly used for tablet coatings, for example, polyvinyl pyrrolidone or shellac, gum arabic, talcum, titanium dioxide or sugar. In order to obtain sustained release or to avoid incompatibilities, the core may consist of several layers too. The tablet-coat may also consist of several layers in order to obtain sustained release, in which case the excipients mentioned above for tablets may be used.

Organ specific carrier systems may also be used.

Injection solutions may, for example, be produced in the conventional manner, such as by the addition of preservation agents, such as p-hydroxybenzoates, or stabilizers, such as EDTA. The solutions are then filled into injection vials or ampoules.

Nasal sprays which are a preferred method of administration may be formulated similarly in aqueous solution and packed into spray containers either with an aerosol propellant or provided with means for manual compression. Capsules containing one or several active ingredients may be produced, for example, by mixing the active ingredients with inert carriers, such as lactose or sorbitol, and filling the mixture into gelatin capsules.

Suitable suppositories may, for example, be produced by mixing the active ingredient or active ingredient combinations with the conventional carriers envisaged for this purpose, such as natural fats or polyethyleneglycol or derivatives thereof.

Dosage units containing the compounds of this invention preferably contain 0.1-10 mg, for example 1-5 mg of the peptides of the invention. The pharmaceutical compositions may additionally comprise further active ingredients, including other cytotoxic agents such as other antimicrobial peptides. Other active ingredients may include different types of antibiotics, cytokines e.g. IFN-γ, TNF, CSF and growth factors, immunomodulators, chemotherapeutics e.g. cisplatin or antibodies.

A yet further aspect of the present invention provides the therapeutic use of the peptides of the invention as defined above i.e. the peptides for use as medicaments, e.g. antibacterions or antitumoral agents. Further aspects comprise a method of treating or preventing bacterial infections in a patient comprising the administration to said patient of one or more of the peptides of the invention and a method of treating tumors in a patient comprising the administration of one or more of the peptides of the invention. The treatment of tumors includes the destruction or reduction in size or number of benign or malignant tumors which may be ascites and the prevention of metastasis.

The compounds and compositions of the invention may be administered alone or in combination as a method of treatment. Such combination therapies embrace the administration of the therapeutic agents as described herein in further combination with other biologically active ingredients (such as, but not limited to, a second and different antineoplastic agent, a dendritic vaccine or other tumor vaccine) and non-drug therapies (such as, but not limited to, surgery or radiation treatment or both). Therefore, the compounds and compositions of the invention may be administered in a therapeutic regimen comprising administering to the patient simultaneously, semi-simultaneously, separately or sequentially a therapeutically effective amount of a compound or composition of the invention with one or more other biologically active agents and non-drug therapies.

A still further aspect of the present invention comprises the use of one or more of the peptides of the invention in the manufacture of a medicament for treating bacterial infections or tumors.

Anti-bacterial agents such as the peptides of the present invention have a wide variety of applications other than as pharmaceuticals. They can be used, for example, as sterilizing agents for materials susceptible to microbial contamination. The peptides of the invention exhibit broad antimicrobial and antibiotic activity and thus are also suitable as anti-viral and anti-fungal agents which will have pharmaceutical and agricultural applications and as promoters of wound healing or spermicides. All of these uses constitute further aspects of the invention.

The peptides, when used in topical compositions, are generally present in an amount of at least 0.1%, by weight. In most cases, it is not necessary to employ the peptide in an amount greater than 1.0%, by weight.

Anti-tumor peptides may be administered in combination, possibly in synergistic combination with other active agents or forms of therapy, for example administration of a peptide according to the invention may be combined with chemotherapy, immunotherapy, surgery, radiation therapy or with the administration of other anti-tumor peptides.

In employing such compositions systemically (intra-muscular, intravenous, intraperitoneal), the active peptide is present in an amount to achieve a serum level of the peptide of at least about 5 ug/ml. In general, the serum level of peptide need not exceed 500 ug/ml. A preferred serum level is about 100 ug/ml. Such serum levels may be achieved by incorporating the peptide in a composition to be administered systemically at a dose of from 1 to about 10 mg/kg. In general, the peptide(s) need not be administered at a dose exceeding 100 mg/kg.

Those peptides exemplified herein represent preferred peptides according to the invention. Any peptide whose specific sequence is disclosed herein, particularly those peptides which are more active against bacterial cells than LFB 17-31, constitute a further aspect of the present invention.

Some of the preferred non-genetic bulky and lipophilic amino acids incorporated into the peptides of the invention include substituted tryptophans which provide an increase in bulk and lipophilicity and a significant increase in bioactivity. Substitutions have been made at the 1-position (or the indole N-position) and the adjacent 2-position and these new compounds, described in Example 2 constitute a still further aspect of the present invention. New 1-substituted tryptophans include 1-benzyl and 1-tosyl tryptophan.

The following novel, 2-substituted Tryptophan residues have been made, Z-Trp (2-nitrophenylsulfenylchloride)-OH and oxides thereof and Z-Trp(2-Pmc)-OH wherein Z is a protecting group, e.g. Fmoc. Method II of Example 2E is a newly devised synthetic route suitable for the preparation of a range of 2-sulfones and constitutes a further aspect of the present invention. Therefore, we further provide a method of preparing tryptophan residues substituted at the 2-position of the indole ring which comprises transferring the group with which the tryptophan will be substituted from a guanidyl containing group to an N-protected tryptophan. Preferably the guanidyl containing group is an arylalkyl or alkyl guanidyl group, most preferably it is a phenylethylguanidyl group. Preferably the N-protecting group is Fmoc and preferably the tryptophan substituting group is Pmc.

LFB 17-41 whose cysteine residues have been blocked by pyridylethylation or acetamido-methylation but incorporate no further bulky and lipophilic amino acids are not per se peptides of the invention. However pharmaceutical compositions comprising these peptides as well as use of the peptides as therapeutic agents as herein described constitute further aspects of the present invention.

In a further aspect, the present invention relates to a method of treating neoplastic tissue. In particular, it relates to a method of inducing inflammation through the lysis of tumor cells by the use of lytic compounds such as peptides. By triggering an inflammatory response, pathways of the innate and adaptive immune system are activated, facilitating a tumor-specific immune response. Such a triggering of the immune system confers on the subject adaptive immunity against the respective tumor cells thereby inhibiting growth of secondary tumors.

The uncontrolled growth and division of cells may give rise to tumors. Tumours are typically classed as either benign or malignant, based on the criteria of spread and invasion. Malignant tumors are capable of invading and destroying surrounding tissues. Their cells may also spread beyond the original site of the tumor. Benign tumors do not possess these characteristics, but benign tumors may progress to a malignant stage, so it may be useful to treat benign tumors as well as malignant ones. For example, in oral squamous carcinoma neoplasia is not usually treated, but this condition can rapidly progress into a malignant stage where parts or the whole tongue has to be surgically removed.

Moreover, benign tumors may still be per se undesirable, particularly if they are large and grow adjacent to vital organs, and so treatment of a benign tumor which thereby reduces subsequent similar benign tumors would also be desirable.

The process by which cells from a malignant tumor break away from the primary tumor and spread to other organs in the body by travelling in the bloodstream or lymphatic system is called metastasis. When these cells reach a new area of the body they may invade tissue and go on dividing and may form a new tumor. Such a new tumor is often referred to as a "secondary tumor".

The growth of secondary tumors usually poses a threat to the health of the subject and there is therefore a need to develop ways to inhibit the formation or growth of secondary tumors.

Resection of advanced solid tumors is often inefficient in the long term due to the persistence of tumor cells and subsequent growth of previously undetectable micrometastasis. Among breast cancer patients this remains a major cause of recurrence and ultimate death. After surgery the disseminated cells often rest in the G0 phase of the cell cycle. Such non-proliferating cells are therefore often resistant to chemotherapy. The cure-rates for advanced head and neck cancer patients has not improved significantly in the last decade. Most cases of recurrence in these patients are local or regional, and present in such a way as to make them difficult to access. An example is locally advanced esophageal cancers which are often inoperable with a poor prognosis.

A great hurdle in the search for a way to inhibit growth of secondary tumors is that tumors form from cells which originate from the subject's own body. The immune system struggles to recognise them as abnormal. Recognition of foreign or abnormal cells typically involves the detection of molecules located at the cell surface, antigens. Most tumor cells possess at least one kind of antigen which distinguishes them from normal cells and in many cases the antigens are specific for a particular type of cancer. Some tumor cells may possess a variety of antigens, whilst others may only possess a single type of antigen. The type of antigen, the number of different antigens and the prominence of the antigens on the cell surface may all influence the chances that the immune system may recognise the tumor cells as abnormal. Many types of tumor possess very few antigens, or only antigens which are poorly recognised by the immune system as foreign and are thus capable of escaping recognition and destruction by the immune system. The type and quantity of antigens possessed by any particular tumor type thus plays a big part in determining how "immunogenic" a tumor is. By "immunogenic" is meant the ability to elicit an immune response, so the more immunogenic a tumor is, the more likely it is that it will be recognised and attacked by the immune system.

Various attempts have been made to help the immune system to fight tumors. One early approach involved a general stimulation of the immune system, e.g. through the administration of bacteria (live or killed) to elicit a general immune response which would also be directed against the tumor. This is also called nonspecific immunity.

More recent approaches aimed at helping the immune system specifically to recognise tumor-specific antigens involve administration of tumor-specific antigens, typically combined with an adjuvant (a substance which is known to cause or enhance an immune response) to the subject. This approach requires the in vitro isolation and/or synthesis of antigens, which is costly and time consuming. An alternative approach to reduce recurrence rates of different types of cancer is the use of immunotherapy. Most cancers present several challenges to the use of immunotherapy. Often not all the tumor-specific antigens have been identified, e.g. in breast cancer the known antigens are found in 20-30% of the total tumors. The use of tumor-specific vaccines have therefore met with limited success.

There remains a strong need for alternative methods for inhibiting the growth or formation of secondary tumors.

The present inventors have surprisingly found that a lytic compound may be used to lyse cells of a first tumor in a patient and thereby inhibit growth of further tumors in said patient. This effect has been demonstrated, as described herein in the Examples, using a lytic peptide. Other lytic compounds are known in the art and Examples include detergents such as Triton X-100 and acids such as HCl.

The use of lytic peptides for the treatment of tumors has been proposed in the art based on their ability to lyse tumor cells (Risso et al., Cell. Immunol. [1998] 107 and WO 01/19852). The finding that such lytic peptides may be used not only to treat a first tumor, but also to inhibit the growth of a second tumor was completely unexpected.

Without wishing to be bound by theory, it is suspected that lysis of the first tumor elicits an inflammatory response. The lysis may cause the exposure of antigens specific for the cancer cell. By "exposure" is meant that the antigen is made available to be recognised as foreign by the immune system.

Thus "exposure" includes making an antigen more readily accessible for the immune system and/or presenting it to the immune system in such a way that it is more likely to be recognised by the immune system, e.g. because it is on a cell fragment, rather than a whole cell. Thus, the term "exposure" includes the release of antigens from an intracellular space but also any other change in the cell structure which results in an antigen becoming more readily recognisable to the immune system.

The exposed antigen may activate specific B cells and/or T cells of the immune system and cause some of these to mature into memory cells. Memory cells typically have a very long life span and when they encounter the same antigen for a second or further time they are able to respond more readily than virgin B or T cells. This process of generating and maintaining specific memory cells is commonly referred to as an "immunological memory" or "adaptive immunity". Thus, the present inventors have surprisingly found that lytic agents such as peptides may be used to induce an immunological memory against tumors.

The present inventors have demonstrated that by successful treatment of a tumor with a lytic compound, growth of a second tumor is not observed. In a model experiment, adoptive transfer of spleen (immune) cells from an animal previously successfully treated (cured) with a lytic compound, was shown to confer specific immunity to the naïve acceptor individual. Thus, acceptors which received spleen cells from previously cured mice were able to eliminate implanted tumors, whereas acceptors which received spleen cells from naive mice were unable to eliminate implanted tumors. These results demonstrate that the protective effect is due to the previous successful tumor eradication conferring a long-term, specific immunity against further tumors, in particular further tumors of the same type.

Furthermore, tumors often induce general immune suppression and so the triggering of the immune system observed according to the present invention is highly advantageous.

Thus in one aspect, the present invention provides a method of inducing adaptive immunity in a subject, which comprises administration of an effective amount of a lytic compound to said subject wherein the lytic compound, through lysis of cells in a first tumor, generates an immune response which inhibits the growth or establishment of a second tumor.

At its simplest, the present invention provides a method of inducing adaptive immunity in a subject, which comprises administration of an effective amount of a lytic compound to said subject.

Adaptive immunity will be understood, in the present context, as immunity against tumor growth or establishment, in particular against tumors which are the same or similar to a tumor which has been directly targeted for lysis by said lytic compound. The lytic compound is therefore designed or selected to lyse tumor cells.

Alternatively viewed, the present invention provides a method of cancer treatment in a subject which comprises administration of an effective amount of a lytic compound to said subject, wherein the lytic compound, through lysis of cells in a first tumor, generates an immune response which inhibits the growth or establishment of a second tumor.

Viewed another way, the inventors have found that lytic compounds may be used in the treatment of a first tumor to generate a vaccine against a second tumor. The vaccine is generated in situ, i.e. the antigens which induce an immune response and create an immunological memory are presented to the immune system as a consequence of the lysis of the tumor cells. Such a vaccine where lytic compounds such as peptides are administered to a subject to generate antigens in situ (in vivo) represents a radical departure from the prior art, where antigens are typically prepared in the laboratory (i.e. in vitro) and are administered to the subject.

Thus in a further aspect the invention provides use of a lytic compound in the manufacture of a medicament for use as a vaccine against tumor growth or development. 'Growth and development' includes establishment of a tumor. The invention also provides a method of vaccinating a subject against tumor growth or development through administration of a lytic compound to said patient, preferably a lytic peptide. Reference to a 'vaccine' and 'vaccinating' both imply a prophylactic effect, thus while there may be beneficial direct treatment of existing tumors, a significant motivation is the prevention or reduction in future tumor establishment, growth or development.

Not wishing to be bound by any particular hypothesis, it is believed that the lytic event induces an inflammatory response that seems to be important in the eradication of the first tumor as well as inducing adaptive immunity protecting against one or more second tumors. This is illustrated by the inventors' findings that they would very often succeed in obtaining full regression of a first tumor in syngenic animal models (with intact immune systems), whereas in nude mice (without a functioning immune system), they have not been able to achieve more than 50% growth inhibition of a first tumor. Hence, it may be sufficient to lyse parts of a first tumor which may promote a directed immune response towards remaining cells of the tumor, as well as inducing a protective antitumor memory against secondary tumors.

Thus adaptive immunity against a tumor is generated in the subject, particularly against tumors which are of the same type or similar to the first, lysed, tumor.

The invention also provides the use of a lytic compound in the manufacture of a medicament for inducing adaptive immunity in a subject. In particular the invention provides the use of a lytic compound in the manufacture of a medicament for inducing adaptive immunity in a subject, wherein the lytic compound, through lysis of cells in a first tumor, generates an immune response which inhibits the growth or establishment of a second tumor.

The invention also provides a lytic compound for use in inducing adaptive immunity in a subject. More particularly the invention provides a lytic compound for use in inducing adaptive immunity in a subject, wherein the lytic compound, through lysis of cells in a first tumor, generates an immune response which inhibits the growth or establishment of a second tumor.

Thus, by a "first tumor" is meant the tumor which has been identified in the subject and which it is intended to treat by causing direct and immediate lysis thereof. The first tumor will typically be a primary tumor, i.e. the first tumor of its kind to develop and/or be identified in the subject. However, the "first tumor" may in fact be a secondary tumor. Such a situation may arise for example where a primary tumor was removed from the subject (surgically or otherwise). Thus by "first tumor" is not necessarily meant the first tumor to develop in the subject; the term "first" is used in relation to the sequence of events of the method of the present invention.

The lytic compounds will typically be administered locally to the first tumor, e.g. injected into the first tumor or in its immediate vicinity, although systemic delivery is also contemplated. Injection solutions may, for example, be produced in a conventional manner, such as by the addition of preservatives such as p-hydroxybenzoates, or stabilisers such as EDTA. The solutions are then filled into injection vials or ampoules.

An objective of the methods and uses of the present invention is to generate an immunological memory and thereby inhibit growth or establishment of a second tumor in a patient who has been subjected to lysis of a first tumor in their body. Inhibition of growth includes regression of the tumor, i.e. when it is reduced in size, preferably to the point where it disappears completely and/or is no longer detectable. Inhibition also includes the prevention of establishment of a second tumor. Thus effective treatments according to the present invention may mean that the patient never develops further detectable tumors after the initial lysis treatment of the first tumor. Inhibition of growth also includes a reduction in the normal rate of tumor growth, slowing or prevention of the establishment of a blood vessel network within the solid tumor.

The term "second tumor" typically refers to secondary tumors, also called metastases, i.e. a tumor which has developed from a cell which has originated from another tumor and has spread to a new site. However, within the scope of the present invention, the term "second tumor" may also include a primary tumor. This situation may arise where two or more tumors co-exist, for example two primary tumors which arose independently, or a primary and a secondary tumor and where a secondary tumor is treated directly with the lytic peptide to induce an immunological memory against that type of tumor, including the primary tumor.

The term "second" tumor includes literally the second and also any subsequent or further tumors. Thus several secondary tumors may have their growth inhibited according to the present invention. The "second" tumor may also be a tumor that has returned after initial treatment, possibly with conventional therapy (i.e. not necessarily through lysis).

The first tumor and the second tumor preferably have similar immunogenic properties, preferably the first tumor and the second tumor are of the same cancer type. It will be appreciated that within any given tumor not all cells may possess the same phenotype, so the individual cells of a tumor may possess different antigens. This may result in the exposure of a large variety of antigens upon lysis and may provide an immunological memory against a variety of cancer cell types.

Because of the induction of an immunological memory, discussed above, the "second tumor" may not yet exist in the subject or at least not be detectable at the time the lytic compound is administered. Because the primary lytic event has 'primed' the subject and stimulated the immune system it is appropriate to consider that an in situ cancer vaccine has been generated.

Throughout the text, any reference to the term "tumor" which is not preceeded by the desingation "first" or "second" is, unless the context clearly suggests otherwise, to be understood to apply both to the first and the second tumor.

References to "lysis" of a first tumor are to be understood to mean lysis of one or more cells of said tumor. Thus lysis of the entire tumor is not required. "Lysis" as used herein includes partial as well as complete lysis of a cell. By partial lysis is meant that the outer cell membrane is sufficiently destabilized to cause cellular components to leak out of the cell and/or to cause fractions of the outer membrane to become detached from the cell. The requirement for antigen presentation does not demand total disintegration of the tumor cells.

Preferably, the tumor is selected from the group consisting of lymphomas, carcinomas and sarcomas, most preferably B-cell lymphoma. Melanomas are also contemplated. In general, the tumors are naturally occurring, pathological tumors; as discussed above, benign tumors may be targeted.

A further preferred application of the present invention is in the treatment of benign tumors, e.g. of oral epithelia. Previously such tumors may not have been treated on first identification, instead subjected to "watch-and-wait". By treating such tumors at an earlier stage the process that might lead to malignant transformation can be stopped. Chemoresistant benign tumors are particularly suitable as targets.

The subject may be any human or non-human animal, preferably a mammal, more preferably a human.

By "lytic compound" is meant any compound which is capable of causing animal cells to lyse. Preferably, the lytic compound will have a reasonably high specificity for tumor cells, i.e. it will lyse tumor cells in preference to equivalent healthy cells, to minimize side effects experienced by the subject to which the compounds are administered.

The lytic compound is preferably a peptide. Suitable lytic peptides are known in the art and include for example those described in WO 00/12541, WO 00/12542, WO 01/19852 and WO 01/66147 as well as those described in the following documents: Papo N, Shahar M, Eisenbach L, Shai Y. "A novel lytic peptide composed of DL-amino acids selectively kills cancer cells in culture and in mice". *J Biol Chem* 2003; 278(23):21028-23; Papo N, Braunstein A, Eshhar Z, Shai Y. Suppression of human prostate tumor growth in mice by a cytolytic D-, L-amino Acid Peptide: membrane lysis, increased necrosis, and inhibition of prostate-specific antigen secretion. *Cancer Res* 2004; 64(16):5779-86; Leuschner C, Hansel W. Membrane disrupting lytic peptides for cancer treatments. *Curr Pharm Des* 2004; 10(19):2299-310; Johnstone S A, Gelmon K, Mayer L D, Hancock R E, Bally M B. In vitro characterization of the anticancer activity of membrane-active cationic peptides. I. Peptide-mediated cytotoxicity and peptide-enhanced cytotoxic activity of doxorubicin against wild-type and p-glycoprotein over-expressing tumor cell lines. *Anticancer Drug Des.* 2000; 15:151-60; and Selsted M E, Novotny M J, Morris W L, Tang Y Q, Smith W, Cullor J S. Indolicidin, a novel bactericidal tridecapeptide amide from neutrophils. *J Biol Chem* 1992; 267(7):4292-5.

Lytic peptides are particularly preferred as lytic agents. Typically they have a short half-life, i.e. they generally degrade rapidly after lysing the cells, e.g. due to the release of proteases and the like from the cells. A short half-life lowers the risk of systemic toxicity and so may be advantageous, but a longer half life may be desirable in some cases. The half-life of peptides may be manipulated, i.e. increased or decreased if desired. For example, the half-life of the peptide may be extended by introducing D-amino acids and/or modifying the C-terminal and/or N-terminal end.

A further class of preferred lytic compounds are peptidomimetics of known or predicted lytic peptides.

It is now commonplace in the art to replace peptide or protein-based active agents, e.g. therapeutic peptides, with such peptidomimetics having functionally-equivalent activity. Generally such compounds will simply replace the (—C(R)CONH—)$_n$ backbone of the peptide with an alternative flexible linear backbone, e.g. a (—C(R)NHCO—)$_n$ or (—C(R)CH$_2$CH$_2$)—$_n$, or a non-linear backbone (e.g. one based on a string of fused cyclohexane rings). Despite the change in the backbone, the pendant functional groups (the side chains in the peptide original) are presented in a similar fashion allowing the compound to possess similar lytic activity.

Various molecular libraries and combinatorial chemistry techniques exist and are available to facilitate the identification, selection and/or synthesis of such compounds using standard techniques (Kieber-Emons, T. et al. Current Opinion in Biotechnology 1997 8: 435-441).

The peptides will typically be at least 3 amino acids in length, e.g. 4-30, preferably 5-30 amino acids in length, preferably 7-25 amino acids in length and will incorporate one or more, preferably 2-8, more preferably 4-8, positive charges. Preferably the peptides will include groups which are bulky, e.g. 4 or more, more preferably 7 or more, non-hydrogen atoms and lipophilic, these groups are thought to interact with the cell membrane and contribute to lysis, preferably the peptides will have 2-6 of such groups. In a preferred embodiment the lytic peptide contains at least one biphenylalamine (Bip) and/or at least one diphenylalamine (Dip) residue. Further preferred peptides incorporate 1-5, e.g. 2-4, tryptophan residues.

The lytic peptide may be a lactoferrin derived peptide, it may be cyclic LFB (the primary sequence of which is FKCR-RWQWRMKKLGAPSITCVRRAF (SEQ ID NO: 6)).

A preferred group of molecules for use in this aspect of the invention are cytotoxic 7-25 mer peptides with three or more cationic residues which have one or more non-genetic bulky and lipophilic amino acids, as well as esters, amides, salts and cyclic derivatives thereof. Such molecules are described in more detail in the specification. 'Non genetic' amino acids do not include D forms of genetically coded amino acids.

The use of esters, amides or cyclic derivatives of peptides or peptidomimetics, in particular of those peptides mentioned above, is also contemplated by the present invention. The lytic peptide or peptidomimetic (or ester, amide or cyclic derivative thereof) may be used in its free form or e.g. as a conjugate or a salt. The salt will preferably be a pharmaceutically acceptable salt, e.g. acetate. In a preferred embodiment, the lytic peptide or peptidomimetic is present as a trifluoroacetate (TFA) salt. Trifluoroacetate is frequently used in chromatographic techniques used to purify peptides after peptide synthesis.

Lytic agents which are not peptides will preferably be delivered intratumorally. Lytic peptides may be delivered in this way but may also be delivered systemically due to their selectivity for tumor cells as compared to healthy cells of the same tissue type. Lytic peptides which are highly selective in this way are preferred. All lytic agents may be targeted to the site of the first tumor in other ways, e.g. using liposome delivery, dextrin-conjugation, or other suitable carrier solutions. Thus systemic delivery is also possible with non-peptide lytic agents.

The lytic compound itself is preferably only weakly immunogenic, more preferably it is not immunogenic at all, i.e. it does not by itself induce an antibody response.

BRIEF DESCRIPTION OF THE FIGURES

FIG. 1 shows the amino acid sequence and charge at pH 7 for synthetic lactoferricins from different species (SEQ ID Nos: 7-18, respectively);

Figure 2:
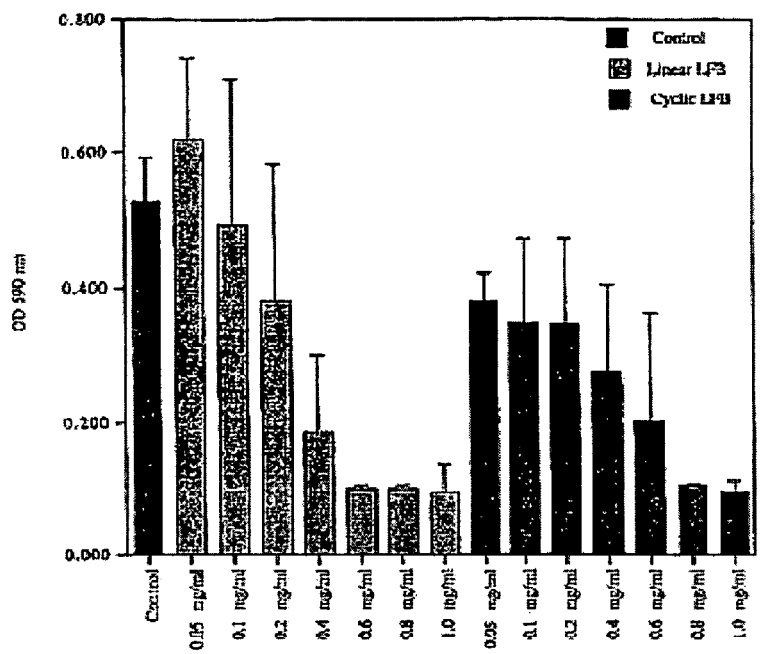
FIG. 2 shows the effects of linear and cyclic lactoferricin B on a Meth A fibrosarcoma cell line in vitro after 24 hours incubation.

The invention will now be described with reference to the following non-limiting examples.

EXAMPLE 1

Human, Bovine, Murine and Caprine Lactoferrin Derived Peptides

A) MIC (Minimum Inhibitory Concentration) Tests

The bacterial strains used were: *Escherichia coli* ATCC 25922 and *Staphylococcus aureus* ATCC 25923. All strains were stored at −70° C. The bacteria were grown in 2% Bacto Peptone water (Difco 1807-17-4). All tests were performed with bacteria in mid-logarithmic growth phase. Determination of the minimum inhibitory concentration (MIC) of the peptides for bacterial strains were performed in 1% Bacto Peptone water. A standard microdilution technique with an inoculum of $2\times10^6$ CFU/ml was used. All assays were performed in triplets. Since the peptides are positively charged and therefore could adhere to the plastic wells, we controlled the actual concentration of the peptides in the solution by HPLC. There was no difference between the concentration of the peptides before or after adding the solution to the plastic wells.

B) Synthesis of Peptides

Initially, the lactoferricin B used was a gift from Wayne Bellamy (Nutritional Science Laboratory, Morinaga Milk Industry Co. Ltd, Japan). Later in the study the peptides were synthesised with a 9050 Plus PepSynthesizer (Milligen). All peptides were synthesised on solid phase by use of fluorenyl-methoxycarbonyl (Fmoc) chemistry. Cysteines in cystein containing peptides were protected with acetamidomethyl groups to prevent disulfide bridge formation. The peptides were analysed and purified by reversed phase HPLC on a Waters 600E chromatograph (Millipore) with UV detection at 254 nm. The fractions purified on HPLC were analysed on a liquid chromatography-mass spectrometer (LC-MS) with electrospray interface (Fisons VG Quattro) or/and with Fast Atom Bombardment Mass Spectrometry (FAB-MS) (Fisons VG Tribrid).

Structure of the Lactoferricins

The structure of human lactoferrin is determined to 2.8 and 2.2 Å resolution by X-ray crystallography. Human lactoferricin (LFH) consists of residues 1-47 of human lactoferricin. LFH contains two peptide fragments; one consisting of residues 12-47 cyclised with a disulfide bridge between Cys20 and Cys37, the second fragment (residues 1-11) is connected to the 12-47 fragment through a disulfide bridge between Cys10 and Cys46. In the human lactoferrin structure, the corresponding residues comprises a β-strand (residues 4-11), an α-helix (residues 12-29), a turn (residues 30 and 31), followed by a β-strand (residues 31-47) [Day, C. L., Anderson, B. F., Tweedie, J. W. and Baker, E. N. (1993) J. Mol. Biol. 232, 1084-1100]. Bovine lactoferricin (LFB) with only 25 residues (residues 17-41) in a single chain is structurally much simpler than LFH.

Antibiotic Activity of Synthetic Lactoferricins with Sequences from Different Species The amino acid sequence of lactoferrins from goat [Provost, F. L., Nocart, M., Guerin, G. and Martin, P. (1994) Biochem. Biophys. Res. Commun. 203, 1324-1332] and mouse [Pentecost, B. T. and Teng, C. T. (1987) J. Biol. Chem. 262 10134-10139] have been determined and show high sequence homology with both the human and the bovine lactoferrins. The residues engaged in the helix-turn-strand motif can easily be identified in the sequence as shown in FIG. 1. As LFB is more antibacterial than LFH, the residues corresponding to LFB (17-41) were chosen in the amino acid sequence of human, murine and caprine lactoferrin to prepare analogous lactoferricin peptides; LFH (18-42), LFM (17-41) and LFC (17-41) respectively. The disulfide bridge is not essential for antibiotic activity in bovine and human lactoferricin [Bellamy et al. (1992)] and all peptides were prepared with ACM protection of the cysteine residues to avoid cyclisation or oxidation.

The antibacterial activities of the synthetic lactoferricins expressed as MIC are compiled in Table 1 which shows that LFB (17-41) displayed the most significant antibacterial activity against *E. coli* and *S. Aureus*.

TABLE 1

Minimum inhibitory concentration (MIC) in μg/ml (μM) of synthetic lactoferricins on *E. coli* ATCC 25922 and *S. aureus* ATCC 25923.

| Peptide | *E. coli* ATCC 25922 MIC | *S. aureus* ATCC 25923 MIC |
| --- | --- | --- |
| LFH (18-42) | >200 | >200 |
| LFB (17-41) | 30 | 30 |
| LFM (17-41) | >200 | >200 |
| LFC (17-31) | 750 | 1000 |
| LFB (14-31) | 70 (28) | 200 (80) |
| LFB (17-31) | 40 (20) | 100 (50) |
| LFB (18-31) | 80 (43) | 200 (108) |
| LFB (19-31) | 200 (120) | >250 (150) |
| LFB (20-31) | 100 (62) | 200 (124) |
| LFB (17-31) K17 | 60 (30) | 100 (50) |
| LFB (17-31) F20 | 20 (10) | 200 (100) |
| LFB (17-31) K17, F20 | 20 (10) | 200 (100) |

LFB Analogs with Different Chain Length

A property considered to be important in determining the antibacterial activity of linear peptides, is their ability to adopt helical structures. In the intact lactoferrin protein, residues 14-28 are located in an α-helix, residues 29-31 comprise a turn and residues 32-41 are in a β-strand. We therefore anticipated that the antibacterial effect of the lactoferricins could originate from the part of the sequence that participates in the helix of the intact protein. As the bovine lactoferricin sequence, LFB (17-41), was the only peptide with significant antibacterial property, we chose to prepare a shorter variety of the bovine peptide, LFB (17-31), containing both the helix and turn residues of the protein, while the 10 residues encompassing the strand were removed. Despite the fact that LFB (17-31) has a lower net charge (FIG. 1) than LFB (17-41) and LFC (17-41), it still retains most of the antibacterial effect as shown in Table 1. These findings indicate that even if the overall charge is important, it is not sufficient for antibacterial activity.

EXAMPLE 2

Preparation of Novel Substituted Tryptophans

In the following Examples and throughout the text the following general formula: Z—XX(n–y)-OH refers to a substituted amino acid (XX) wherein the $NH_2$ group of the amino acid is Z-protected, the amino acid is y-substituted at the n position and the COOH group of the amino acid is free.

A) Preparation of Ac-Trp(1-Tos)-OH

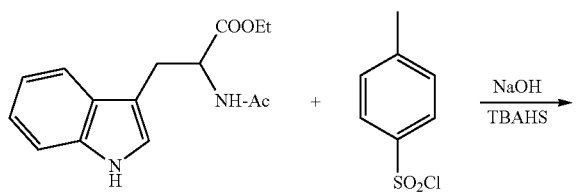

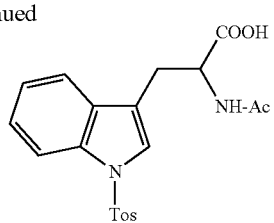

Experimental:

A mixture of Ac-Trp-OEt (0.19 g, 0.69 mmol), tosyl chloride (0.20 g, 1.04 mmol), tetrabutylammonium hydrogensulfate (2 mg, 0.01 equiv.) and NaOH (0.07 g, 1.73 mmol) in dichloromethane was stirred at room temperature for 2.5 hours. To the reaction mixture was added diluted HCl until a pH of 2-3 was reached and then washed with water. To the organic phase was added a diluted base and the aqueous phase was extracted with dichloromethane, acidified and again extracted with dichloromethane.

$^1$H NMR (CDCl$_3$): δ 1.89 (s, 3H), 2.24 (s, 3H), 3.1-3.35 (m, 2H), 4.87 (m, 1H), 6.63 (d, 1H), 7.1-7.3 (m, 4H), 7.46 (m, 2H), 7.68 (d, 2H), 7.89 (d, 1H), 9.34 (s, broad, 1H). MS (EI): m/z 382 (10%), 284 (84%), 157 (8%), 155 (61%), 130 (26%), 129 (24%).

Materials:

Ac-Trp-Oet was prepared according to procedure described under "Preparation of diacetyltryptophan ethyl ester", Bodanszky, M and Bodanszky A, The Practice of Peptide Synthesis (1994) p 30; Vogel's Textbook of Practical Organic Chemistry 5th Ed. (1989) p. 1273.

B) Preparation of Fmoc-Trp(1-Bentyl)-OH

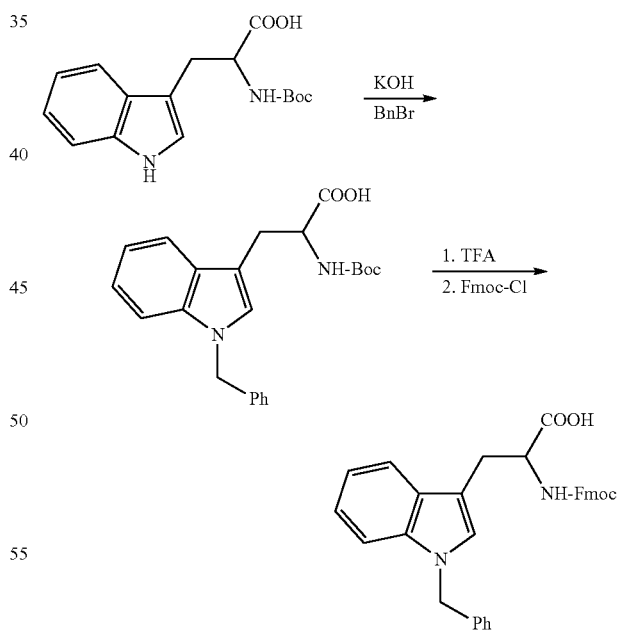

Boc-Trp(1-Benzyl)-OH[1]:

Dimethyl sulfoxide (7 ml) was added to potassium hydroxide (0.73 g, 13 mmol) (crushed pellets) and the mixture was stirred for 5 min. Boc-Trp-OH (1 g, 3.3 mmol) was then added and the mixture stirred for 1 hour. Benzyl bromide (1.13 g, 6.6 mmol) was added and the mixture cooled briefly and stirred for a further 20 hours before water (20 ml) was added. The mixture was extracted with diethyl ether (3×20 ml). The pH of the combined aqueous phases was adjusted to 2-3 by addition of 1M HCl (20 ml) and extracted with diethyl ether (3×20 ml). Each extract was washed with water (3×20 ml). The combined diethyl ether phases were dried with $MgSO_4$ and the solvent removed under reduced pressure. The product was isolated as white crystals (0.89 g, 2.3 mmol). Yield 69%.

$^1$H NMR ($CDCl_3$): δ 1.41 (s, 9H), 3.33 (m, 2H), 4.64 (m, 1H), 5.02 (m, 1H), 5.24 (s, 2H), 6.95 (s, 1H), 7.01-7.38 (m, 8H), 7.59 (d, J=7.7 Hz, 1H).

H-Trp(1-Benzyl)-OH:

Boc-Trp(1-Bn)-OH was dissolved in 98% TFA and stirred for 3 hours at room temperature. Then the solvent was removed under reduced pressure. The product was isolated as an oil and used without further purification.

Fmoc-Trp(1-Benzyl)-OH:

H-Trp(1-Bn)-OH (1.90 g, 6.5 mmol) was dissolved in a 10% solution of $Na_2CO_3$ in water (21 ml, 20 mmol). Dioxane (15 ml) was added and the mixture was stirred in an ice-water bath. 9-Fluorenylmethyl chlorocarbonate (1.69 g, 6.5 mmol) was added in small portions and stirring was continued at ice-water bath temperature for 4 hours and then at room temperature for 8 hours. The reaction mixture was poured into water (400 ml) and extracted with ether (3×200 ml). The combined ether phases were dried with $MgSO_4$ and the solvent removed under reduced pressure. The product was purified by chromatography on silica gel in solvent A (Solvent A=Ethylacetate:Methanol=4:1). After purification the product was obtained as a white crystalline compound. The yield was 2.42 g (72%).

$^1$H NMR (400 MHz, $CDCl_3$): δ 3.34 (m, 2H), 4.18 (m, 1H), 4.37 (m, 2H), 4.78 (s, 1H), 5.19 (s, 2H), 5.31 (d, 1H), 6.91-7.74 (m, 19H).

Materials:

| Boc-Trp-OH | BACHEM no A-2360 |
| Fmoc-ONSu | Fluka no 46920 |
| Trifluoroacetic acid | Fluka no 91700/KEBO no 1.8341-100 |

Reference 1: Heaney, H., and Ley, S. V. J. Chem. Soc. Perkin 1. (1973) 499-500

C) Preparation of Fmoc-Trp(2-Nps)-OH

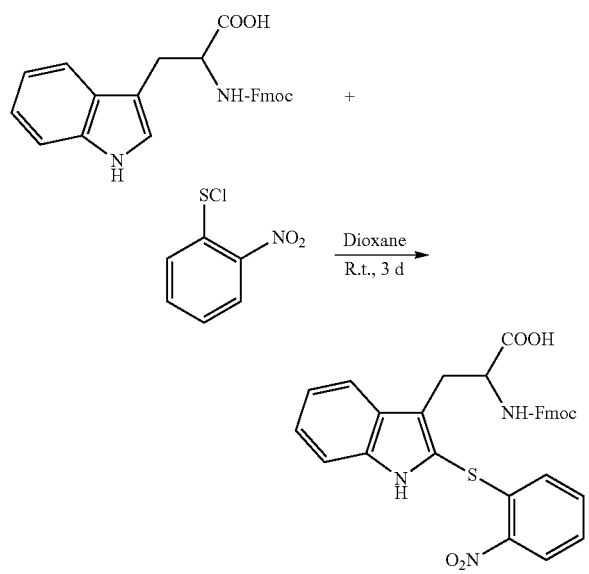

To a solution of 2.0 g (4.7 mmole) Fmoc-L-tryptophan in 12 ml dioxane, 0.87 g (4.6 mmole) of 2-nitrophenyl-sulfenyl-chloride (2-Nps-C1) in 25 ml dioxane was added under stirring at room temperature. After standing for 3 days, 50 ml ethyl ether was added to the reaction mixture and the solvent was evaporated. The product was purified by chromatography on silica gel in solvent A (Solvent A=Chloroform:Ethanol:Neptane—1:1:1). $R_f$ 0.43. After purification the product was obtained as a yellow-brown crystalline compound. The yield was 2.5 g (89%). HPLC(C18): $t_R$ 8.3 min, 85-100% B in 20 min. (A:$H_2O$+0.1% TFA; B:$CH_3CN$+0.1% TFA).

$^1$H NMR (DMSO-$d_6$): δ 3.16 (m, 1H), 3.38 (m, 1H), 4.00-4.10 (m, 3H), 4.19 (m, 1H), 6.72 (d, J=8.1 Hz, 1H), 7.03 (t, J=7.3 Hz, 1H), 7.18 (t, 1H), 7.22-7.49 (m, 7H), 7.60 (dd, J=7.3 and 12.1 Hz, 2H), 7.86 (m, 3H), 8.24 (d, J=8.1 Hz, 1H), 11.51 (s, 1H).

After incorporation of Fmoc-Trp(2-Nps)-OH into a peptide, MS electrospray analysis confirmed the expected molecular weight.

Materials:

| Fmoc-Trp-OH | BACHEM No B-1445/SENN No 02019 |
| 2-Nitrophenylsulfenyl chloride | Fluka No 73740 |

D) Oxidation of Fmoc-Trp(2-Nps)-OH

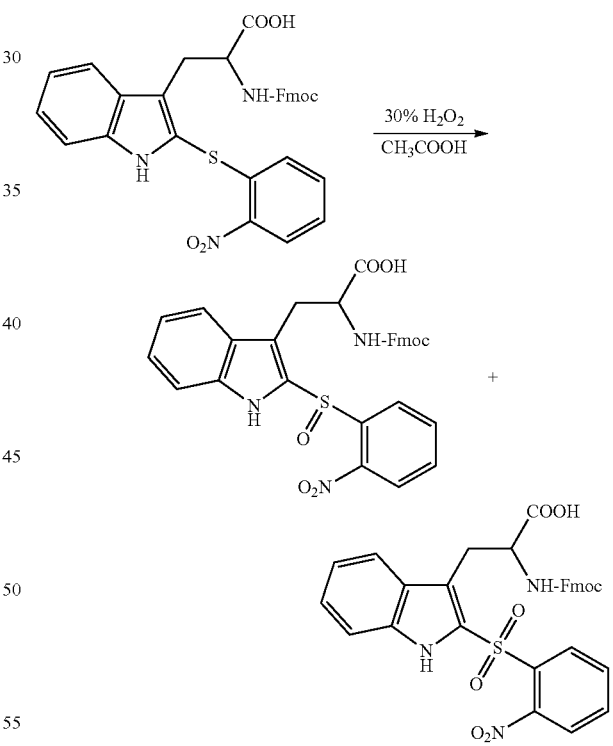

To a solution of 1.12 g (1.9 mmol) Fmoc-Trp(2-Nps)-OH in 15 ml glacial acetic acid, was added 12 ml 30% $H_2O_2$ under stirring at room temperature. The reaction mixture was heated for 2 hours at 65° C. The precipitate was collected, added water and lyophilised. The yield was 0.59 g (52%). The product was obtained as a yellow crystalline compound. HPLC (C18): $t_R$ 6.4 min, 85-100% B in 20 min. (A:$H_2O$+0.1% TFA; B:$CH_3CN$+0.1% TFA).

$^1$H NMR (DMSO-$d_6$): δ 3.25 (dd, J=9.0 and 14.5 Hz, 0.5H), 3.54 (m, 1H), 3.77 (dd, J=5.9 and 14.3 Hz, 0.5H), 4.01-4.26 (m, 3H), 4.32 (m, 0.5H), 4.40 (m, 0.5H), 7.00-7.98 (m, 15H), 8.23 (m, 1H), 8.35 (m, 1H), 8.56 (d, J=8.1 Hz, 1H), 11.08 (s, 0.5H), 11.17 (s, 0.5H).

After incorporation of Fmoc-Trp(2-NpsO$_2$)—OH into a peptide, MS electrospray analysis revealed that the oxidation of Fmoc-Trp(2-Nps)-OH had been incomplete; the product was a circa 3:1 mixture of the sulfoxide Fmoc-Trp(2-NpsO)—OH and the sulfone Fmoc-Trp(2-NpsO$_2$)—OH. Proton NMR indicates a 1:1 mixture of the two compounds based on double sets of signals for β-, α- and carboxyl-protons.

E) Preparation of Fmoc-Trp(2-Pmc)-OH

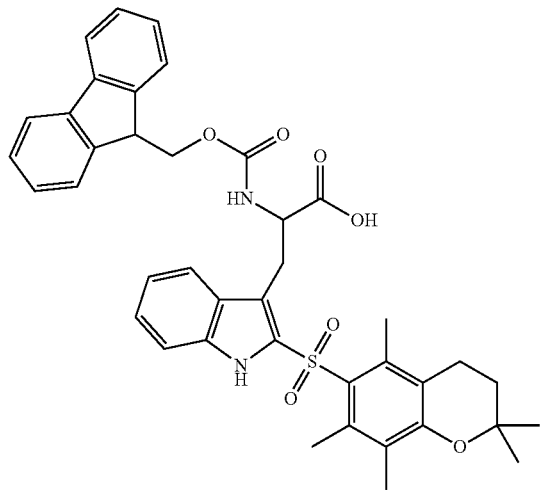 [SMILES: Cc1c(C)c(S(=O)(=O)c2[nH]c3ccccc3c2CC(NC(=O)OCC2c3ccccc3-c3ccccc32)C(=O)O)c(C)c2c1OC(C)(C)CC2]

Method I: By transferal of the Pmc-group from Fmoc-Arg(Pmc)-OH

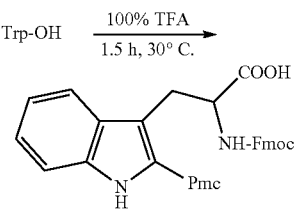

Fmoc-Arg(Pmc)-OH (0.5 g, 0.75 mmol) and Fmoc-Trp-OH (0.43 g, 0.1 mmol) was dissolved in 10 ml 100% TFA and heated at 30° C. for 1.5 hours. After evaporation of TFA, Fmoc-Arg-OH was removed by column chromatography on silica gel with heptane/ethyl acetate 2:1 as mobile phase. Fmoc-Trp(2Pmc)-OH was isolated by preparative HPLC (C18, 70-100% B in 15 min., t$_R$ 14.8 min, (A: H$_2$O+0.1% TFA; B: CH$_3$CN+0.1% TFA)). Isolated yield 130 mg (0.19 mmol, 25%).

$^1$N NMR (400 MHz, CDCl$_3$): δ 1.30 (s, 6H), 1.79 (t, 2H), 2.07 (s, 3H), 2.43 (s, 3H), 2.48 (s, 3H), 2.59 (t, 2H), 3.03 (m, 1H), 3.25 (m, 1H), 4.1-4.3 (m, 3H), 4.42 (m, 1H), 6.53 (d, 1H), 7.15-7.78 (m, 12H), 8.90 (s, 1H).

Materials:

| | |
|---|---|
| Fmoc-Arg(Pmc)-OH | BACHEM no B-1670 |
| Fmoc-Trp-OH | BACHEM no B-1445/SENN no 02019 |
| Trifluoroacetic acid | KEBO no 1.8341-100/Fluka no 91700 |

Method II: By Transferal of the Pmc-Group from Phenylethylguanidyl-Pmc

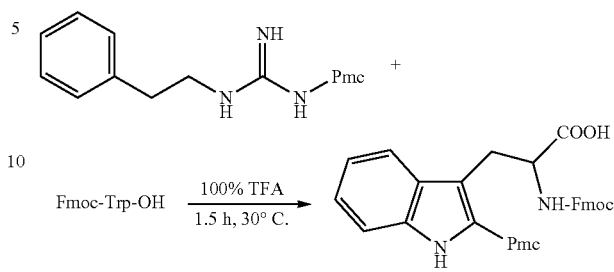

2,2,5,7,8-Pentamethylchroman

References: Robert Ramage, Jeremy Green and Alexander J. Blake, *Terahedron* Vol. 47, No. 32, pp. 6353-6370, 1991.

Reaction:

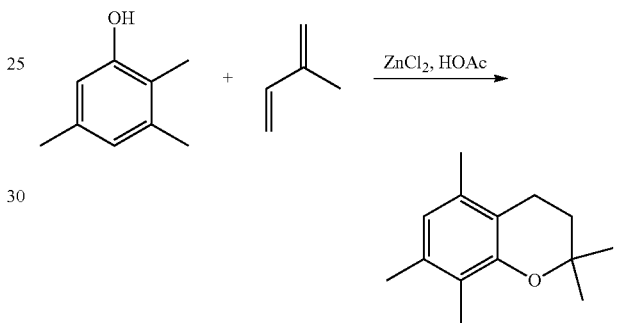

Chemicals:

| Substance | Quantity | MW | mmoles | eqv. | Source |
|---|---|---|---|---|---|
| 2,3,5-Trimethylphenol | 50.03 g | 136.20 | 367.33 | 1.0 | Fluka |
| Isoprene | 25.09 g | 68.12 | 368.32 | 1.0 | Jannsen Chimica |
| ZnCl$_2$ | 5.94 g | 136.29 | 43.58 | 0.12 | Fluka |
| Acetic acid | 47 ml | — | — | — | KEBO lab |

Procedure:

2,3,5-Trimethylphenol (50.03 g, 0.367 moles), isoprene (25.09 g, 0.368 moles) and fused zinc chloride (5.94 g, 0.044 moles) was stirred with anhydrous acetic acid (47 ml) for 14 hours at room temperature. The cloudy red coloured mixture was then gradually heated and it became clear. Upon refluxing the reaction mixture turned black, and after 8 hours of reflux it was cooled to room temperature. The reaction mixture was poured into 250 ml water and the black oil separated. The water was extracted with pentane (3×200 ml) and the combined organic phases washed with Claisen's alkali (2×150 ml), water (3×250 ml) and brine (2×200 ml), dried over CaCl$_2$ and evaporated to a brown oil under reduced pressure. The crude product was distilled at 0.48 mBar affording the product as a pale yellow liquid (36.90 g, 49% yield); b.p. 82-96° C. (0.48 mBar); >95% pure (GC).

Results:

The product was isolated as a pale yellow liquid which solidified upon cooling in 49% yield.

$^1$H NMR (CDCl$_3$, 400 MHz): δ=1.30 (6H, s, 2×CH$_3$), 1.78 (2H, t, J=7 Hz, CH$_2$), 2.07 (3H, s, CH$_3$), 2.15 (3H, s, CH$_3$), 2.19 (3H, s, CH$_3$), 2.59 (2H, t, J=7 Hz, CH$_2$), 6.54 (1H, s, aromatic H).

$^{13}$C NMR (CDCl$_3$, 400 MHz): δ=11.42 (CH$_3$), 18.91 (CH$_3$), 19.84 (CH$_3$), 20.49 (CH$_2$), 26.97 (2×CH$_3$), 32.79 (CH$_3$), 73.10 (C(CH$_3$)$_2$), 116.67 (Ar—C), 122.03 (Ar—C), 122.29 (Ar—C), 133.44 (Ar—C, 134.70 (Ar—C), 151.72 (Ar—C).

MS (GC/MS): m/z=204(100), 189(14), 149 (91).

2,2,5,7,8-Pentamethylchroman-6-sulfonyl chloride

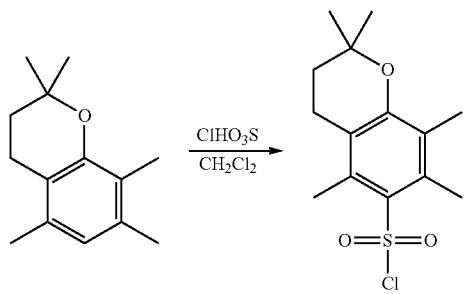

To a solution of 2,2,5,7,8-pentamethylchroman (3.39 g, 16.6 mmol) in 30 ml dichloromethane at −8° C. was added under stirring chlorosulfonic acid (3.98 g, 34.2 mmol) in 30 ml dichloromethane within 3 minutes. The mixture was stirred at −8° C. for 15 minutes and at room temperature for 2.5 hours. The reaction mixture was carefully shaken with 50 ml dichloromethane and 100 ml ice a couple of times and the phases separated. The crude product contained circa 16% of starting material as judged by $^1$H NMR. When hot pentane was added to the crude product, a dark oil was formed which was removed by decanting. The product was then isolated by crystallisation from pentane as a light brown powder (2.80 g, 9.3 mmol). Yield 56%.

$^1$H NMR (CDCl$_3$): δ 1.34 (s, 6H), 1.85 (t, J=7.0 Hz, 2H), 2.14 (s, 3H), 2.60 (s, 3H), 2.62 (s, 3H), 2.68 (t, J=7.0 Hz, 2H).

2-Phenylethylguanidine hemisulfate

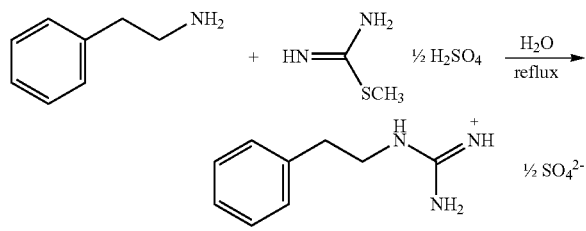

2-Phenylethylamine (8.49 g, 70.1 mmol) and S-methyl-isothiourea sulfate (9.43 g, 33.9 mmol) was dissolved in 100 ml distilled water. Air was passed over the reaction mixture and through 50% NaOH (500 ml) and then through 5% cuprous sulfate (250 ml). The reaction mixture was heated at reflux for 5 hours. Evaporation of the solvent yielded a white powder. The product was isolated by crystallisation from 96% ethanol, washed with cold acetone and diethyl ether and dried in a desecrator. After three crystallizations, the product contained only minor amounts of starting material. The reaction yielded 61.5% (9.14 g) 2-phenylethylguanidine hemisulfate.

$^1$H NMR (D$_2$O): δ 2.87 (t, J=6.6 Hz, 2H), 3.44 (t, J=6.6 Z, 2H), 7.24-7.38 (m, 5H)

Phenylethylguanidyl-Pmc:

Reaction: Ian Michael Eggleston, Ph.D. thesis, University of Oxford, 1990.

Reaction:

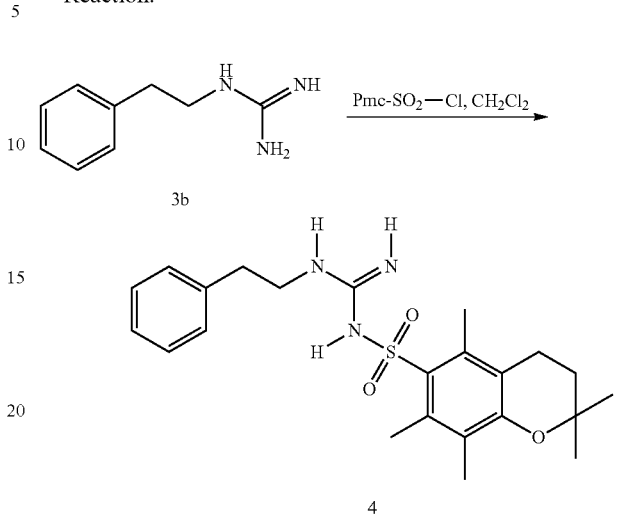

Chemicals:

| Substance | Quantity | MW | mmoles | eqv. | Source |
| --- | --- | --- | --- | --- | --- |
| 2-Phenylethylguanidine hemisulfate | 7.40 g | 212.24 | 34.87 | 1.5 | B11-01 |
| Pmc-SO$_2$—Cl | 7.00 g | 302.07 | 23.17 | 1.0 | B15-02 |
| CH$_2$Cl$_2$ | 150 ml | — | — | — | KEBO lab |

Procedure:

2-Phenylethylguanidine hemisulfate (3) (7.40 g, 34.87 mmoles) was suspended in 6M NaOH (80 ml) and extracted into chloroform (2×80 ml). After evaporation of the solvent in vacuo the oily residue was co-evaporated with benzene (2×10 ml). The free guanidine (3b) was dissolved in 75 ml dichloromethane in a 250 ml round bottomed flask equipped with a magnetic stirring bar and a 100 ml addition funnel with pressure equalizer. The funnel was charged with Pmc-SO$_2$—C1 (7.00 g, 23.17 mmoles) dissolved in 75 ml dichloromethane. The equipment was flushed with nitrogen, and the reaction was performed under a weak nitrogen flow. The round bottomed flask was cooled in an ice/water bath, and the Pmc-SO$_2$Cl solution added over a period of 20-25 minutes. The reaction mixture was allowed to attain room temperature overnight. The dichloromethane was evaporated in vacuo and the residue partitioned between water (100 ml) and ethyl acetate (120 ml). The organic layer was then washed with water (100 ml). Upon cooling of the ethyl acetate the product appeared as a white/pale yellow powder, which was filtered off and dried in vacuo.

Results:

3.32 g of a pale yellow powder was isolated. The yield of the reaction is 33%. Melting point: 145-147° C.

$^1$H NMR (CDCL$_3$): δ=1.30 (6H, s, 2×CH$_3$), 1.80 (2H, t J 7.0 Hz, CH$_2$), 2.09 (3H, s, CH$_3$), 2.51 (3H, s, CH$_3$), 2.52 (3H, s, CH$_3$), 2.61 (2H, t J 6.6 Hz, CH$_2$), 2.81 (2H, t J 7.0 Hz, CH$_2$), 3.43 (2H, m, CH$_2$), 6.21 (3H, broad s, 3×NH), 7.12-7.25 (5H, m, aromatic protons).

MS: m/z=429(6), 204(37), 149(100), 105(24), 92 (37).

Fmoc-Trp(2-Pmc)-OH:
Reaction:

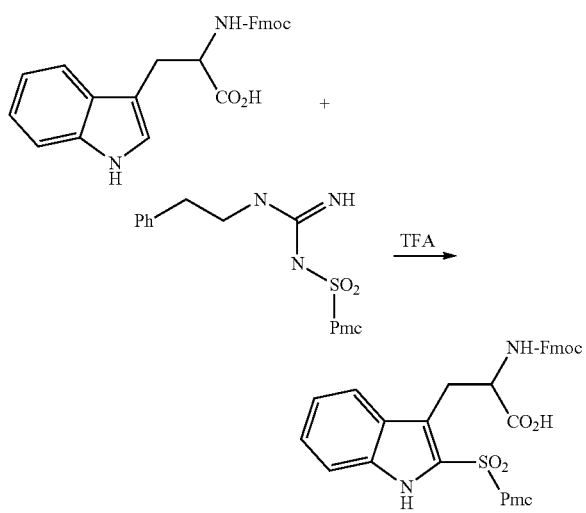

Chemicals:

| Substance | Quantity | MW | mmoles | eqv. | Source |
|---|---|---|---|---|---|
| Fmoc-Trp-OH | 4.14 g | 426.49 | 9.71 | 1.0 | SENN |
| $N^G$-(6-SO$_2$-Pmc)-2-phenylethylguanidine | 2.08 g | 429.59 | 4.84 | 1.0 | BEH-B17 |
| Trifluoroacetic acid | 25 ml | — | — | — | Fluka |

Procedure:
$N^G$-(6-SO$_2$-Pmc)-2-phenylethylguanidine (2.08 g, 4.84 mmoles) and Fmoc-Trp-OH (4.14 g, 9.71 mmoles) was stirred with trifluoroacetic acid (25 ml) at room temperature for 2 hours. The reaction mixture was then evaporated in vacuo and the residue partitioned between chloroform and 1 M hydrochloric acid. By cooling of the chloroform solution the excess of Fmoc-Trp-OH could be removed by filtration.
The product was purified by flash chromatography (ethyl acetate/heptane, 1:1).
Results:
The title compound was isolated as a white powder in 26% yield.
Materials:

| | |
|---|---|
| Chlorosulfonic acid | Fluka no 26388 |
| Phenylethylamine | Fluka no 77900 |
| S-Methylisothiourea sulfate | Fluka no 67730 |
| Fmoc-Trp-OH | BACHEM no B-1445/SENN no 02019 |
| Trifluoroacetic acid | KEBO no 1.8341-100/Fluka no 91700 |

F) Preparation of Fmoc-2,5,7-tritertbutyltryptophan 2,5,7-tritertbutyltryptophan Tryptophan (4.00 g, 19.59 mmol), trifluoroacetic acid 98% (60 ml) and tert-butanol (15.54 g, 209.66 mmol) were mixed. The reaction mixture was stirred at room temperature for 48 hours. The trifluoroacetic acid was evaporated. The residue was suspended in 40 ml distilled water, and the pH adjusted to neutral with addition of sodium hydrogen carbonate. The crude product was obtained by filtration. Crystallisation from 50% ethanol afforded the product as a white powder (85-90% pure).

$^1$H NMR (CDCl$_3$): δ=1.34 (9H, s, 3 CH$_3$), 1.46 (9H, s, 3 CH$_3$), 1.49 (9H, s, 3CH$_3$), 7.45 (1H, s, CH arom), 7.18 (1H, s, CH arom), 5.29 (1H, s, NH).
Fmoc-2,5,7-tritertbutyltryptophan:
The title compound was prepared as described for Fmoc-Trp(1-benzyl)-OH.

EXAMPLE 3

Bioactivity of Lactoferricin Analogs

Synthesis of the Analogs
All the peptides were synthesized on a 9050 Millipore Automatic Peptide Synthesizer using Fmoc protection and activation with pentafluorophenyl (Pfp)esters or in situ activation with the coupling reagent HATU (O-(7-azabenzotriazol-1-yl)-1,1,3,3-tetramethyl uronium hexafluorophosphate). In the case of coupling with pentafluorophenyl esters, 1-HOBt (1-hydroxy-benzotriazole) was added to catalyse the reaction, and when using the coupling reagent HATU the reaction was base catalysed with DIPEA (diisopropylethylamine). All amino acids with reactive side chains were protected with acid labile protecting groups and cleaved upon treatment with TFA (trifluoroacetic acid) containing scavengers. (See below for scavenger mixture). At the same time the peptides were cleaved from the solid support on treatment with the TFA solution.
A) Attachment of the First Amino Acid to the Solid Support when Synthesizing all D-Peptides
The solid support PAC-PEG-PS (Peptide Acid—Poly Ethylene Glycol—Poly Styrene resin) (1 eq.) was mixed together with Fmoc-D-amino acid-OPfp (5 eq.) and DMAP (dimethylaminopyridine) (1 eq.) in a small volume of DMF (dimethylformamide) and left to swell for 30 minutes. The solution was then stirred slowly for 4½ hours. Ac$_2$O (acetic acid anhydride) (2.5 eq.) and DMAP (0.1 eq.) were then added to the solution in order to acetylate any remaining hydroxyl groups on the solid support. The solution was then stirred for another hour. The solid support with the C-terminal amino acid attached was isolated by filtration and washed several times on the filter with DMF. The solid support was then used in the synthesis of the target peptide on the 9050 Millipore Automatic Peptide Synthesizer.
B) Acetylation of the N-Terminal H$_2$N-Group Using Acetic Acid Anhydride
The peptide-resin complex was dissolved in a small volume of DMF and treated with an excess of acetic acid anhydride (20 eq.) and DMAP (5 eq.) for four hours while slowly stirring the solution with a small magnet. Complete acetylation was verified by a ninhydrin test/Kaiser's test (see below).
C) Ninhydrin Test/Kaiser's Test
Less than 1 mg of the peptide-resin complex was treated with small equal volumes of a 5% ninhydrin solution in ethanol, a solution of 80 g phenol in 20 ml ethanol and a solution of dried, distilled pyridine. The reaction mixture was heated for two minutes at 110° C., and investigated under a microscope. (In this test a yellow reaction mixture indicates successful acetylation, while a blue solution indicates still free amino groups.)
D) Cleavage of Acid Labile Protecting Groups
Cleavage of acid labile protection groups and cleavage of the peptides from the solid support was achieved using a mixture of 2% anisol, 2% ethandithiol (EDT), 2% water and 2% phenol in TFA, and with cleavage times of no more than four hours. The solid support was then removed by filtration and the peptide precipitated in diethyl ether. The ether solution containing TFA was removed using a pasteur pipette, and the peptide was washed several times with diethylether and dried under high vacuum.

E) Purification

The peptides were purified by HPLC using a C18-reversed phase column (*) and a mixture of water and acetonitrile (both added 0.1% TFA) as mobile phase. Selected wavelength for detection of peptide fractions was 254 nm.

(*) PrePak®Cartridge 25×100 mm. DeltaPak™ C18 15 μm 100 Å. (waters corporation.)

F) Analysis

All peptides were analysed for impurities on an analytical HPLC C18-reversed phase column using a mixture of water and acetonitrile (both added 0.1% TFA) as mobile phase. The molecular weight of the peptides were determined by positive ion electrospray ionization mass spectrometry (VG Quattro Quadrupole).

Amino Acid Derivatives Used in Synthesis of Both L- and D-Analogs of Lactoferricin

| | |
|---|---|
| Fmoc-AlaPEG-PS (solid support) | Fmoc-Lys(tBoc)-OPfp |
| Fmoc-Arg(Pbf)-OH | Fmoc-Met-OPfp |
| Fmoc-Arg(Pmc)-OH | Fmoc-β-(2-naphthyl)-alanine-OH |
| Fmoc-Asn(Trt)-OPfp | Fmoc-Phe-OPfp |
| Fmoc-Cys(Acm)-OPfp | Fmoc-Ser(tBu)-OPfp |
| Fmoc-Gln-OPfp | Fmoc-Thr(tBu)-OPfp |
| Fmoc-Glu(OtBu)-OPfp | Fmoc-Trp-OPfp |
| Fmoc-Gly-OPfpFmoc-Tyr(tBu)-OPfp | Fmoc-Leu-OPfp |

Amino acid derivatives were purchased from either sachem, MilliGen/Biosearch (Division of Millipore) or PerSeptive Biosystems.

Antimicrobial Activity of Alanine Scan Peptides Containing a Tryptophan-Pmc Residue During deprotection of acid labile protecting groups and cleavage of the peptide from the resin with trifluoro acetic acid, a side reaction involving transfer of the Pmc (2,2,5,7,8-pentamethylchroman-6-sulphonyl group) protecting group from arginine to the second position of the indole of tryptophan was observed. Isolation of these byproducts have been done, and the results from MIC analyses are given in Table 2. This table also shows the results of an alanine scan performed on LFB with no Pmc groups.

During an alanine scan, a series of peptides are produced wherein successive amino acids have been substituted by alanine.

The sequence of native bovine lactofericin from amino acids 17 to 31 (LFB 17-31) is H$_2$N-Phe-Lys-Cys-Arg-Arg-Trp-Gln-Trp-Arg-Met-Lys-Lys-Leu-Gly-Ala-COOH (SEQ ID No. 19).

TABLE 2

MIC results for alanine scan peptides with a Pmc group attached to one of the two tryptophan residues. Results also shown for an alanine scan performed on LFB with no Pmc groups.

| | Pmc | | Without Pmc | |
|---|---|---|---|---|
| Peptide | MIC E. coli | MIC S. aureus | MIC E. coli | MIC S. aureus |
| LFBA 1 | 8.75 | 10 | 70 | >200 |
| LFBA 2 | 11.25 | 10 | 80 | >200 |
| LFBA 3 | 7.5 | 7.5 | 25 | 100 |
| LFBA 4 | 15 | 27.5 | 70 | >200 |
| LFBA 5 | 10 | 50 (*) | 120 | >200 |
| LFBA 6 | 25 | 17.5 | >200 | >200 |
| LFBA 7 | 20 | 7.5 | 30 | 150 |
| LFBA 8 | 15 | 17.5 | >200 | >200 |
| LFBA 9 | 10 | 12.5 | 55 | >200 |
| LFBA 10 | 20 | 22.5 | 140 | >200 |
| LFBA 11 | 22.5 | 22.5 | 70 | >200 |

TABLE 2-continued

MIC results for alanine scan peptides with a Pmc group attached to one of the two tryptophan residues. Results also shown for an alanine scan performed on LFB with no Pmc groups.

| | Pmc | | Without Pmc | |
|---|---|---|---|---|
| Peptide | MIC E. coli | MIC S. aureus | MIC E. coli | MIC S. aureus |
| LFBA 12 | 20 | 20 | 50 | >200 |
| LFBA 13 | 15 | 15 | 50 | >200 |
| LFBA 14 | 15 | 17.5 | 25 | 160 |
| LFBA 17-31 | 10 | 10 | 50 | 100 |

(*) MIC of 25 has been observed

The results show that a Pmc group attached to one of the tryptophan residues increases the activity four times for E. coli. Even more marked is the effect on S. aureus. This gram positive bacteria was found to be nearly totally resistant to all the alanine scan analogs, but shows now a MIC between 10 and 22.5 μg/ml. This represents a ten fold increase in antibacterial activity relative to native LEB 17-31. The tryptophan-Pmc residue, which is hydrophobic, seems therefore to increase the peptide; affinity for the hydrophobic parts of the bacterial cell membrane to such an extent that the antibacterial activity of the peptide is no longer so sequence dependent as for the peptide without this residue.

Comparison of Antimicrobial Activity Between Native Bovine Lactoferricin (LFB 17-31) and Enantio-, Retro- and Retro-Enantio LFB 17-31 and these Same Peptides Incorporating a Tryptophan-Pmc Residue Peptides containing a Pmc-group transferred from an arginine residue to a tryptophan residue was also isolated after synthesis of Enantio-, Retro- and Retro-Enatio LFB 17-31.

TABLE 3

MIC results for native bovine lactoferricin (LFB 17-31), Enantio-, Retro- and Retro-Enantio LFB 17-31 and for these peptides with a Pmc group attached to one of the two tryptophan residues.

| Peptide | MIC E. coli | MIC S. aureus | % Hemolysis 10 g/ml |
|---|---|---|---|
| Native LFB 17-31 | 50 | 100 | 2.6 |
| Enantio LFB 17-31 | 7.5 | 60 | 3.05 |
| Retro LFB 17-31 | 80 | 200 | 2.01 |
| Retro-Enantio LFB 17-31 | 6.25 | 80 | 3.31 |
| LFB 17-31 Pmc | 10 | 10 | 2.8 |
| Enantio LFB 17-31 Pmc | 7.5(*) | 100 | 3.17 |
| Retro LFB 17-31 Pmc | 10 | 10 | 2.5 |
| Retro-Enantio LFB 17-31 Pmc | 7.5 | 12.5 | 5.28 |

(*)MIC of less than 5 has been observed.

The Enantio peptide, which is the exact mirror image of the native peptide, shows remarkable improvements in antibacterial activity. (In fact, this peptide shows the same activity as the native peptide LFB 17-31 with a tryptophan-Pmc residue, in the case of E. coli.) Configurationally this means that an all-D-amino acid analog of LFB 17-31 interacts better with the chiral phospholipids of the bacterial cell membrane than the native all-L-amino acid peptide LFB 17-31. It may also imply that this Enantio peptide is more resistant to degradable proteases of the bacteria.

The Retro peptide, with an inverted sequence in respect to LFB 17-31, shows no improvements in antibacterial activity, which is consistent with the theory of the antibacterial activity of LFB 17-31 being sequence specific. This peptide is not really an isomer of bovine lactoferricin since the amino acid sequence is totally different. The low antibacterial activity of this peptide does therefor not come as any surprise.

A remarkably high antibacterial activity against *E. coli* was observed for the Retro-Enantio peptide which, as already mentioned, adopts the same α-helical conformation as the native peptide LFB 17-31, except that the amide bonds point in opposite directions. The all-L-amino acid stereoisomer, Retro LFB 17-31, shows low antibacterial activity. The reason may be that all-D-amino acid peptides either interact more strongly with the chiral phospholipids of the bacterial cell membrane or that they are more resistant to proteases than their all-L-amino acid counterparts.

The activity of the peptides against *S. aureus* is not as high as observed for *E. coli*, indicating that the interactions of the peptides with the lipopolysaccharide layer of gram negative bacteria might be stronger than the interactions with the lipid cell membrane of gram positive bacteria.

The activity of the tryptophan-Pmc containing peptides do not show the same differences between all-D- and all-L-amino acid isomers as was observed for the peptides without the Pmc group. The effect of the tryptophan-Pmc residue seems to be more pronounced than the configurational effects found among the peptides without this residue, especially in the case of *S. aureus*. Most noticeable is the tremendous increase in activity of the Retro-Pmc peptide. The activity of this peptide is increased eight times in the case of *E. coli* and more than ten times in the case of *S. aureus* just because of the tryptophan-Pmc residue.

The improvements observed upon Pmc modification in the case of *E. coli* is neglible, but the modification increases the activity against *S. aureus* about six times. The gram positive bacteria are obviously more vulnerable towards tryptophan-Pmc containing peptides than their non tryptophan-Pmc containing counterparts.

Antimicrobial Activity of Tryptophan Modified Human (LFH), Porcine (LFP) and Caprine (LFG) Lactoferricin The results from the alanine scan of bovine lactoferricin (LFB 17-31) showed that the two tryptophan residues in positions six and eight could not be substituted by alanine without a major loss of antibacterial activity. Examination of the similar sequence parts of native LFH, LFP and LFG lactoferricin shows that these peptides lack the tryptophan residue in position eight, but have during evolution conserved the tryptophan residue in position six. We have synthesized LFH, LFP and LFG analogs with a tryptophan residue substituted in the position eight to see if the antimicrobial activity of these peptides could be increased. The MIC values for the native sequences are given in Table 4, together with the tryptophan modified peptides.

H₂N-Thr-Lys-Cys-Phe-Gln-Trp-Gln-Trp-Asn-Met-Arg-Lys-Val-Arg-Gly-Gly-COOH (SEQ ID NO: 20)
Sequence of modified human lactoferricin (LFHW8) Substituted tryptophan is high-lighted. (Arg→Trp)
H₂N-Ser-Lys-Cys-Tyr-Gln-Trp-Gln-Trp-Arg-Met-Arg-Lys-Leu-Gly-Ala-COOH (SEQ ID NO: 21)
Sequence of modified caprine lactoferricin (LFGW8). Substituted tryptophan is high-lighted. (Arg→Trp)
H₂N-Glu-Lys-Cys-Leu-Arg-Trp-Gln-Trp-Glu-Met-Arg-Lys-Val-Gly-Gly-COOH (SEQ ID NO: 22)

TABLE 4

MIC results for tryptophan modified human (LFHW8) and caprine (LFGW8) lactoferricin. (MIC values for native LFB 17-31 and native sequences of LFH and LFG are also listed for the sake of comparison.)

| Peptide | MIC *E. coli* | MIC *S. aureus* | % Hemolysis 10 μg/ml |
|---|---|---|---|
| LFHW8 | 110 | >1000 | 2.5 |
| LFPW8 | 500 | >1000 | 2.9 |
| LFGW8 Y13 | 110 | >1000 | NT |

TABLE 4-continued

MIC results for tryptophan modified human (LFHW8) and caprine (LFGW8) lactoferricin. (MIC values for native LFB 17-31 and native sequences of LFH and LFG are also listed for the sake of comparison.)

| Peptide | MIC *E. coli* | MIC *S. aureus* | % Hemolysis 10 μg/ml |
|---|---|---|---|
| LFGW8 | 500 | >1000 | 2.7 |
| Native LFB 17-31 | 50 | 100 | 2.6 |
| Native LFH | >1000 | >1000 | NT |
| Native LFP | >1000 | >1000 | |
| Native LFG | 750 | N.T | 2.4 |

N.T = Not tested

Both LFHW8 and LFGW8 show improvements in activity against *E. coli* compared to the native sequences of the same peptides.

Antimicrobial Activity of LFH, LFP and LFG with a Tryptophan-Pmc Residue

During acidic cleavage of the peptide (either with or without the above modifications to the native sequence) from the resin and cleavage of acid labile protecting groups, a byproduct with a Pmc-group attached to one of the tryptophan residues was isolated and analysed for antibacterial activity. The results are shown in Table 5.

TABLE 5

MIC results for LFH, LFG and LFP with a Pmc group attached to one of the two tryptophan residues, for LFC Pmc and LFH Pmc, the PMC group will be attached to the only available tryptophan.

| Peptide | MIC *E. coli* | MIC *S. aureus* |
|---|---|---|
| LFG Pmc | 25 | 25 |
| LFH Pmc | 25 | 50 |
| LFHW8 Pmc | 25 | 20 |
| LFGW8 Pmc | 50 | 75 |
| LFPW8 Pmc | 20 | 50 |
| LFHW8 Y13Pmc | 25 | 20 |

As for all tryptophan-Pmc containing peptides analysed so far, these peptides generally show remarkable improvements in antibacterial activity against both *E. coli* and *S. aureus*.

Antimicrobial Activity of Tryptophan Rich Analogs of Bovine Lactoferricin (LFB 17-31)

The alanine scan showed that the two tryptophan residues in the sequence of bovine lactoferricin 17-31 were absolutely essential to the antibacterial activity of the peptide. Alanine substitution of any of these two residues led to a major loss of antibacterial activity. The alanine scan also showed that the nonessential amino acids in the sequence of bovine lactoferricin 17-31 were the three residues Cys(3), Gln(7) and Gly (14). Based on this knowledge we therefore synthesized a series of five tryptophan rich analogs of bovine lactoferricin 17-31 with one, two or three of the nonessential amino acids substituted by tryptophan. This technique of performing an alanine scan and then replacing seeming non-essential amino acids with Tryptophan or other bulky and/or lipophilic amino acids can be used to enhance the cytotoxicity of peptides generally, and is not limited to lactoferricin. The sequences of the tryptophan rich bovine lactoferricin analogs are shown below.

LFBW3:
(SEQ ID NO: 23)
H₂N-Phe-Lys-Trp-Arg-Arg-Trp-Gln-Trp-Arg-Met-Lys-Lys-Leu-Gly-Ala-COOH

LFBW14:
(SEQ ID NO: 24)
H₂N-Phe-Lys-Cys-Arg-Arg-Trp-Gln-Trp-Arg-Met-Lys-Lys-Leu-Trp-Ala-COOH

LFBW3,14:
(SEQ ID NO: 25)
H₂N-Phe-Lys-Trp-Arg-Arg-Trp-Gln-Trp-Arg-Met-Lys-Lys-Leu-Trp-Ala-COOH

LFBW3,7,14:
(SEQ ID NO: 26)
H₂N-Phe-Lys-Trp-Arg-Arg-Trp-Trp-Trp-Arg-Met-Lys-Lys-Leu-Trp-Ala-COOH

LFBW4,10:
(SEQ ID NO: 27)
H₂N-Phe-Lys-Cys-Trp-Arg-Trp-Gln-Trp-Arg-Trp-Lys-Lys-Leu-Gly-Ala-COOH

TABLE 6

MIC results for five tryptophan rich analogs of bovine lactoferricin (LFB 17-31) together with native LFB 17-31.

| Peptides | MIC *E. coli* | MIC *S. aureus* |
| --- | --- | --- |
| LFB 17-31 | 50 | 100 |
| LFBW3 | 20 | 20 |
| LFBW14 | 20 | 25 |
| LFBW3,14 | 10 | 10 |
| LFBW3,7,14 | 20 | 20 |
| LFBW4,10 | 5 | 10 |

Substitution of nonessential amino acids in the sequence of LFB 17-31 by tryptophan residues improves the antibacterial activity of these peptides by at least two times that of the native sequence in the case of *E. coli* and by four times in the case of *S. aureus*.

Peptide W3714, with three additional tryptophan residues (a total of five tryptophan residues in the peptide), has decreased activity. This is probably more a result of a solubility problem, this peptide being less soluble in aqueous solutions and therefore giving lower concentrations than calculated. This has been physically observed during MIC testing procedures when the peptide tended to precipitate at high concentrations.

EXAMPLE 4

Substituted magainin peptides have also been prepared. Native magainin 2 has the following sequence: MAG2: H₂N-Gly-Ile-Gly-Lys-Phe-Leu-His-Ser-Ala-Lys-Lys-Phe-Gly-Lys-Ala-Phe-Val-Gly-Glu-Ile-Met-Asn-Ser-COOH (SEQ ID NO: 28).

Table 7 below shows the MIC results for the native peptide and a number of modified peptides wherein single amino acid substitutions for tryptophan or phenylalanine at positions 16 or 19 have been made, with a resulting increase in antibacterial activity.

TABLE 7

| Peptide | MIC *E. coli* | MIC *S. aureus* |
| --- | --- | --- |
| Mag2 | 20 | >200 |
| Mag2 W16 | 5-10 | 5-10 |
| Mag2 W19 | 5-10 | 5-10 |
| Mag2 F19 | 5-10 | 5-10 |

EXAMPLE 5

Antitumoral Effects of Different Peptides

Cyclic LFB 17-41 was from Morinaga, Milk Industri, Japan
Cytotoxicity

Different murine and human tumor cells (4×10⁶) were applied in 96-well culture plates (Costar) in a volume of 0.1 ml RPMI 1640 medium. Peptide solutions (0.1 ml) were added and the plates incubated at 37° C. for 30 minutes, 4 hours or 24 hours. The cytotoxicity was measured using the MTT method (Mosmann et al., J. Immunol. (1986) 136, 2348-2357).
Electron Microscopy
Scanning Electron Microscopy (SEM)

For scanning electron microscopy, Meth A cells were cultivated in a 12 well culture plate and treated with different peptides as described above. Cells were fixed in McDowell's fixative postfixated in 1% OsO₄, dehydrated and critical point dried according to standard procedures. The cells were examined in a Jeol JSM-5300 Scanning microscope.
Transmission Electron Microscopy (TEM)

Meth A cells were harvested from 12 culture plates by aspiration and fixed in McDowell's fixative overnight, followed by postfixation, dehydration and embedding in Epon Araldite according to standard procedures. Ultrathin sections were cut on a Reichert Ultracut S and then contrasted in 5% Uranyl acetate and Reynold's lead citrate. Sections were examined in a Jeol LEM-1010 transmission electron microscope.
Experimental Animals Specific pathogen-free CB6F1 (Balb/c×C57 BL/6) female mice of about 8 weeks of age were obtained from Charles River (Germany). The mice were kept on standard laboratory chow and water. Tumor bearing mice were serologically screened for viral (LDH, CMV) and mycoplasmic infection and in all cases tested negative.
Tumors Meth A is a non-adhesive murine sarcoma cell line [Sveinbjørnsson et al, (1996) BBRC 223: 643-649] syngenic in Balb/c and was maintained in vitro in RPMI 1640 containing 2% Foetal calf serum. Cells in the growth phase were harvested and washed in fresh medium and injected subcutaneously into the abdominal region of the mice. Each mouse received a single inoculation of 5×10⁶ viable tumor cells in RPMI 1640.
Results
In Vitro
Cytotoxicity
Lactoferricin B derivatives A) Meth A
1. Cyclic and Linear LFB The cytotoxic effect of cyclic and linear LFB (17-41) on Meth A cells was studied. Linear LFB, with the cysteins protected with Acm, killed the Meth A cells (1×10⁴/ml) effectively at concentrations higher than 0.6 mg/ml after 4 h incubation (FIG. 2). Cyclic LFB, which is an enzymatically cleaved fragment of bovine lactoferrin effectively killed more than 99% of the cells at concentrations higher than 0.8 mg/ml.

2. LFB Derivatives

Figure 3:
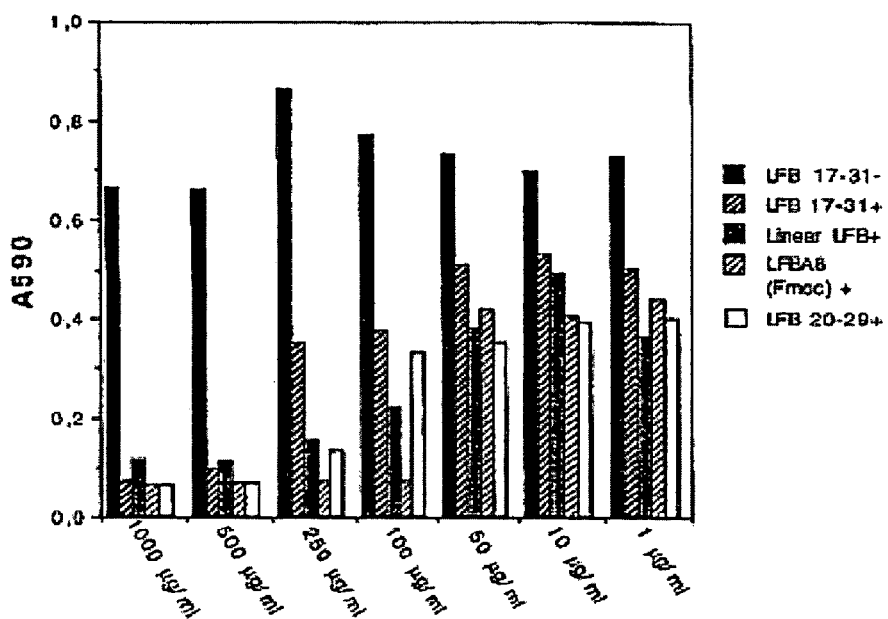
FIG. 3 shows the effects of different LFB derivatives on Meth A cells in vitro after ½ hour incubation, +=pmc-modified; −=unmodified.
Figure 4:
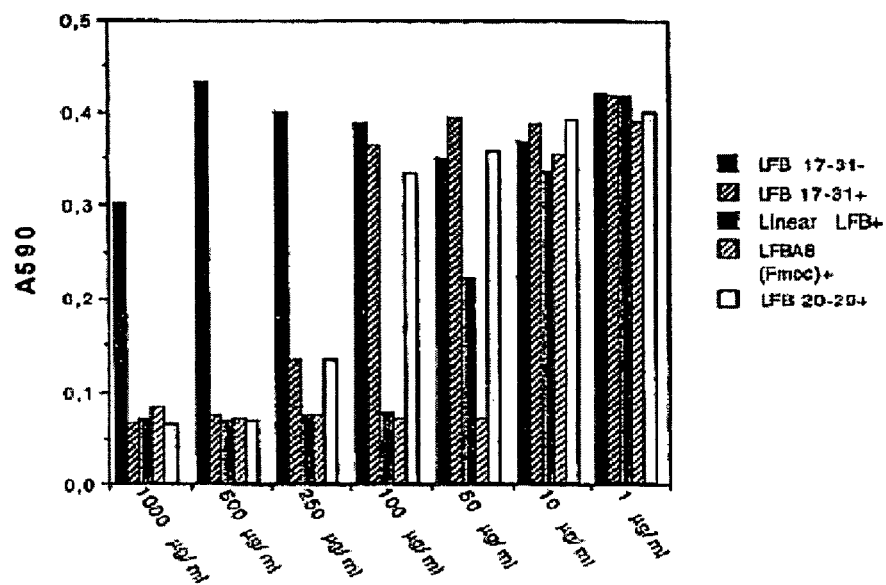
FIG. 4 shows the effects of different LFB derivatives on Meth A cells in vitro after 4 hours incubation, +=pmc-modified; −=unmodified.

LFB derivatives with different lengths and modifications were tested for their cytotoxic properties. Meth A cells were incubated with different concentrations of the different LFB derivatives, for ½ hour and 4 hours. As shown in FIG. 3, Unmodified LFB 17-31 had no significant cytotoxic effect on the Meth A cells at concentrations up to 1 mg/ml after ½ hour incubation. In this experiment it had a weak effect at 1 mg/ml after 4 hours incubation (FIG. 4). The PMC modified LFB 17-31 analog killed the tumor cells at concentrations higher than 500 µg/ml after ½ hour incubation. The same concentration was needed to achieve effective killing after 4 hours. Linear LFB (17-41) modified with Pmc was slightly more effective than Pmc modified LFB 17-31.

In the figures, "−" denotes no Pmc modification and "+" denotes with Pmc modification.

Figure 5:
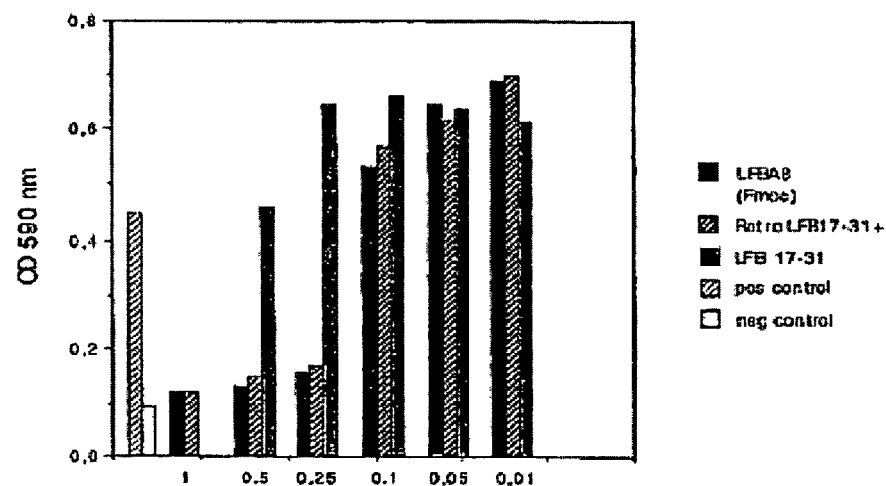
FIG. 5 shows the effects of pmc modified retro LFB 17-31 (+), Fmoc LFB 17-31(A8) and LFB 17-31 on Meth A cells in vitro after ½ hour. RPMI was used as negative control and Triton 100× as positive control. Concentrations are in mg/ml.
Figure 6:
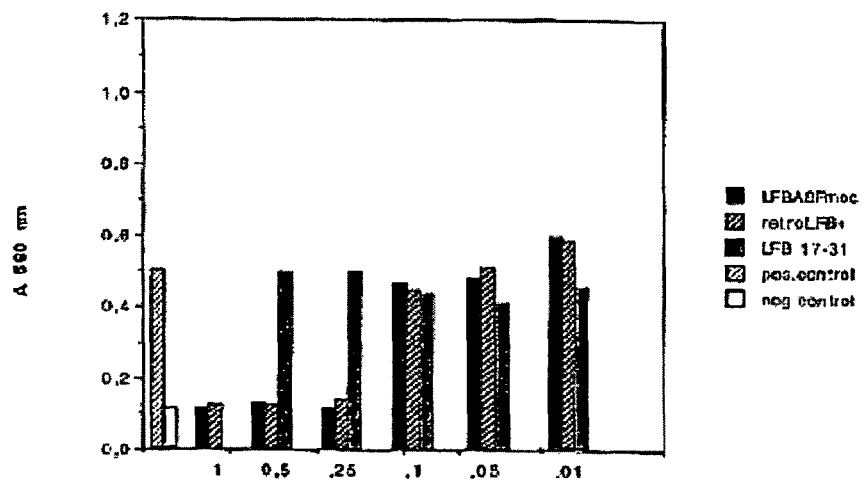
FIG. 6 shows the effects of pmc modified retro LFB 17-31 (+), Fmoc LFB 17-31(A8) and LFB 17-31 on Meth A cells in vitro after 4 hours. RPMI was used as negative control and Triton 100× as positive control. Concentrations are in mg/ml.

A shorter sequence LFB 20-29 modified with PMC killed more than 90% of the cells at 250 µg/ml. An LFB 17-31 analogue (alanine substitution in position 8) that was modified with PMC and N-terminal Fmoc protected was effective at concentrations higher than 100 µg/ml after ½ hour and at 50 µg/ml after 4 hours. An Fmoc protected LFB peptide (Alanine substitution in position 8) killed most of the cells at 250 µg/ml at ½ hour and 4 hours (FIGS. 5 and 6). So it seems that a combination of Fmoc and Pmc modification enhanced the cytotoxic effect of LFB more than each of the two modifications alone. The retro LFB analog was also tested. The retro-Pmc-modified LFB 17-31 also possessed an enhanced cytotoxic effect compared to unmodified LFB 17-31 (FIGS. 5 and 6).

B) Human Promelocytic Leukemia Cell Line HL60.

Figure 7:
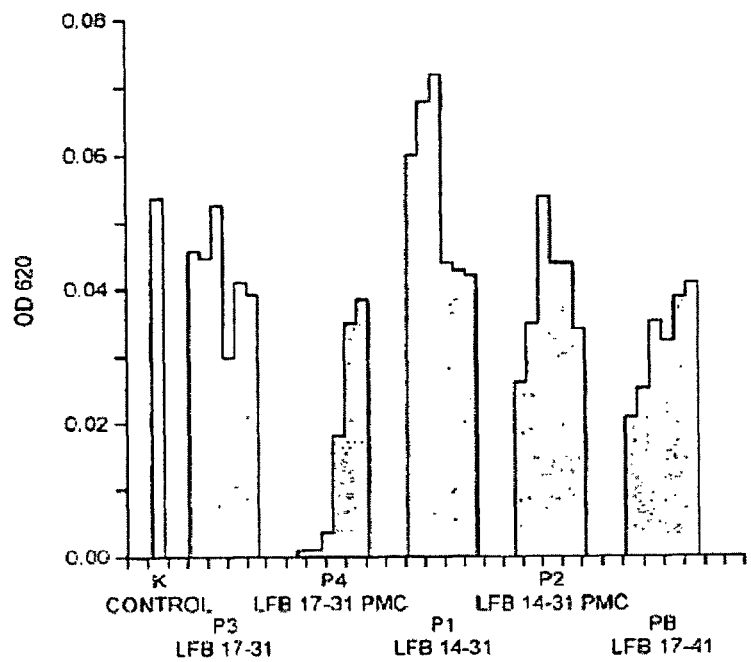
FIG. 7 shows the dose response on human promyelotic leukemia cell line HL 60 after 4 hours. HL 60 cells, $1\times10^4$ were incubated with peptides 50, 30, 20, 10, 5, 1 µg, 1000-20 µg/ml in 2 hours and coloured with MTT.

The cytotoxic effect of LFB 17-41 (PB), LFB 14-31 (P1), LFB 14-31 Pmc (P2), LFB (P3) 17-31 and LFB 17-31 Pmc (P4) on human HL 60 cells was studied. LFB 14-31 and LFB 17-31 showed no cytotoxic effect at the concentration tested whereas LFB 17-41 possessed a weak concentration dependant cytotoxic effect. The LFB 17-31 Pmc peptide induced a markedly stronger effect (appr. 5 fold higher) than the other peptides tested. See FIG. 7.

3. EM Studies

The SEM and TEM results show that the cell membranes are strongly disrupted by lactoferricin peptides, resulting in effective release of intracellular material. The lysis seems to be very rapid, i.e. within minutes by the most effective peptides.

In Vivo

1. Tumor Regression

Murine Meth A fibrosarcoma

After a single inoculation of 5×10⁷ viable Meth A cells, different LF peptides were injected intratumorally (LFB-14-31, LFB 17-31 Pmc, 500 µg in a 50 µl dose; LFB 17-31, 1000 µg in a 50 µl dose), on day 7 and day 10. LFB 14-31 was also injected intraperitoneally (PBI), 500 µg/ml. Saline only was injected in the control mice (50 µl) (K₁,K₂,K₃). The tumor diameter (mean of transversal and longitudinal) were measured with an electronic caliper.

Figure 8:
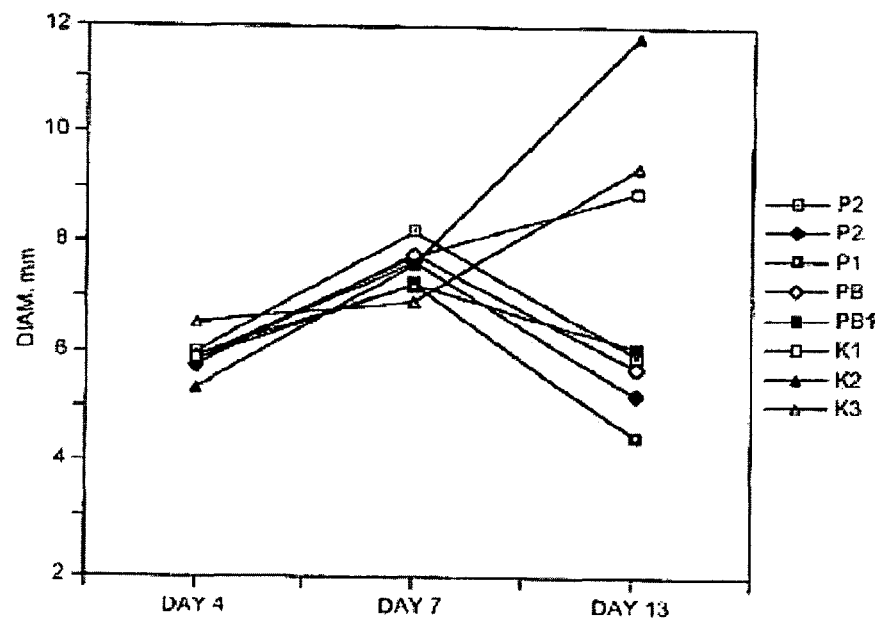
FIG. 8 shows inhibition of tumor growth; Meth A tumor cells ($5\times10^7$ cells) were inoculated on day 1 and treated on day 7 and day 10 with 0.5 mg (1 mg of P1) of the different peptides.

The In Vivo Effect of LFB 17-31, LFB 17-31 Pmc, and LFB on Murine MethA Fibrosarcoma As shown in FIG. 8, all three peptides tested, LFB 17-31 (PB), LFB 14-31 pmc (P2), LFB 14-31 (P1), induced regression of the Meth A tumors, after treatment on day 7 and 10. "Diam.mm." refers to diameter of the tumors.

Interestingly, tumors were also eradicated in the mice that were treated intraperitoneally with LFB 14-31 (PEI). Mice treated with saline only are represented as K1, K2 and K3.

Murine Melanoma B16F10

After a single inoculation of 5×10⁶ viable B16F10 murine melanoma cells, D-LFB A7 pmc-NH₂ was injected intratumorally in the tumors on day 10 and 12 (500 µg/injection in 50 µl saline). Saline only was injected in the control mice (50 µl). The tumor diameter (mean of transversal and longitudinal) were measured every second day with an electronic caliper.

The In Vivo Effect of D-LFB A7 Pmc-NH2 on Murine Melanoma B16F10

Figure 9:
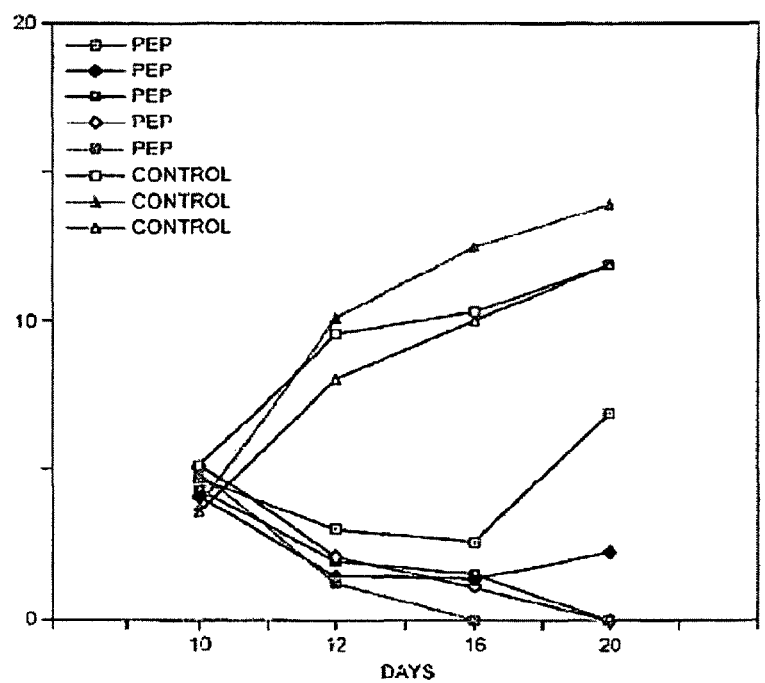
FIG. 9 shows the effect of D-LFB (17-31) A7 Pmc-NH, on B16F10 murine melanoma.
Figure 10:
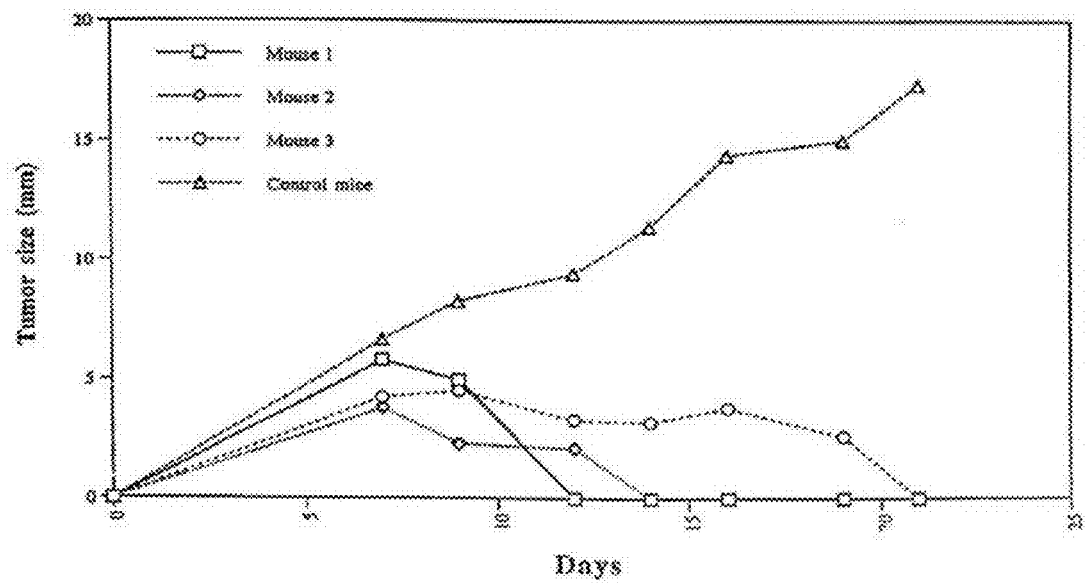
FIG. 10 shows the size of tumors established in Bulb/c mice who are reinoculated with Meth A cells after successful treatment with cLFB. The mice were not treated with cLFB or other peptides in the study, thus some storm of adaptive immunity is shown. Reinoculation of Meth A cells 1 month after the LFB-treatment of Meth A tumors.

As shown in FIG. 9, D-LFB A7 Pmc-NH₂ (pep) was able to effectively induce regression of the solid tumors. The y axis represents the diameter of the tumor in mm. Three out of five were totally eradicated after only two injections. After six days after the first treatment, one of the tumor started to grow again, and 10 days after the first treatment a second tumor started to grow.

2. Adaptive Immunity

After successful treatment of established MethA tumors, some mice were kept for one month before reinoculation of tumor cells as described above. In some of these mice a third inoculation of tumor cells were performed one month later than the second inoculation. No tumors were established in these mice and the mice were kept for a longer period without any effect on the normal condition of these mice.

EXAMPLE 6

The effect of chemical modification of a further moderately active peptide has also been investigated. The stating peptide is a fragment of bovine lactoferrin, which corresponds to residues 14-31 of the native sequence (see Table 1 in FIG. 1 for the full sequence). The antimicrobial activity in the form of MIC values against *E. coli* and *S. aureus*, the toxicity expressed as the concentration which caused 50% hemolysis (EC 50) and the anti-tumor activity in the form of the number of µg/ml of peptide required to kill 50% of MethA cells for the peptides are shown below in Table 8.

TABLE 8

| Peptide | MIC E. coli µg/ml | MIC S. aureus µg/ml | EC 50 (µM) | MethA IC 50 µM/ml |
|---|---|---|---|---|
| LFB 14-31 | 70 | >250 | >404 | no activity |
| LFB 14-31 PMC | 15 | 20 | 244 | 14.6 |
| LFB 14-31 A2,6,10,17 | 20 | 2.5 | >440 | 165 |
| LFB 14-31 A2,6,10,17 PMC | 20 | 2.5 | 165 | 12.8 |
| LFB 14-31 A2,6,10,17R4 | 30 | 20 | >438 | 75.8 |
| LFB 14-31 A2,6,10,17R4 PMC | 10 | 2.5 | 290 | 6.9 |
| LFB 14-31 A2,6,10,17R4,11 | | | >444 | 75.5 |
| LFB 14-31 A2,6,10,17R4,11 PMC | | | 327 | 5.2 |
| LFB 14-31 A2,6,10,17F7R4 | 10 | 2.5 | >440 | 30.2 |
| LFB 14-31 A2,6,10,17F7R4 PMC | 10 | 2.5 | 20 | 7.7 |
| LFB 14-31 A2,6,10,17F7K16L14 | 10 | 10 | >440 | 28.1 |
| LFB 14-31 A2,6,10,17F7K16L14 PMC | 10 | 2.5 | 89 | 5.2 |

As before, the presence of the bulky/lipophilic group PMC on one or more of the tryptophan residues enhances the antimicrobial and anti-tumor activity. Interestingly, the presence of this artificial bulky and lipophilic group is able to selectively enhance bacteriocidal activity, activity against *S. aureus* generally being more enhanced than against *E. coli*.

EXAMPLE 7

Table 9 shows anti-bacterial activity and toxicity data for LFB based peptides incorporating a non-genetic bulky and lipophilic amino in place of one of the amino acids in the native sequence. Further peptides also incorporate a group (PMC) which increases the bulk and lipophilicity of one of the naturally occurring tryptophan residues.

TABLE 9

| Peptide | MIC *E. coli* μg/ml | MIC *S. aureus* μg/ml | % Hemolysis 10 μg/ml | % Hemolysis 100 μg/ml |
| --- | --- | --- | --- | --- |
| LFB | 50 | 100 | 2.6 | 3.47 |
| LFB Bip3 | 10 | 10 | | |
| LFB Bip6 | 25 | 25 | | |
| LFB Bip8 | 15 | 15 | | |
| LFB Bip6,8 | 10 | 5 | | |
| LFB Bip3 PMC | 37.5 | 2.5 | | |
| LFB Bip8 PMC | 25 | 5 | | |
| LFB Tbt3 | 25 | 5 | | |
| LFB Tbt3 PMC | 37.5 | 10 | | |
| LFB Tbt6 | 12.5 | 10 | | |
| LFB Tbt6 PMC | 37.5 | 10 | | |
| LFB Tbt8 | 12.5 | 5 | | |
| LFB Tbt8 PMC | 25 | 5 | | |
| LFB Tbt6,8 | 25 | 5 | | |
| LFB Nal6 | 20 | 75 | 2.2 | 4.4 |
| LFB Nal6 PMC | 25 | 20 | 2.8 | 17.8 |
| LFB Nal6,8 | 10 | 20 | 2.8 | 4.9 |
| LFB Nal8 | 10 | 50 | 3 | 4.7 |
| LFB Nal8 PMC | 20 | 10 | 6.96 | 18.86 |
| LFB NPS-O6 | 20 | 100 | 2.8 | 4.1 |
| LFB NPS6 | 23 | 50 | 4.2 | 5.9 |

In the above table,
Bip = biphenylalanine
Tbt = tri-tert-butyltryptophan
Nal = 2-naphtylalanine
NPS = ortho-nitrophenylsulfinyl
NPS-O = ortho-nitrophenylsulfonyl
PMC = 2,2,5,7,8-pentamethylchroman-6-sulphonyl
All peptides are LFB 17-31 and modifications thereof.

EXAMPLE 8

Experiments were performed to investigate the effect of PMC and varying peptide length on anti-tumor activity and toxicity (hemolytic activity).

The results of these experiments are presented in Table 10 below.

TABLE 10

| | Meth A IC$_{50}$ (μM) | | RBC EC$_{50}$ (μM) | | Selectivity |
| --- | --- | --- | --- | --- | --- |
| Peptide | −PMC | +PMC | −PMC | +PMC | +PMC |
| LFB 14-31 A$_{2,6,10,17}$ | 165 | 15 | >440 | 118 | 8 |
| LFB 14-30 A$_{2,6,10,17}$ | >227 | 14 | >454 | 184 | 13 |
| LFB 14-29 A$_{2,6,10}$ | >235 | 18 | >469 | 367 | 20 |
| LFB 14-28 A$_{2,6,10}$ | >248 | 12 | >438 | >438 | >36 |

The presence of a PMC group on one or more of the tryptophan residues of an LFB peptide significantly increased its anti-tumor activity and to a lesser extent its hemolytic activity. Surprisingly it was found that by reducing the length of the peptide the selectivity, i.e. the anti-tumor verus the hemolytic activity of the peptide increased.

EXAMPLE 9

Modified peptides were prepared to investigate the effect of increasing the number of tryptophan residues in margainin derived active peptides. The results of these modifications are shown in Table 11 below which has MIC values for typical bacteria and shows anti-tumor activity by the μg/ml of peptide required to kill 50% of Meth A cells.

TABLE 11

| Peptides | MIC *E. coli* (μg/ml) | MIC *S. aureus* (μg/ml) | Meth A IC 50 (μg/ml) |
| --- | --- | --- | --- |
| Mag 2 | 20 | >100 | 100 |
| Mag 2 W 19 | 7.5 | 10 | 9 |
| Mag 2 W 6,8 | >100 | >100 | |
| MSI 24 | 5 | 5 | >100 |
| MSI 24 W7 | 5 | 5 | 26 |
| MSI 24 W11 | 5 | 2.5 | 24 |
| MSI 20 | | | >100 |
| MSI 20 W6 | * | * | 22 |
| Tosmag | 8 | 8 | 18 |
| Tosmag W16 | 10 | 5 | |
| Tosmag W12,16 | 5 | 10 | |
| Tosmag W6,12,15,17 | 15 | 10 | 23 |
| Tosmag W5,9,13,16,20 | >50 | >50 | 23 |

Mag 2:
(SEQ ID NO: 28)
NH$_2$-Gly-Ile-Gly-Lys-Phe-Leu-His-Ser-Ala-Lys-Lys-Phe-Gly-Lys-Ala-Phe-Val-Gly-Glu-Ile-Met-Asn-Ser-COOH.

Tosmag:
(SEQ ID NO: 29)
NH$_2$-Gly-Ile-Gly-Lys-Phe-Leu-Lys-Lys-Ala-Arg-Lys-Phe-Gly-Arg-Ala-Phe-Val-Arg-Ile-Leu-Lys-Lys-Gly-COOH.

MSI24:
(SEQ ID NO: 30)
NH$_2$-Lys-Met-Ala-Ser-Lys-Ala-Gly-Lys-Ile-Ala-Gly-Lys-Ile-Ala-Lys-Val-Ala-Leu-Lys-Ala-Leu-NH$_2$.

MSI20:
(SEQ ID NO: 31)
NH$_2$-Lys-Val-Ala-Leu-Lys-Ala-Leu-Lys-Val-Ala-Leu-Lys-Ala-Leu-Lys-Val-Ala-Leu-Lys-Ala-Leu-NH$_2$.

For peptides having only moderate anti-tumor activity, the replacement of one residue with tryptophan significantly increases activity.

Tosmag is already highly cytotoxic and it is not surprising that activity is not significantly enhanced by substitution with tryptophan, as it is replacing one or more phenylalanine residues which are themselves bulky and lipophilic.

Clearly, increasing the bulk and lipophilicity of the peptide too much can be counterproductive. This may be due to the fact that important residues are replaced or the fact that there is a limit on how bulky/lipophilic the side chains of the peptide should be.

EXAMPLE 10

Methods for the Preparation of Peptide Esters

Transesterification from Resin

Fully protected peptide esters can be obtained by base catalysed transesterification from SASRIN™ and Merrifield-like resins. Good yields have been obtained with methanol and benzyl alcohol. The best results were obtained employing either KCN2, or LiBr/DBU as catalyst.

Standard procedure for KCN-catalysed transesterification:

The peptide resin and the solvent employed have to be dried carefully before use, all have to withstand prolonged KCN-treatment. Transesterification will occur, even if the solubility of KCN is low; residual salt did not disturb. The peptide resin is suspended in a mixture of the desired alcohol and the cosolvent, e.g. dimethylacetamide, (usually 1:1, 10 ml/g resin). After 30 min sufficient solid KCN is added, so that a 0.08 M solution is obtained (or at least saturation). After stirring for 24 hours, the resin is filtered off and washed with the cosolvent. The catalyst must be destroyed immediately, e.g. by rigourously shaking the filtrate with sufficient solid anhydrous $FeCl_2$. Iron blue will flock out, it is left to settle for approx. 30 min and filtered off. The filtrate may remain greenish. Further work-up depends on the solubility of the product, but it should be treated with water: After removing alcohol and cosolvent, the residue is taken up in an organic solvent, e.g. ethyl acetate or chloroform, for further aqueous extraction to remove salts.

Direct Benzyl Esterification of N-Acylpeptides (p-Hydroxyphenyl)benzylmethylsulfonium derivatives (HOBMX) easily generate benzyl cations, which convertes N-terminal- and side chain-protected peptides into thier benzyl esters without racemization.

General procedure: The peptide and potassium carbonate are dissolved in dichloromethane, and the mixture is stirred at room temperature. After 10 min, HOBMC1 is added to the solution and it is stirred for 8 hours. Inorganic salts in the reaction mixture are filtered off and the filtrate evaporated in vacuo. The residue is dissolved in toluene and washed with 0.5 M NaOH aqueous solution and then with water. The organic layer is dried over anhydrous sodium sulfate and the filtrate evaporated in vacuo.

EXAMPLE 11

A series of further modified peptides were prepared based on murine lactoferrin. In the following data (see Table 12), LFM refers to residues 17-31 of murine lactoferrin. Shorter peptides are indicated by the notation wherein e.g. LFM 17-24 represents an 8-mer peptide corresponding to the amino acids at positions 17 through to 24 of murine lactoferrin.

The murine equivalent of LFB is generally much less active than its bovine equivalent, however, by modifying the peptide in accordance with the present invention peptides with greatly enhanced anti-bacterial activity can be prepared. LFM does not possess a tryptophan residue at position 8, unlike its more active bovine counterpart. The inventors have identified this residue as important to the activity of LFB and thus this substitution of asparagine for tryptophan has been made. This substitution alone did not significantly enhance the activity against the bacterial strains tested. Activity could be further enhanced by substituting one or both of the anionic residues at positions 1 and 9 with unchanged alanine or more preferably a cationic residue such as arginine.

By incorporating further bulky/lipophilic residues, e.g. a tyrosine residue at position 13 in place of the less bulky valine and/or by modifying the tryptophan residue by incorporation of the more bulky PMC group, peptides with good antimicrobial activity could be made.

In addition it was surprisingly found that shorter peptides based on fragments of LFM when modified to introduce additional bulky/lipophilic amino acids e.g. tryptophan or tyrosine and to increase the overall charge of the peptide by replacing native residues with cationic residues such as arginine were particularly effective.

TABLE 12

| Peptide | MIC E. coli μg/ml | MIC S. aureus μg/ml | % Hemolysis 10 μg/ml | % Hemolysis 100 μg/ml |
|---|---|---|---|---|
| LFM | >1000 | >1000 | 2.3 | 3.1 |
| LFM W8 | >1000 | 1000 | 2.6 | 4.8 |
| LFM W8 Y13 | >1000 | >1000 | | |
| LFM A1 W8 | 750 | >1000 | 2.4 | 3 |
| LFM A1 W8 Y13 | 500 | >1000 | | |
| LFM A9 W8 | >1000 | >1000 | 2.5 | 3.5 |
| LFM A9 W8 Y13 | >1000 | >1000 | | |
| LFM A1, 9 W8 | 200 | >1000 | 2.8 | 3.7 |
| LFM A1, 9 W8 Y13 | 150 | >1000 | | |
| LFM R1, W8 | 75 | 500 | 2.8 | 3.48 |
| LFM R1 W8 PMC | >200 | >200 | | |
| LFM R1 W8 Y13 | 50 | 50 | | |
| LFM R9 W8 | 500 | >1000 | 3.1 | 4.59 |
| LFM R9 W8 PMC | 20 | 50 | | |
| LFM R9 W8 Y13 | 150 | 1000 | | |
| LFM R1, 9 W8 | 25 | 75 | 3.69 | |
| LFM R1, 9 W8 PMC | 10 | 5 | | 4.9 |
| LFM R1, 9 W8 Y13 | 25 | 50 | | |
| LFM A1 R9 W8 Y13 | 50 | 200 | | |
| LFM 17-24 R1,2,8 W3,7Y4NH2 | 5 | 2.5 | | |
| LFM 17-24 R1,2,8 W3,7Y4NH2 PMC | 25 | 1-2.5 | | |
| LFM 18-24 R1,7 W2,3,6Y5NH2 | 10 | 0.5-1 | | |
| LFM 17-25 A4R2,8,9W3,7Y1NH2 | 10 | 5 | | |
| LFM 17-25 A4R2,8,9W3,7Y1NH2 PMC | 20 | 2.5 | | |
| LFM 17-26 A7R2,8,9W3,4, 10Y1NH2 | 10 | 2.5 | | |

EXAMPLE 12

Table 13 below illustrates the effect of further chemical modifications which provide peptides in accordance with the invention.

TABLE 13

| Peptide | MIC E. coli μg/ml | MIC S. aureus μg/ml | % Hemolysis 10 μg/ml | % Hemolysis 100 μg/ml | MethA IC50 μg/ml |
|---|---|---|---|---|---|
| LFB | 50 | 100 | 2.6 | 3.47 | 500 |
| LFB PMC | 10 | 10 | 2.8 | 4.4 | 120 |
| LFB PMC6 | 10 | 10 | 3.4 | 6 | 148 |
| LFB PMC8 | 18 | 10 | 3.6 | 9.79 | 150 |
| LFB 18-31 | 80 | 200 | | | |
| LFB 18-31 PMC | 10 | 10 | | | |
| LFB 19-31 | 200 | >250 | | | |
| LFB 19-31 PMC | 10 | 15 | | | |
| LFB 20-28 A4 | >100 | >100 | 0 | 1.68 | 500 |
| LFB 20-28 A4 FMOC | | | | | 120 |
| LFB 20-28 A4 FMOC PMC | | | | | 35 |
| LFB 20-28 A4 PMC | 15 | | 3.9 | 12.6 | 110 |
| LFB 20-29 | 60 | >100 | 1.75 | 2.74 | 500 |
| LFB 20-29 FMOC | 5 | 10 | 10.3 | 28.2 | 140 |
| LFB 20-29 FMOC PMC | | | 22.5 | 60.2 | 50 |
| LFB 20-29 PMC | 10 | 10 | 5.6 | 18.9 | 160 |
| LFB 20-30 | 40 | >100 | 2.16 | 3.1 | |
| LFB 20-30 PMC | 15 | 10 | 5.54 | 15.8 | |
| LFB 20-31 | 100 | 200 | | | |
| LFB 20-31 PMC | 10 | 10 | | | |
| LFB A1 | 70 | >200 | | | |
| LFB A1 PMC | 8.75 | 10 | | | |
| LFB A2 | 80 | >200 | | | |
| LFB A2 PMC | 11.25 | 10 | | | |
| LFB A3 | 25 | 100 | | | 500 |
| LFB A3 PMC | 7.5 | 7.5 | 2 | 3.67 | 130 |
| LFB A4 | 7.0 | >200 | | | |
| LFB A4 PMC | 15 | 27.5 | | | |
| LFB A5 | 120 | >200 | | | |
| LFB A5 PMC | 10 | 50 | | | |
| LFB A6 | >200 | >200 | 2.78 | 3.27 | |
| LFB A6 PMC | 25 | 17.5 | | | |
| LFB A7 | 30 | 150 | | | 500 |
| LFB A7 PMC | 20 | 7.5 | 2.1 | 3.8 | 88 |
| LFB A8 | >200 | >200 | 2.8 | 3.45 | 500 |
| LFB A8 FMOC | 60 | 10 | 2.87 | 7.79 | |
| LFB A8 FMOC PMC | | | 6.75 | 45.4 | |
| LFB A8 PMC | 15 | 17.5 | | | 275 |
| LFB A9 | 55 | >200 | | | |
| LFB A9 PMC | 10 | 12.5 | | | |
| LFB A10 | 140 | >200 | | | |
| LFB A10 PMC | 20 | 22.5 | | | |
| LFB A11 | 70 | >200 | | | |
| LFB A11 PMC | 22.5 | 22.5 | | | |
| LFB A12 | 50 | >200 | | | |
| LFB A12 PMC | 20 | 20 | | | |
| LFB A13 | 50 | >200 | | | |
| LFB A13 PMC | 15 | 15 | | | |
| LFB A14 | 25 | 160 | | | 500 |
| LFB A14 PMC | 15 | 17.5 | | | 100 |

Unless otherwise indicated, LFB represents LFB 17-31.

EXAMPLE 13

Table 14 below illustrates the antibacterial activity as well as toxicity (% hemolysis) data for further peptides according to the invention.

TABLE 14

| Peptide | MIC E. coli μg/ml | MIC S. aureus μg/ml | % Hemolysis 10 μg/ml | % Hemolysis 100 μg/ml | MethA IC$^{50}$ μg/ml |
|---|---|---|---|---|---|
| LFB F4 | 20 | 200 | 2.4 | 3.2 | |
| LFB F4 PMC | 20 | 20 | | | |
| LFB F4K1 | 20 | 200 | | | |
| LFB F4K1 PMC | 10 | 10 | | | |
| LFB K1 | 60 | 100 | | | |
| LFB K1 PMC | 10 | 10 | | | |
| LFB W3 | 20 | 20 | 2.3 | 3.8 | |
| LFB W3 PMC | >50 | 10 | 3.55 | 17.35 | |
| LFB W3, 14 | 10 | 10 | 3.1 | 5.1 | |
| LFB W3, 14 PMC | 20 | 20 | | | |
| LFB W3, 7, 14 | 20 | 20 | 4.02 | 66.1 | |
| LFB W3, 7, 14 PMC | 30 | 20 | 18.1 | 85.9 | |
| LFB W4, 10 | 5 | 10 | 4.45 | 27.8 | 500 |
| LFB W4, 10 PMC | 20 | 20 | 2.27 | 14.2 | 110 |
| LFB W14 | 20 | 25 | 3 | 4.1 | |
| LFB W14 PMC | 25 | 10 | | | |

EXAMPLE 14

Antibacterial peptides which are active against bacterial strains which have been shown to demonstrate resistance to other antibiotics are potentially very useful peptides. Table 15 below gives the antibacterial activity and toxicity data for some preferred peptides of the invention. MRSA is methicillin resistant *S. aureus* and MRSE is methicilin resistant *S. epidermidis*.

In Table 15, LFB=LFB 17-31 unless otherwise indicated. The previously identified one and three letter codes are used and in addition, the following N-terminal modifying groups are represented:
Bz=benzyl
CHx=cyclohexyl
Ad=adamantyl

TABLE 15

| Peptide | MIC E. coli μg/ml | MIC E. coli μM | MIC S. aureus μg/ml | MIC S. aureus μM | MIC MRSA μg/ml | MIC MRSA μM | MIC MRSE μg/ml | MIC MRSE μM | EC 50 μg/ml | EC 50 μM |
|---|---|---|---|---|---|---|---|---|---|---|
| Bz LFB | | | | | | | | | | |
| Chx LFB | | | >20 | >9.2 | 2.5-5 | 1.1-2.3 | | | | |
| Ad LFB | | | 7.5-10 | 3.3-4.5 | 2.5-5 | 1.1-2.2 | | | | |
| LFB PMC 6 | 10.0 | 4.3 | 2.5 | 1.1 | 2.5 | 1.1 | | | >1000 | >429 |
| LFB A3 PMC | 7.5 | 3.4 | 5.0 | 2.2 | | | | | >1000 | >449 |
| LFB A7 PMC | 20.0 | 8.8 | 15.5-20 | 6.8-8.8 | ≥20 | ≥8.8 | 17.5 | 7.7 | >1000 | |
| LFB A3, 7 | | | >20 | >10.5 | 17.5-20 | 9.2-10.5 | 5.0 | 2.6 | >1000 | >525 |
| LFB A3, 7 PMC | | | 2.5 | 1.2 | 2.5 | 1.2 | 2.5 | 1.2 | >1000 | >461 |
| LFB W3, 14 | 10.0 | 4.5 | 2.5 | 1.1 | 2.5 | 1.1 | 2.5 | 1.1 | >1000 | >453 |
| LFB retro PMC | 10.0 | 4.3 | 5-7.5 | 2.1-3.2 | | | | | >1000 | >429 |
| LFB enantio PMC | 7.5 | 3.2 | 2.5-5 | 1.1-2.1 | 2.5-5 | 1.1-2.1 | 2.5 | 1.1 | >1000 | >429 |
| LFB 20-30 PMC | 15.0 | 8.3 | 10.0 | 5.5 | | | | | | |

TABLE 15-continued

| Peptide | MIC E. coli µg/ml | MIC E. coli µM | MIC S. aureus µg/ml | MIC S. aureus µM | MIC MRSA µg/ml | MIC MRSA µM | MIC MRSE µg/ml | MIC MRSE µM | EC 50 µg/ml | EC 50 µM |
|---|---|---|---|---|---|---|---|---|---|---|
| LFB 17-27 A3,7 R2,11 W4,10 Y1 NH2 | 10.0 | 5.9 | 2.5 | 1.5 | 0.5-1 | 0.3-0.6 | 2.5 | 1.5 | 700 ± 300 | 400 ± 200 |
| LFB 17-27 A7 M3 R2,11 W4,10 Y1 NH2 | 10.0 | 5.7 | 0.5-1 | 0.3-0.6 | | | | | 510 ± 160 | 291 ± 91 |
| LFB 17-27 A3,7 R2,11 W4,10 Y1 NH2 PMC | | | 1-2.5 | 0.5-1.3 | | | | | 43 ± 8 | 22 ± 4 |
| LFB 17-27 A7 M3 R2,11 W4,10 Y1 NH2 PMC | | | | | | | | | 40 ± 10 | 20 ± 5 |
| LFB 14-31 A2,6,10,17 | 20.0 | 8.8 | >2.5 | >1.1 | 5.0 | 2.2 | | | >1000 | >440 |
| LFB 14-31 A2,6,10,17 PMC | 20.0 | 7.9 | >2.5 | >1.0 | | | | | >1000 | >394 |
| LFB 14-31 A2,6,10,17 R4 | 30.0 | 13.1 | 20.0 | 8.8 | | | | | >1000 | >438 |
| LFB 14-31 A2,6,10,17 R4 PMC | 10.0 | 3.9 | >2.5 | >1.0 | | | | | 739 | 290 |
| LFB 14-31 A2,6,10,17 R4,11 | | | 12.5-15 | 5.6-6.7 | 2.5-5 | 1.1-2.2 | | | >1000 | >444 |
| LFB 14-31 A2,6,10,17 R4,11 PMC | | | 2.5-5 | 1.0-2.0 | 2.5-5 | 1.0-2.0 | | | 823 | 327 |
| LFB 14-31 A2,6,10,17 F7R4 | 10.0 | 4.4 | >2.5 | >1.1 | | | | | >1000 | >440 |
| LFB 14-31 A2,6,10,17 K16L14 | 10.0 | 4.4 | 10.0 | 4.4 | | | | | >1000 | >440 |
| LFB 14-31 A2,6,10,17 F7K16L14R4 | | | | | | | | | | 110 |
| LFB 14-31 A2,6,10,17 F7L14Orn5,4,8,12,15,16 | | | 2.5 | 1.2 | 2.5 | 1.2 | | | 425 | 202 |
| LFM R1, 9 W8 PMC | 10.0 | 4.4 | 1.0 | 0.4 | | | | | >1000 | >435 |
| LFM 17-24 R1,2,8 W3,7Y4NH2 | 5.0 | 3.7 | 2.5-5 | 1.8-3.7 | 1.0 | 0.7 | 2.5 | 1.8 | >1000 | >733 |
| LFM 17-24 R1,2,8 W3,7Y4NH2 PMC | 20-50 | 34-53 | 1-2.5 | 0.6-1.5 | 1-2.5 | 0.6-1.5 | 2.5 | 1.5 | 120 ± 70 | 74 ± 43 |
| LFM 18-24 R1,7 W2,3,6Y5NH2 | 10.0 | 8.3 | 0.5-1 | 0.4-0.8 | 0.5-2.5 | 0.4-2.1 | 1.0 | 0.8 | >1000 | >829 |
| LFM 17-25 A4R2,8,9W3,7Y1NH2 | 10.0 | 7.0 | 0.5-5 | 0.3-3.5 | | | | | >1000 | >697 |
| LFM 17-25 A4R2,8,9W3,7Y1NH2 PMC | 20.0 | 11.8 | 2.5 | 1.5 | | | | | 140 ± 90 | 82 ± 53 |
| LFM 17-26 A7R2,8,9W3,4, 10Y1NH2 | 10.0 | 6.2 | 1.0 | 0.6 | 2.5 | 1.5 | | | 880 ± 90 | 543 ± 56 |
| LFM 17-26 A7R2,8,9W3,4, 10Y1NH2 PMC | 200.0 | 106.0 | 2.5 | 1.3 | 2.5 | 1.3 | | | 150 ± 90 | 79 ± 48 |
| LFB Bip 3 | 12.5 | 5.9 | 2.5-5 | 1.2-2.4 | 2.5 | 1.2 | | | | |
| LFB Bip 6,8 | ≥12.5 | ≥5.8 | 3.0 | 1.4 | 2.5 | 1.2 | | | | |
| LFB Bip 3 PMC | ≤25 | ≤10.5 | 2.5 | 1.1 | 2.5-5 | 1.1-2.1 | | | | |
| LFB Bip 8 PMC | 15.0 | 6.3 | 2.5 | 1.1 | 2.5 | 1.1 | | | | |
| LFB Nal 6,8 | 10.0 | 4.8 | 20.0 | 9.6 | 5.0 | 2.4 | | | >1000 | >479 |
| LFB Tbt6 | 12.5 | 5.6 | 2.5 | 1.1 | 1-2.5 | 0.4-1.1 | 2.5 | 1.1 | >1000 | >448 |
| LFB Tbt6 PMC | 37.5 | 15.0 | 2.5-5 | 1.0-2.0 | 5.0 | 2.0 | | | 410 ± 70 | 164 ± 28 |
| LFB Tbt8 | 12.5 | 5.6 | 2.5-5 | 1.1-2.2 | 0.5-2.5 | 0.2-1.1 | 2.5 | 1.1 | >1000 | >448 |
| LFB Tbt8 PMC | 25-50 | 10-23 | 2.5-7.5 | 1.0-3.0 | 5.0 | 2.0 | | | 290 ± 70 | 116 ± 28 |
| LFB Tbt6,8 | 25-37.5 | 12-18 | 2.5 | 1.2 | 5.0 | 2.3 | 2.5 | 1.2 | 230 ± 30 | 107 ± 14 |
| LFB Tbt3 | 25.0 | 11.1 | 2.5 | 1.1 | 2.5 | 1.1 | | | 500 ± 40 | 223 ± 18 |

EXAMPLE 15

Table 16 below gives MIC values for a variety of peptides which incorporate a proportion of D-amino acids.

TABLE 16

| Peptide | Sequence* | MIC µg/ml E. coli | MIC µg/ml S. aureus | MIC µg/ml MRSA |
|---|---|---|---|---|
| LFM 17-27 A7R2,8,9W3,4,10Y 1 NH2 | TYR-ARG-ALA-TRP-ARG-TRP-ALA-TRP-ARG-TRP-ARG-CONH2 (SEQ ID NO: 32) | 10 | 2.5 | |
| | tyr-ARG-ala-TRP-arg-TRP-ala-TRP-arg-TRP-arg-CONH2 (SEQ ID NO: 33) | 7.5 | 7.5 | 2.5 |
| | tyr-arg-ala-TRP-ARG-TRP-ala-TRP-ARG-TRP-ARG-CONH2 (SEQ ID NO: 34) | 7.5 | 5 | 2.5 |
| LFM 18-24 R1,7W2,3,6Y5 NH2 | ARG-TRP-TRP-ARG-TYR-TRP-ARG-CONH2 (SEQ ID NO: 35) | 10 | 1 | |
| | arg-TRP-trp-ARG-tyr-TRP-arg-CONH2 (SEQ ID NO: 36) | 7.5 | 5 | 2.5 |
| | arg-trp-TRP-ARG-TYR-trp-arg-CONH2 (SEQ ID NO: 37) | 7.5 | 5 | 2.5 |

*Upper case letters represents L-amino acids, lower case letters denote D-amino acids

EXAMPLE 16

Cytotoxicity of the Peptides of the Invention

The cytotoxic effect of the peptides on different murine and human tumor cells were measured using the MTT method (Mosmann et al., J. Immunol. (1986) 136, 2348-2357).

MTT is a soluble tetrazolium salt yielding a yellow solution when prepared in media or salt solutions lacking phenol red. Dissolved MTT is converted to an insoluble purple formazan by cleavage of the tetrazolium ring by dehydrogenase enzymes. This water insoluble formazan can be solubilized using isopropanol or other solvents and the dissolved material is measured spectrophotometrically. The absorbance was measured as a function of concentration of converted dye.

The conversion of the soluble dye to the insoluble purple formazan is utilized in assays for measurement of cell proliferation. Active mitochondrial dehydrogenases of living cells cause this change, while dead cells do not.

We used this assay to measure the degree of cell death caused by peptides.

Cells:

Cells were maintained in RPMI-1641 medium containing 10% FBS, 1% L-glutamine and 0.1% penicillin and streptomycin. Cells to be used in the assay were grown to confluency, trypsinated and split to single cell suspension, counted and centrifuged at 1500 rpm for 10 min. The cell pellet was resuspended to a concentration of 4×105 cells/ml in RPMI-1640 without FBS and L-glutamine (assay-medium). 100 ml of cell suspension was transferred to each well on a 96-well microtiter plate. The cells were stimulated by adding 100 ml of various concentrations of peptides diluted with assay medium to each well. The final concentrations of peptide were for example: 5, 10, 20, 40, 60, 80, 100, and 200 mg/ml. Because there is a twofold dilution upon adding the peptide solution to the wells containing the cell suspension, the peptide solution had to be made twofold concentrated. As a negative control only medium was added to the cells, and as a positive control (100% killing) 1% triton X-100 was added. Following an incubation period of 4 h., 20 ml MTT dissolved in PBS at a concentration of 5 mg/ml was added to each well, and the plate was incubated further for 2 h. 130 ml of the supernatant were then removed and 100 ml acid alcohol (0.04-0.1 N HCl in isopropanol) added to each well to dissolve the dark blue crystals. The plate was placed on a shaker for 1 h and read spectrophotometrically at 590 nm in a microtiterplate reader using the Softmaxâ program.

Hemolytic Assay

The hemolytic activities of the peptides were determined using fresh human red blood cells. 8 ml blood was taken from a healthy person. 4 ml blood was transferred to a polycarbonate tube containing heparin to a final concentration of 10 U/ml, and the remaining 4 ml blood was transferred to a glass tube containing EDTA with final concentration of 15% EDTA. The erythrocytes were isolated from heparin-treated blood by centrifugation in 1500 rpm for 10 min and washed three times with phosphate-buffered saline (PBS) to remove plasma and buffy coat. The cell pellet was resuspended in PBS to make the final volume of 4 ml. The peptide was diluted to a concentration of 2 mg/ml and 0.1 mg/ml. The peptide was further diluted to the concentrations as stated in Table 1. For each tube PBS was added first, then RBCs and peptide solutions. The hematocrit in the blood treated with EDTA was determined after 30 min with Sysmex K-1000, and the resuspended RBCs were diluted into 10% hematocrit. RBCs in PBS (1%) with and without peptides (Table 18) were incubated in a shaker at 37° for 1 hour and then centrifuged at 4000 rpm for 5 min. The supernatant were carefully transferred to new polycarbonate tubes and the absorbance of the supernatant was measured at 540 nm. Baseline hemolysis was hemoglobin released in the presence of PBS, and 100% hemolysis was hemoglobin released in the presence of 0.1% Triton X-100.

TABLE 17

| Tube No. | Final peptide concentration (µg/ml) | Peptide or Triton X-100 (µl) | Red blood cells (µl) | PBS (µl) | Total Volume (µl) |
|---|---|---|---|---|---|
| 1 (2 mg/ml peptide) | Neg. control | | 70 | 630 | 700 |
| 2 (2 mg/ml peptide) | Pos. control | 7 | 70 | 623 | 700 |
| 3 (2 mg/ml peptide) | 1000 | 250 | 50 | 200 | 500 |
| 4 (2 mg/ml peptide) | 500 | 125 | 50 | 325 | 500 |
| 5 (2 mg/ml peptide) | 100 | 35 | 70 | 595 | 700 |
| 6 (2 mg/ml peptide) | 50 | 17.5 | 70 | 612.5 | 700 |
| 7 (0.1 mg/ml peptide) | 10 | 70 | 70 | 560 | 700 |
| 8 (0.1 mg/ml peptide) | 1 | 7 | 70 | 623 | 700 |

EXAMPLE 17

Solid Phase Peptide Synthesis

Initially the lactoferricin B used was a gift from Wayne Bellamy (NutritiOnal Science Laboratory, Morinaga Milk industry Co. Ltd, Japan). All the other peptides were synthesized on a 9050 Millipore Automatic Peptide Synthesizer. Generally, in solid phase synthesis, peptide chains are assembled from the carboxy terminus to the amino acid terminus. The first (C-terminal) amino acid was covalently attached to an insoluble support (the resin) by a linker (4-hydroxymethyl-phenoxyacetic acid). The remaining amino acids were added, one by one, until the peptide sequence was completed.

Using the Fmoc method, the α-amino end of the amino acid was temporary protected by the base labile 9-fluorenyl-methoxycarbonyl (Fmoc) group. Not only the α-amino group of the amino acid was protected. Some of the amino acids have reactive side chains which are necessary to protect during the synthesis to prevent side reactions. These protecting groups, except for cysteine, were acid labile and cleaved upon treatment with TFA (trifluoroacetic acid) and scavengers (see below).

Prior to the synthesis, to the solid support PEG-PS (Poly Ethylene Glycol-Poly Styrene resin) was added a small volume of DMF (dimethylformamide) and left to swell for 30 minutes. Packed into a column, the Fmoc group was removed by treatment with a 20% piperidine solution in DMF. The incomming protected amino acid was now able to bind to the free amino end of the resin-linked amino acid with its carboxy end. However, coupling or acylation does not occur spontaneously, the carboxylate must be activated. This was achieved by the use of preactivated amino acids, such as pentafluorophenyl (Pfp) esters, or amino acids with free carboxylates able to react with the coupling reagent HATU (O-(7-azabenzotriazol-1-yl)-1,1,3,3-tetramethyl-uronium hexafluorophosphate) in situ. Using Pfp esters, 1.3 eq. of HOBt (1-hydroxy-benzotriazole) was added to catalyse the reaction, while when using the coupling reagent HATU, the reaction was base catalysed with 2.4 eq. of DIPEA (diisopropylethylamine). A four-fold excess of activated amino acids was generally employed. The amino acids were dissolved in the activator solution in sufficient quantity, as calculated by the Express-Peptide program. Amino acids were then delivered to the support-bound amino acid/peptide with fully deprotected α-amine group, and recycled through the loop mixed to achieve peptide bond formation. The capacity of the resins used scaled from 0.15 to 0.23 mmol/g, meaning available binding sites for the incomming amino acids, wherefrom the amount of activator equivalents was calculated. The standard coupling cycle for amino acids was 30 minutes, with the exception of arginine, isoleucine, threonine, tyrosine, valine, and the amino acids coupled thereafter, requiring 60 minutes. Extended coupling times for these amino acids were chosen because of their large side chains which are known to cause sterical hindrance during the coupling reaction. Once coupling was complete, the excess amino acid solution and reaction by-products were removed by washing with DMF. The next cycle begun with deblocking of the α-amino group of the N-terminal amino acid. The process of α-amino group deblocking followed by coupling was repeated for as many cycles as necessary to assemble the desired peptide.

After the synthesis was complete, the column material was transferred to a funnel and washed with methanol (3×) and dichloromethane (2×). The cleavage of the acid labile side chain protecting groups and cleavage of the peptides from the solid support was achieved using a mixture of 2% anisol, 2% ethandithiol, 2% water and 2% phenol in TFA, and with cleavage times of no more than four hours. The solid support was then removed by filtration, the filtrate concentrated under a high vacuum and the peptide precipitated in diethyl ether. The ether solution containing TFA was removed using a pasteur pipette, and the peptide was washed several times with diethyl ether and dried under a high vacuum.

Amino Acid Derivatives:

Fmoc-L-Ala-OPfp
Fmoc-L-Arg(Pmc)-OPfp
Fmoc-L-Cys(Acm)-OPfp
Fmoc-L-Gln-OPfp
Fmoc-L-Glu(OtBu)-OPfp
Fmoc-L-Gly-OPfp
Fmoc-L-Ile-OPfp
Fmoc-L-Leu-OPfp
Fmoc-L-Lys(tBoc)-OPfp
Fmoc-L-Met-OPfp
Fmoc-L-Phe-OPfp
Fmoc-L-Ser(tBu)-OPfp
Fmoc-L-Trp-OPfp
Fmoc-L-Tyr(tBu)-OPfp
Fmoc-L-Val-OPfp Amino acid derivatives: Amino acid derivatives were purchased from either Bachem, MilliGen/Biosearch (Division of Millipore) or PerSeptive Biosystems. Phenol was purchased from Fluka, and anisole was purchased from Sigma. DMF, PIP, DIPEA TFA and PEG-PS resin were all purchased from PerSeptive Biosystems.

EXAMPLE 18

Table 18 below shows the anti-tumor activity and toxic data for a LFB 14-31 derivative incorporating either of two non-genetic bulky and lipohilic amino acids in place of a Trp or incorporating a group (Pmc) which increases the bulk and lipophilicity of one of the naturally occurring Trp or Phe residues.

TABLE 18

| Variable Peptide | RBC $EC_{50}$ (μM) | Meth A $EC_{50}$ (μM) |
|---|---|---|
| LFB14-31A2,6,10,17 | >440 | 165 |
| LFB14-31A2,6,10,17Bip4 | 336 | 23.4 |
| LFB14-31A2,6,10,17Pmc | 165 | 12.8 |
| LFB14-31A2,6,10,17Tbt9 | 25.6 | 9.5 |

The presence of either of the three non-genetically modifications on a LFB 14-31 derivative significantly increased its anti-tumor activity. The Tbt modified peptide however possesed the highest hemolytic activity among the three modified analogs tested.

EXAMPLE 19

Table 17 below shows the anti-bacterial and anti-tumor activity and toxicity of further peptides according to the invention. In particular, the substitutions show how replacement of tryptophan may result in peptides with advantageously low toxicity (activity against red blood cells and normal fibroblasts).

TABLE 19

| Substitution | Peptide | MethA $IC_{50}$ (μM) (4 h) | Mic E- coli (μM) | Mic S. Aureus (μM) | RBC $EC_{50}$ (μM) | Fibroblast $IC_{50}$ (μM) |
|---|---|---|---|---|---|---|
| Alanine | LFB 14-31$A_{2,6,10,17}F_7K_{16}L_{14}R_4$ | 6.6 | 2/4 | 2 | 110 | 17 |
| W3→A3 | LFB 14-31$A_{2,3,6,10,17}F_7K_{16}L_{14}R_4$ | 24.1 | 15 | 10 | >463 | 190 |
| W9→A9 | LFB 14-31$A_{2,6,9,10,17}F_7K_{16}L_{14}R_4$ | 16.2 | 10 | 5 | 382 | 46.3 |
| W11→A11 | LFB 14-31$A_{2,6,10,11,17}F_7K_{16}L_{14}R_4$ | 11.1 | 10 | >2.5 | 278 | 46.3 |
| W9,11→A9,11 | LFB 14-31$A_{2,3,6,9,10,11,17}F_7K_{16}L_{14}R_4$ | 110.1 | 30 | 30 | >489 | >489 |
| Lysine | | | | | | |
| W3→K3 | LFB 14-31$A_{2,6,10,17}F_7K_{3,16}L_{14}R_4$ | 230 | | | >451 | 230 |
| W9→K9 | LFB 14-31$A_{2,6,10,17}F_7K_{9,16}L_{14}R_4$ | 13.5 | 30 | 10 | >451 | 58.7 |
| W11→K11 | LFB 14-31$A_{2,6,10,17}F_7K_{11,16}L_{14}R_4$ | 7.9 | 5 | <2.5 | >451 | 30.7 |
| W9,11→K9,11 | LFB 14-31$A_{2,6,10,17}F_7K_{9,11,16}L_{14}R_4$ | >300 | | | >463 | >463 |
| Isoleucine | | | | | | |
| W3→I3 | LFB 14-31$A_{2,6,10,17}F_7I_3K_{16}L_{14}R_4$ | 9 | 2/4 | 2/4 | 323 | 20 |
| W9→I9 | LFB 14-31$A_{2,6,10,17}F_7I_9K_{16}L_{14}R_4$ | 12 | 5 | <1 | | 26 |
| W11→I11 | LFB 14-31$A_{2,6,10,17}F_7I_{11}K_{16}L_{14}R_4$ | 6 | 2/5 | <1 | | 15 |
| W9,11→I9,11 | LFB 14-31$A_{2,6,10,17}F_7I_{9,11}K_{16}L_{14}R_4$ | 22 | | | | 26 |
| W3,9→I3,9 | LFB 14-31$A_{2,6,10,17}F_7I_{3,9}K_{16}L_{14}R_4$ | 36 | 5 | 5 | >470 | 108 |

TABLE 19-continued

| Substitution | Peptide | MethA IC$_{50}$ (μM) (4 h) | Mic E-coli (μM) | Mic S. Aureus (μM) | RBC EC$_{50}$ (μM) | Fibroblast IC$_{50}$ (μM) |
|---|---|---|---|---|---|---|
| W3,11→I3,11 | LFB 14-31A$_{2,6,10,17}$F$_7$I$_{3,11}$K$_{16}$L$_{14}$R$_4$ | 16 | 2.5 | 5 | 413 | 45 |
| W3,9,11→I3,9,11 | LFB 14-31A$_{2,6,10,17}$F$_7$I$_{3,9,11}$K$_{16}$L$_{14}$R$_4$ | 47 | 2.5 | 10 | >487 | 280 |
| F7→A7 | LFB 14-31A$_{2,6,10,17}$F$_7$K$_{16}$L$_{14}$R$_4$ | 34.6 | 15 | 10 | >455 | 288.9 |

EXAMPLE 20 a) Syngenic Balb/c mice were used as a model system. The mice were inoculated with cells of A20 B-cell lymphoblast (5×10$^6$) though subcutaneous injection. Tumours were allowed to grow to a size of 20-30 mm$^2$. The mice were randomised into groups of 6-8 and the tumors were treated directly with a peptide selected from Table 20 below. The treatment involved injection of 50 μl of a peptide solution, providing 0.5 mg of peptide once a day for three consecutive days.

Figure 11:
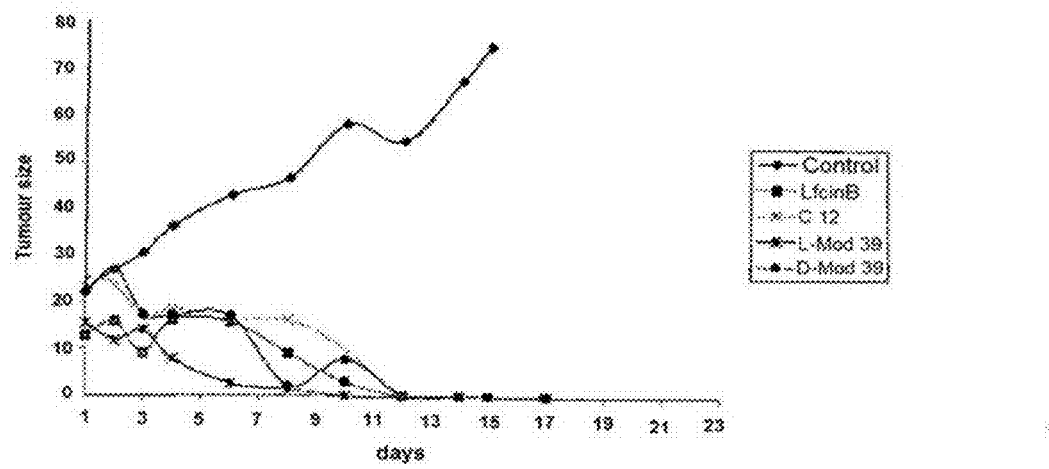
FIG. 11 is a graph showing the progress of A20 B-cell lymphoma in Balb/c mice upon treatment of different peptides.

Tumour progression was followed by measuring the size of the tumor. As can be seen from FIG. 11, the control tumor (untreated) displayed a steady increase in size over 15 days. Treatment of the tumors with the peptides of Table 20 caused a regression in tumor size, leading to an apparently complete disappearance of the tumor.

TABLE 20

Peptides

Figure 12:
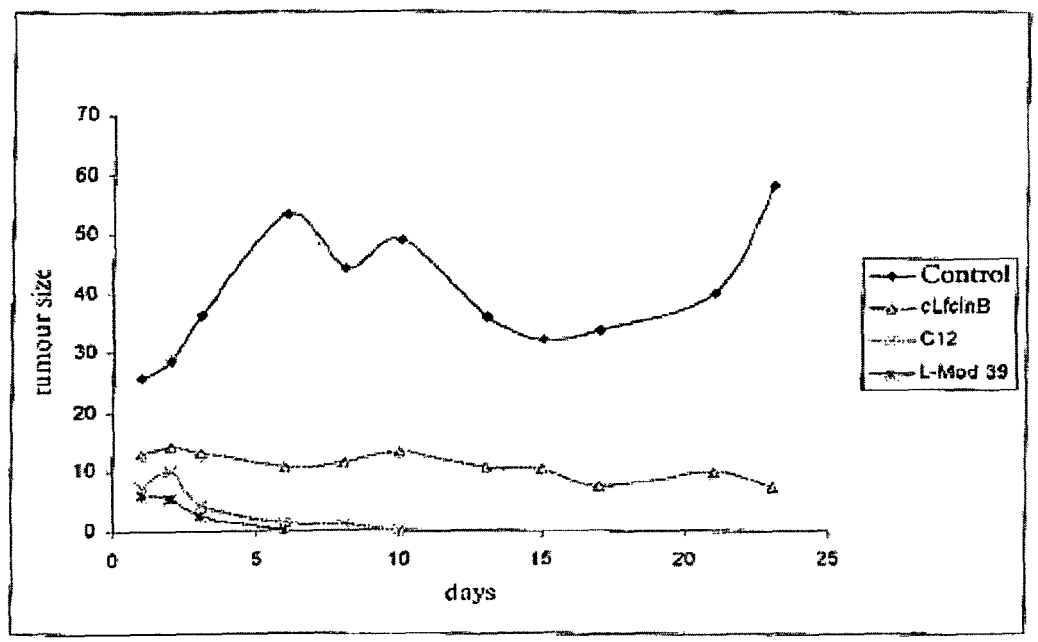
FIG. 12 is a graph showing the development of tumors in mice re-inoculated with A20 cells one month after successful treatment of A20 solid tumors with different peptides.

| Name | Sequence | |
|---|---|---|
| LfcinB: | H$_2$N-FKCRRWQWRMKKLGAPSITCVRRAF-COOH | (SEQ ID NO: 38) |
| Model 28: | H$_2$N-KAAKKAAKAbipKKAAKbipKKAA-COOH | (SEQ ID NO: 39) |
| Model 39: | H$_2$N-WKKWdipKKWK-COOH (D and L form) | (SEQ ID NO: 40) |
| C12: | H$_2$N-KAAKKAbipKAAKAbipKKAA-COOH | (SEQ ID NO: 41) | bip = biphenylalanine; dip = diphenylalanine b) Mice in which a A20 B-cell lymphoblast tumor had successfully been eradicated as described above were re-inoculated with 5×10$^6$ cells of A20 B-cell lymphoma tumor. Untreated mice served as a negative control. No further administration of peptides or any other anti-tumor agents took place. The results are shown in FIG. 12.

When untreated mice were inoculated with tumor cells, significant tumor growth occurred. When mice previously treated with cLfinB were re-inoculated with tumor cells, some initial tumor growth occurred, but at day 1 the tumor was significantly smaller than the tumor in the control mice, and no further growth occurred. Some tumor regression was even noted.

Inoculation of mice previously treated with C12 or L-Mod 39 with tumor cells initially resulted in the appearance of a very small tumor, which completely disappeared after 6 or 10 days respectively.

EXAMPLE 21

Figure 13:
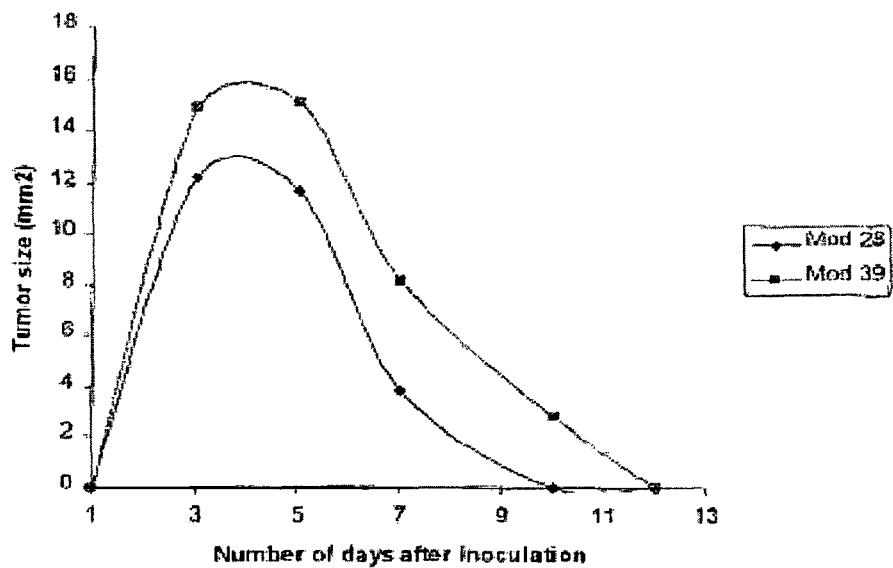
FIG. 13 is a graph showing the effect of re-inoculating A-20 cells in animals that had been successfully treated with Mod 28 or Mod 39.
Figure 14:
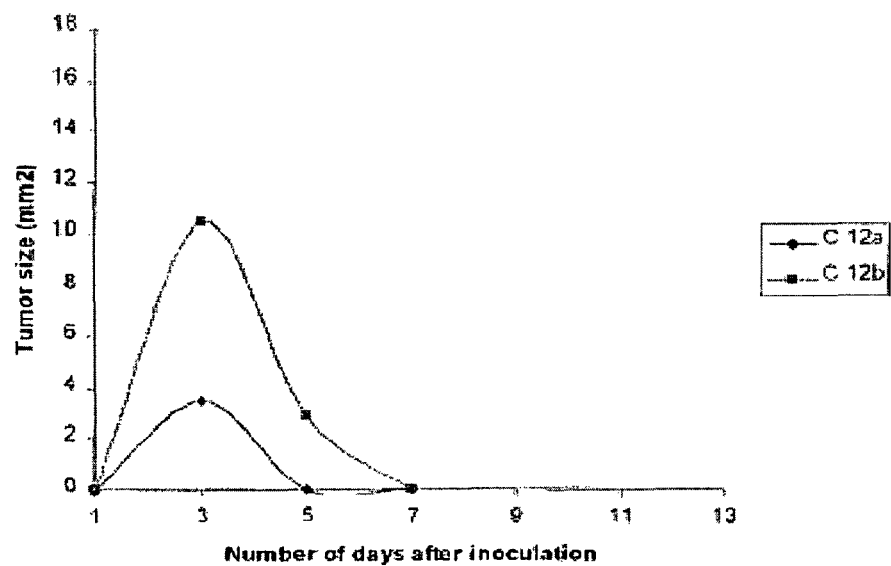
FIG. 14 is a graph showing the effect of re-inoculating A-20 cells in animals that had been successfully treated with C12. The letters a) and b) designate different mice.
Figure 15:
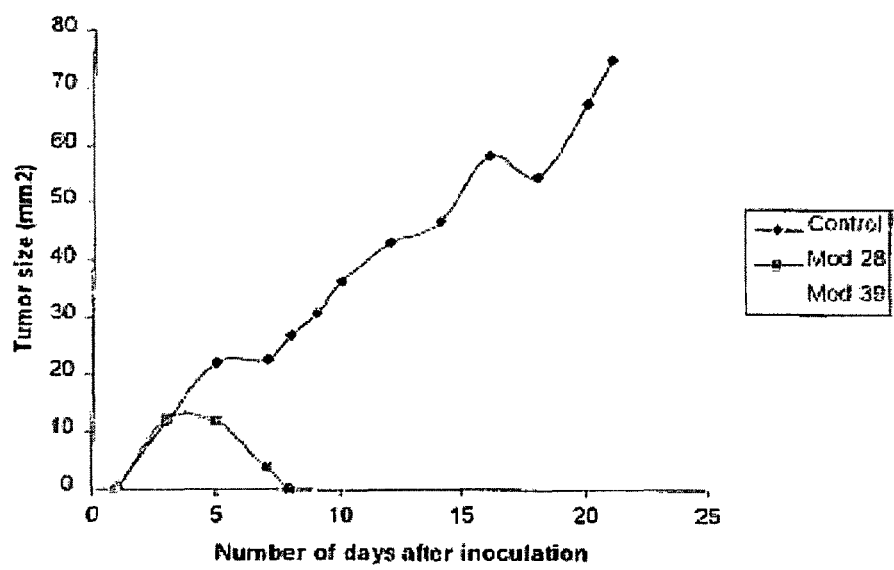
FIG. 15 is a graph showing the effect of re-inoculating A-20 cells in animals that had been successfully treated with Mod 28 or Mod 39. The positive control shows the growth of A20 cells in mice not pre-treated with peptides.

The antitumoral activity of three different peptides against A20 B-cell lymphoblast tumors was studied in syngenic Balb/c mice. The peptides were Model 28, Model 39 and C12 as defined in Example 20. Tumour cells (5×10$^6$) were inoculated subcutaneously on the abdomen of the mice and grown into proper size (20-30 mm$^2$) before peptide treatment. The mice were randomised in groups of 5-6 and the tumors were treated intra-tumorally with 0.5 mg/50 μl peptide once a day for three consecutive days. The tumor size (mean of transversal and longitudinal) was measured with an electronic calliper. Three weeks later, mice that were successfully treated, i.e. showing a full regression of the tumor, received the same number and the same type of tumor cells at similar conditions as described above. The results are presented in FIGS. 13-15.

EXAMPLE 22

Figure 16:
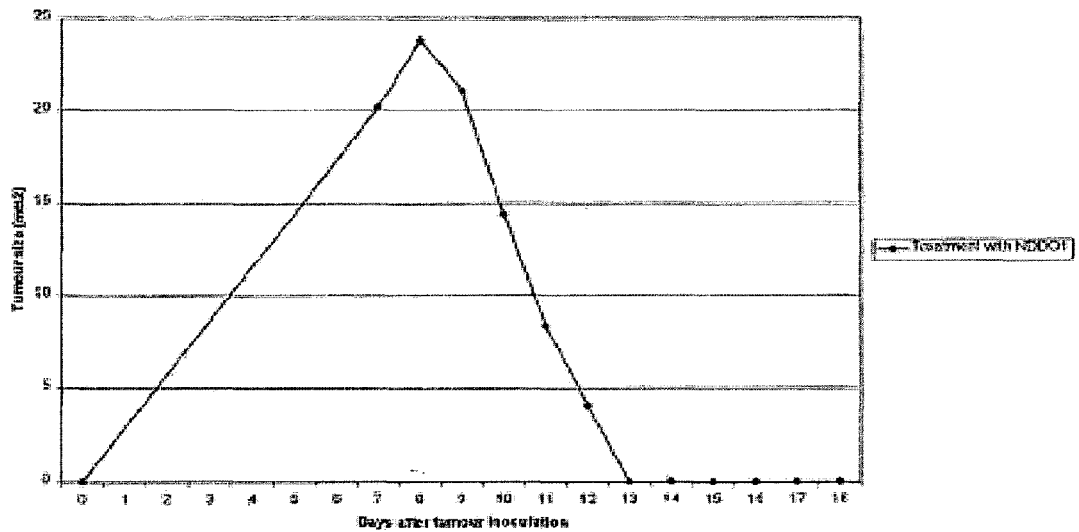
FIG. 16 is a graph showing the primary effect of NDDO1 on C26 colon carcinoma.
Figure 17:
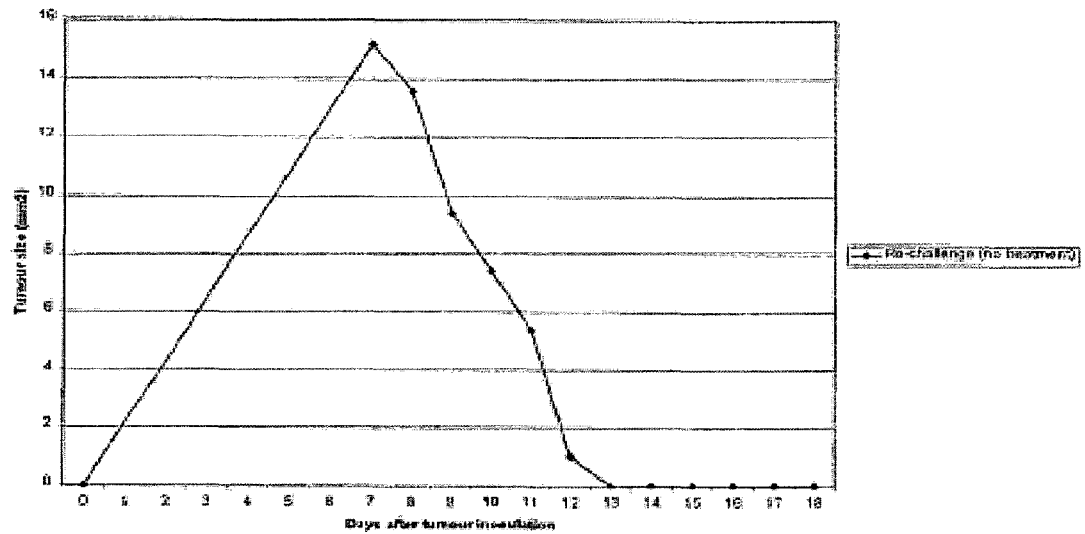
FIG. 17 is a graph showing the effect of re-innoculating C26 cells in a mouse that had been successfully treated with NDDO1.

The antitumoral activity of the peptide, Ad-LFB 14-31 A2,3,6,10,17,F7,R4,K11,L14-NH2, (NDDO1) was tested in a murine C26 colon carcinoma model established in syngenic Balb/c mice. C26 cells (5×10$^6$ cells in 50 μl) cells were inoculated subcutaneously on the abdomen of the mice (3 animals) and grown into proper size (20-30 mm$^2$) before treatment start. At day 7 the tumors were treated intra-tumorally with 0.5 mg/50 μl peptide once a day for three consecutive days and the progression was followed. In one mouse full tumor regression was obtained (FIG. 16). In this mouse C26 tumor cells (5×10$^6$ cells in 50 μl) were re-inoculated subcutaneously three weeks after peptide treatment. A regression of the tumor after an initial growth was obtained without any further treatment (FIG. 17), suggesting that the mouse had acquired an adaptive immune response.

EXAMPLE 23

Initial Tumor Treatment

Syngenic Balb/c mice were selected as a model system to investigate the long-term anti-tumor immunity conferred by an initial treatment with a lytic peptide (H$_2$N-WKKWdip-KKWK-COOH—Mod 39 (SEQ ID NO: 42)) against A20 B-cell lymphoblastoma. Tumour cells (5×10$^6$) were inoculated subcutaneously on the abdomen of the mice and grown into proper size (20-30 mm$^2$) before treatment start. The mice were treated intra-tumorally with 0.5 mg/50 μl peptide once a day for three consecutive days and the progression was followed. Mice that were successfully treated were selected as donors (treated donor) for adoptive transfer of spleen cells, 3 weeks after tumor eradication.

Transfer of Spleen Cells

Day 1—Naive acceptor mice were subjected to a Total Body Irradiation (TBI) of 500 cGy in preparation for receiving adoptive transfer of immune cells from spleen donors.

Day 2—Single-cell suspensions of spleenocytes depleted of red blood cells from treated donor mice and naïve mice were prepared as previously described (Ward, B. A. et al., J. Immunology Aughust 1988, vol 141 p 1047), except that sterile $H_2O$ was used instead of ammonium chloride to eliminate red blood cells.

Donor spleen cells (approximately 40 million) were injected i.v. into the tail vein of acceptor mice according to the methods described in Bogen B. et al., Eur J Immunology, May 1983, vol 13(5), pages 353-359.

Day 3—Tumour cells ($5\times10^6$) were inoculated subcutaneously on the abdomen of the mice and growth was followed by measuring tumor size with a calliper.

Figure 18:
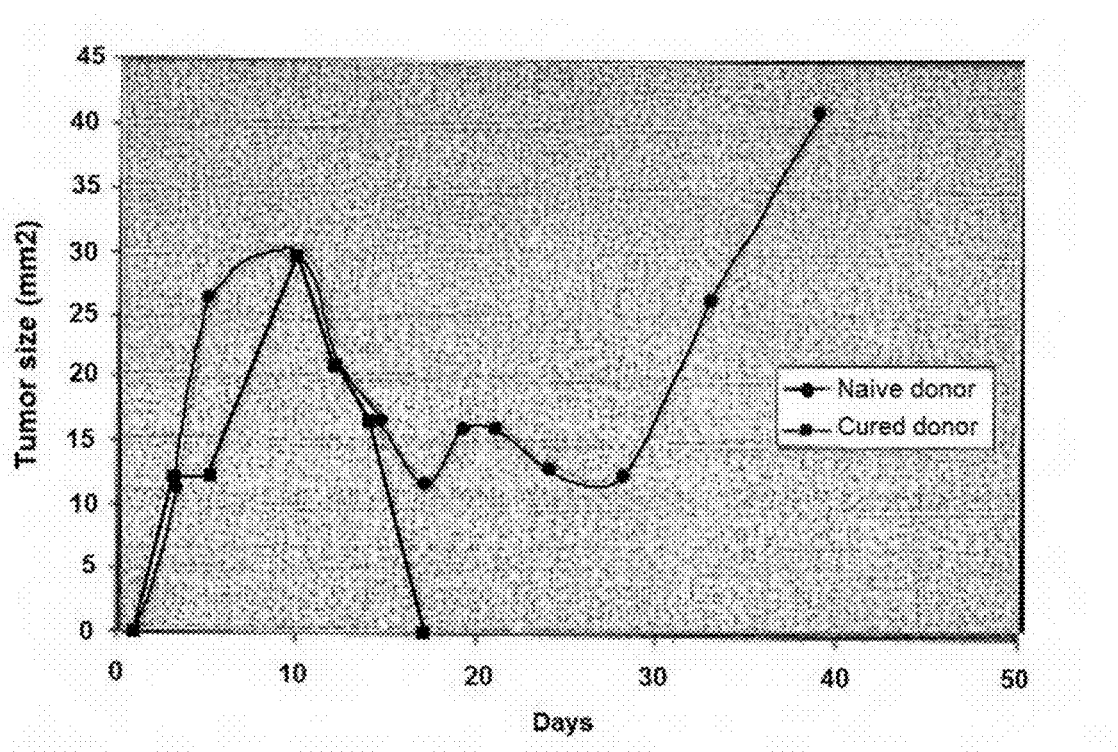
FIG. 18 is a graph showing adoptive transfer of specific anti-A20 cancer immunity from successfully cured mice (treated with Mod39 lytic peptide) vs. naive, untreated mice. Acceptors that received spleen cells from previously cured mice were able to reject implanted tumors, whereas acceptors that received spleen cells from naive mice were unable to reject the tumor.

The results demonstrate that the transfer of immune cells from a previously successfully treated mouse confers immunity towards the same tumor type in the acceptor mice (FIG. 18—"Cured" group). In contrast, after transfer of immune cells from naïve donor mice the implanted tumor does not regress (FIG. 18—"Naive" group). These results demonstrate that the protective effect is due to the previously successful tumor eradication that confers a long-term, specific immunity against the tumor type.

Examples 20-23 were carried out using the trifluoroacetate (TFA) salt form of the peptides referred to.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

All patents, applications, publications, test methods, literature, and other materials cited herein are hereby incorporated herein by reference in their entireties.

The invention claimed is:

1. A method of inducing adaptive immunity against tumour growth or establishment in a subject having a tumour, comprising administration of an effective amount of a lytic peptide or peptidomimetic to said subject, wherein said peptide or peptidomimetic is from 3 to 30 amino acids or equivalent in length, and comprises two or more cationic residues and one or more bulky and lipophilic residues, wherein said bulky and lipophilic residues comprise a side chain containing 7 or more non-hydrogen atoms, said peptide or peptidomimetic may be cyclic or in the form of an ester, amide or salt, and whereby adaptive immunity against tumour growth or establishment is induced.

2. The method according to claim 1, wherein the lytic peptide or peptidomimetic, through lysis of cells in a first tumour, generates an immune response which inhibits the growth or establishment of a second tumor, wherein the first tumour and the second tumor are of the same cancer type.

3. The method according to claim 1, wherein the peptide or peptidomimetic includes one or more non-genetic bulky and lipophilic amino acids.

4. The method according to claim 1, wherein the lytic peptide or peptidomimetic includes two groups which are bulky and lipophilic and contain 7 or more non-hydrogen atoms.

5. The method according to claim 1, wherein the lytic peptide or peptidomimetic contains at least one biphenylalamine (Bip) and/or at least one diphenylalamine (Dip) residue and/or 1-5 tryptophan residues.

6. The method according to claim 1, wherein the peptide or peptidomimetic is in salt form.

7. The method according to claim 1, wherein the lytic peptide or peptidomimetic is delivered intratumorally.

8. The method according to claim 2, wherein the inhibition of growth is regression of the tumour.

9. The method according to claim 2, wherein the inhibition of growth includes the prevention of establishment of a second tumour.

10. The method according to claim 2, wherein the second tumour is a secondary tumour.

11. The method according to claim 1, wherein the tumour is selected from the group consisting of lymphomas, carcinomas and sarcomas.

12. The method according to claim 1, wherein the tumour is a benign tumour.

13. The method of claim 1, wherein the subject is an animal other than a mouse.

14. The method of claim 1, wherein the subject is a human.

15. The method of claim 13, wherein the peptide or peptidomimetic is administered daily for at least 2 days.

16. The method of claim 13, wherein the peptide or peptidomimetic is administered from two to five times.

17. The method of claim 14, wherein the peptide or peptidomimetic is administered daily for at least 2 days.

18. The method of claim 14, wherein the peptide or peptidomimetic is administered from two to five times.

* * * * *

SEQUENCE LISTING

<160> NUMBER OF SEQ ID NOS: 42

<210> SEQ ID NO 1
<211> LENGTH: 15
<212> TYPE: PRT
<213> ORGANISM: Bos sp.

<400> SEQUENCE: 1

Phe Lys Cys Arg Arg Trp Gln Trp Arg Met Lys Lys Leu Gly Ala
 1               5                   10                  15

<210> SEQ ID NO 2
<211> LENGTH: 15
<212> TYPE: PRT
<213> ORGANISM: Homo sapiens

<400> SEQUENCE: 2

Thr Lys Cys Phe Gln Trp Gln Arg Asn Met Arg Lys Val Arg Gly
 1               5                   10                  15

<210> SEQ ID NO 3
<211> LENGTH: 15
<212> TYPE: PRT
<213> ORGANISM: Capra sp.

<400> SEQUENCE: 3

Ser Lys Cys Tyr Gln Trp Gln Arg Arg Met Arg Lys Leu Gly Ala
 1               5                   10                  15

<210> SEQ ID NO 4
<211> LENGTH: 15
<212> TYPE: PRT
<213> ORGANISM: Mus sp.

<400> SEQUENCE: 4

Glu Lys Cys Leu Arg Trp Gln Asn Glu Met Arg Lys Val Gly Gly
 1               5                   10                  15

<210> SEQ ID NO 5
<211> LENGTH: 15
<212> TYPE: PRT
<213> ORGANISM: Sus sp.

<400> SEQUENCE: 5

Ser Lys Cys Arg Gln Trp Gln Ser Lys Ile Arg Arg Thr Asn Pro
1               5                   10                  15

<210> SEQ ID NO 6
<211> LENGTH: 25
<212> TYPE: PRT
<213> ORGANISM: Bos sp.

<400> SEQUENCE: 6

Phe Lys Cys Arg Arg Trp Gln Trp Arg Met Lys Lys Leu Gly Ala Pro
1               5                   10                  15

Ser Ile Thr Cys Val Arg Arg Ala Phe
            20                  25

<210> SEQ ID NO 7
<211> LENGTH: 25
<212> TYPE: PRT
<213> ORGANISM: Homo sapiens

<400> SEQUENCE: 7

Thr Lys Cys Phe Gln Trp Gln Arg Asn Met Arg Lys Val Arg Cys Pro
1               5                   10                  15

Pro Val Glu Cys Ile Lys Arg Asp Ser
            20                  25

<210> SEQ ID NO 8
<211> LENGTH: 25
<212> TYPE: PRT
<213> ORGANISM: Bos sp.

<400> SEQUENCE: 8

Phe Lys Cys Arg Arg Trp Gln Trp Arg Met Lys Lys Leu Gly Ala Pro
1               5                   10                  15

Ser Ile Thr Cys Val Arg Arg Ala Phe
            20                  25

<210> SEQ ID NO 9
<211> LENGTH: 25
<212> TYPE: PRT
<213> ORGANISM: Mus sp.

<400> SEQUENCE: 9

Glu Lys Cys Leu Arg Trp Gln Asn Glu Met Arg Lys Val Gly Gly Pro
1               5                   10                  15

Pro Leu Ser Cys Val Lys Lys Ser Ser
            20                  25

<210> SEQ ID NO 10
<211> LENGTH: 25
<212> TYPE: PRT
<213> ORGANISM: Capra sp.

<400> SEQUENCE: 10

Ser Lys Cys Tyr Gln Trp Gln Arg Arg Met Arg Lys Leu Gly Ala Pro
1               5                   10                  15

Ser Ile Thr Cys Val Arg Arg Thr Ser
            20                  25

<210> SEQ ID NO 11
<211> LENGTH: 18
<212> TYPE: PRT
<213> ORGANISM: Bos sp.

<400> SEQUENCE: 11

Pro Glu Trp Phe Lys Cys Arg Arg Trp Gln Trp Arg Met Lys Lys Leu
1               5                   10                  15
Gly Ala

<210> SEQ ID NO 12
<211> LENGTH: 15
<212> TYPE: PRT
<213> ORGANISM: Bos sp.

<400> SEQUENCE: 12

Phe Lys Cys Arg Arg Trp Gln Trp Arg Met Lys Lys Leu Gly Ala
1               5                   10                  15

<210> SEQ ID NO 13
<211> LENGTH: 14
<212> TYPE: PRT
<213> ORGANISM: Bos sp.

<400> SEQUENCE: 13

Lys Cys Arg Arg Trp Gln Trp Arg Met Lys Lys Leu Gly Ala
1               5                   10

<210> SEQ ID NO 14
<211> LENGTH: 13
<212> TYPE: PRT
<213> ORGANISM: Bos sp.

<400> SEQUENCE: 14

Cys Arg Arg Trp Gln Trp Arg Met Lys Lys Leu Gly Ala
1               5                   10

<210> SEQ ID NO 15
<211> LENGTH: 12
<212> TYPE: PRT
<213> ORGANISM: Bos sp.

<400> SEQUENCE: 15

Arg Arg Trp Gln Trp Arg Met Lys Lys Leu Gly Ala
1               5                   10

<210> SEQ ID NO 16
<211> LENGTH: 15
<212> TYPE: PRT
<213> ORGANISM: Bos sp.

<400> SEQUENCE: 16

Lys Lys Cys Arg Arg Trp Gln Trp Arg Met Lys Lys Leu Gly Ala
1               5                   10                  15

<210> SEQ ID NO 17
<211> LENGTH: 15
<212> TYPE: PRT
<213> ORGANISM: Bos sp.

<400> SEQUENCE: 17

Phe Lys Cys Phe Arg Trp Gln Trp Arg Met Lys Lys Leu Gly Ala
1               5                   10                  15

<210> SEQ ID NO 18
<211> LENGTH: 15
<212> TYPE: PRT
<213> ORGANISM: Bos sp.

```
<400> SEQUENCE: 18

Lys Lys Cys Phe Arg Trp Gln Trp Arg Met Lys Lys Leu Gly Ala
 1               5                  10                  15

<210> SEQ ID NO 19
<211> LENGTH: 15
<212> TYPE: PRT
<213> ORGANISM: Bos sp.

<400> SEQUENCE: 19

Phe Lys Cys Arg Arg Trp Gln Trp Arg Met Lys Lys Leu Gly Ala
 1               5                  10                  15

<210> SEQ ID NO 20
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Thr Lys Cys Phe Gln Trp Gln Trp Asn Met Arg Lys Val Arg Gly
 1               5                  10                  15

<210> SEQ ID NO 21
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Ser Lys Cys Tyr Gln Trp Gln Trp Arg Met Arg Lys Leu Gly Ala
 1               5                  10                  15

<210> SEQ ID NO 22
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Glu Lys Cys Leu Arg Trp Gln Trp Glu Met Arg Lys Val Gly Gly
 1               5                  10                  15

<210> SEQ ID NO 23
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Phe Lys Trp Arg Arg Trp Gln Trp Arg Met Lys Lys Leu Gly Ala
 1               5                  10                  15

<210> SEQ ID NO 24
<211> LENGTH: 15
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 24

Phe Lys Cys Arg Arg Trp Gln Trp Arg Met Lys Lys Leu Trp Ala
  1               5                  10                  15

<210> SEQ ID NO 25
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Phe Lys Trp Arg Arg Trp Gln Trp Arg Met Lys Lys Leu Trp Ala
  1               5                  10                  15

<210> SEQ ID NO 26
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Phe Lys Trp Arg Arg Trp Trp Trp Arg Met Lys Lys Leu Trp Ala
  1               5                  10                  15

<210> SEQ ID NO 27
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Phe Lys Cys Trp Arg Trp Gln Trp Arg Trp Lys Lys Leu Gly Ala
  1               5                  10                  15

<210> SEQ ID NO 28
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Gly Ile Gly Lys Phe Leu His Ser Ala Lys Lys Phe Gly Lys Ala Phe
  1               5                  10                  15

Val Gly Glu Ile Met Asn Ser
            20

<210> SEQ ID NO 29
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Gly Ile Gly Lys Phe Leu Lys Lys Ala Arg Lys Phe Gly Arg Ala Phe

```
                1               5                   10                  15

Val Arg Ile Leu Lys Lys Gly
                20

<210> SEQ ID NO 30
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Lys Met Ala Ser Lys Ala Gly Lys Ile Ala Gly Lys Ile Ala Lys Val
  1               5                   10                  15

Ala Leu Lys Ala Leu
                20

<210> SEQ ID NO 31
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Lys Val Ala Leu Lys Ala Leu Lys Val Ala Leu Lys Ala Leu Lys Val
  1               5                   10                  15

Ala Leu Lys Ala Leu
                20

<210> SEQ ID NO 32
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Tyr Arg Ala Trp Arg Trp Ala Trp Arg Trp Arg
  1               5                   10

<210> SEQ ID NO 33
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: D-Tyr
<220> FEATURE:
<221> NAME/KEY: MOD_RES
<222> LOCATION: (3)
<223> OTHER INFORMATION: D-Ala
<220> FEATURE:
<221> NAME/KEY: MOD_RES
<222> LOCATION: (5)
<223> OTHER INFORMATION: D-Arg
<220> FEATURE:
<221> NAME/KEY: MOD_RES
<222> LOCATION: (7)
<223> OTHER INFORMATION: D-Ala
<220> FEATURE:
<221> NAME/KEY: MOD_RES
```

```
<222> LOCATION: (9)
<223> OTHER INFORMATION: D-Arg
<220> FEATURE:
<221> NAME/KEY: MOD_RES
<222> LOCATION: (11)
<223> OTHER INFORMATION: D-Arg

<400> SEQUENCE: 33

Tyr Arg Ala Trp Arg Trp Ala Trp Arg Trp Arg
 1               5                  10

<210> SEQ ID NO 34
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: D-Tyr
<220> FEATURE:
<221> NAME/KEY: MOD_RES
<222> LOCATION: (2)
<223> OTHER INFORMATION: D-Arg
<220> FEATURE:
<221> NAME/KEY: MOD_RES
<222> LOCATION: (3)
<223> OTHER INFORMATION: D-Ala
<220> FEATURE:
<221> NAME/KEY: MOD_RES
<222> LOCATION: (7)
<223> OTHER INFORMATION: D-Ala

<400> SEQUENCE: 34

Tyr Arg Ala Trp Arg Trp Ala Trp Arg Trp Arg
 1               5                  10

<210> SEQ ID NO 35
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Arg Trp Trp Arg Tyr Trp Arg
 1               5

<210> SEQ ID NO 36
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: D-Arg
<220> FEATURE:
<221> NAME/KEY: MOD_RES
<222> LOCATION: (3)
<223> OTHER INFORMATION: D-Trp
<220> FEATURE:
<221> NAME/KEY: MOD_RES
<222> LOCATION: (5)
<223> OTHER INFORMATION: D-Tyr
<220> FEATURE:
<221> NAME/KEY: MOD_RES
<222> LOCATION: (7)
```

```
<223> OTHER INFORMATION: D-Arg

<400> SEQUENCE: 36

Arg Trp Trp Arg Tyr Trp Arg
 1               5

<210> SEQ ID NO 37
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: D-Arg
<220> FEATURE:
<221> NAME/KEY: MOD_RES
<222> LOCATION: (2)
<223> OTHER INFORMATION: D-Trp
<220> FEATURE:
<221> NAME/KEY: MOD_RES
<222> LOCATION: (6)
<223> OTHER INFORMATION: D-Trp
<220> FEATURE:
<221> NAME/KEY: MOD_RES
<222> LOCATION: (7)
<223> OTHER INFORMATION: D-Arg

<400> SEQUENCE: 37

Arg Trp Trp Arg Tyr Trp Arg
 1               5

<210> SEQ ID NO 38
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Phe Lys Cys Arg Arg Trp Gln Trp Arg Met Lys Lys Leu Gly Ala Pro
 1               5                  10                  15

Ser Ile Thr Cys Val Arg Arg Ala Phe
            20                  25

<210> SEQ ID NO 39
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)
<223> OTHER INFORMATION: bip
<220> FEATURE:
<221> NAME/KEY: MOD_RES
<222> LOCATION: (16)
<223> OTHER INFORMATION: bip

<400> SEQUENCE: 39

Lys Ala Ala Lys Lys Ala Ala Lys Ala Xaa Lys Lys Ala Ala Lys Xaa
 1               5                  10                  15

Lys Lys Ala Ala
            20
```

```
<210> SEQ ID NO 40
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)
<223> OTHER INFORMATION: dip

<400> SEQUENCE: 40

Trp Lys Lys Trp Xaa Lys Lys Trp Lys
  1               5

<210> SEQ ID NO 41
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)
<223> OTHER INFORMATION: bip
<220> FEATURE:
<221> NAME/KEY: MOD_RES
<222> LOCATION: (13)
<223> OTHER INFORMATION: bip

<400> SEQUENCE: 41

Lys Ala Ala Lys Lys Ala Xaa Lys Ala Ala Lys Ala Xaa Lys Lys Ala
  1               5                  10                  15

Ala

<210> SEQ ID NO 42
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)
<223> OTHER INFORMATION: dip

<400> SEQUENCE: 42

Trp Lys Lys Trp Xaa Lys Lys Trp Lys
  1               5
```